(12) United States Patent
Friera et al.

(10) Patent No.: US 7,067,266 B2
(45) Date of Patent: Jun. 27, 2006

(54) MODULATORS OF LEUKOCYTE ACTIVATION, HCK COMPOSITIONS AND METHODS OF USE

(75) Inventors: Annabelle Friera, South San Francisco, CA (US); Brian R. Wong, San Mateo, CA (US); Esteban Masuda, Menlo Park, CA (US); Mark Powell, Burlingame, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 439 days.

(21) Appl. No.: 10/193,720

(22) Filed: Jul. 10, 2002

(65) Prior Publication Data

US 2004/0009173 A1    Jan. 15, 2004

(51) Int. Cl.
  *C12Q 1/02*   (2006.01)
  *C12Q 1/48*   (2006.01)
  *G01N 33/566*   (2006.01)

(52) U.S. Cl. ......................... 435/7.24; 435/15; 435/29; 436/63; 436/501

(58) Field of Classification Search .................... 435/7, 435/24, 15, 29; 436/63, 501
See application file for complete search history.

(56) References Cited

U.S. PATENT DOCUMENTS

| 6,239,133 B1 * | 5/2001 | Barrish et al. ............... 514/250 |
| 2001/0006789 A1 * | 7/2001 | Maino et al. ............... 435/7.21 |
| 2002/0076733 A1 * | 6/2002 | Kasibhatla et al. ......... 435/7.21 |

OTHER PUBLICATIONS

Bosco et al., "IL-2 Signaling In Human Monocytes Involves the Phosphorylation and Activation of p59[hck1]", *J. Immunol.* 164: 4575-4585 (2000).
Brown et al., "Activation of the PAK-Related Kinase by Human Immunodeficiency Virus Type 1 Nef in Primary Human Peripheral Blood Lymphocytes and Macrophages Leads to Phosphorylation of a PIX-p95 Complex", *Journal of Virology* 73:12: 9899-9907 (1999).
Kim et al., "Signaling Function of the B-Cell Antigen Receptors", *Immunological Reviews* 132: 126-145 (1993).
Reth, "Antigen Receptors on B Lymphocytes", *Annu. Rev. Immunol.* 10: 97-121 (1992).
Schlessinger, "Cell Signaling by Receptor Tyrosine Kinases", *Cell:* 103: 211-225 (2000).
Scott et al., "Identification of Novel SH3 Domain Ligards for the Src Family Kinase Hck", *The Journal of Biological Chemistry* 277:31: 28238-28246 (2002).
Quintrell et al., "Identification of a Human Gene (HCK) That Encodes a Protein-Tyrosine Kinase and is Expressed in Hemopoietic Cells", *Molecular and Cellular Biology* 7:6: 2267-2275 (1987).
Verkoczy et al., "Characterization of the Human B Cell RAG-associated Gene, *hBRAG*, as a B Cell Receptor Signal-enhancing Glycoprotein Dimer That Associates with Phosphorylated Proteins in Resting B Cells", *The Journal of Biological Chemistry* 275:28: 20967-20979 (2000>.
Ziegler et al., "Novel Protein-Tyrosine Kinase Gene (*hck*) Preferentially Expressed in Cells of Hematopoietic Origin", *Molecular and Cellular Biology* 7:6: 2276-2285 (1987).
Zilber et al., "CD38 expressed on human monocytes: A coaccessory molecule in the superantigen-induced proliferation", *PNAS* 97:6: 2840-2845 (2000).

* cited by examiner

*Primary Examiner*—David Saunders
(74) *Attorney, Agent, or Firm*—Townsend and Townsend and Crew LLP

(57) ABSTRACT

The present invention provides compositions and methods for modulating leukocyte activation. Nucleic acids encoding proteins and proteins so encoded which are capable of modulating leukocyte activation are provided. Compositions and methods for the treatment of disorders related to leukocyte dysfunction or dysregulation are also provided. Prophylactics and methods for the prevention of such disorders are also provided. Also provided are compositions and methods for diagnostic and prognostic determination of such disorders. Further provided are assays for the identification of bioactive agents capable of modulating leukocyte activation.

26 Claims, 16 Drawing Sheets

```
  1   acctcagggg ctgccgagct gggggggcgc tcaagctgcg aggatccggg ctgcccgcga
 61   gacgaggagc gggcgcgatg gggtgcatga agtccaagtt cctccaggtc ggaggcaata
121   cattctcaaa aactgaaacc agcgccagcc cacactgtcc tgtgtacgtg ccggatccca
181   catccaccat caagccgggg cctaatagcc acaacagcaa cacaccagga atcagggagg
241   caggctctga ggacatcatc gtggttgccc tgtatgatta cgaggccatt caccacgaag
301   acctcagctt ccagaagggg gaccagatgg tggtcctaga ggaatccggg gagtggtgga
361   aggctcgatc cctggccacc cggaaggagg gctacatccc aagcaactat gtcgcccgcg
421   tgactctct ggagacagag gagtggtttt tcaagggcat cagccggaag gacgcagagc
481   gccaactgct ggctcccggc aacatgctgg gctccttcat gatccgggat agcgagacca
541   ctaaaggaag ctactctttg tccgtgcgag actacgaccc tcggcaggga gataccgtga
601   aacattacaa gatccggacc ctggacaacg ggggcttcta catatccccc gaagcacct
661   tcagcactct gcaggagctg gtggaccact acaagaaggg gaacgacggg ctctgccaga
721   aactgtcggt gccctgcatg tcttccaagc cccagaagcc ttgggagaaa gatgcctggg
781   agatccctcg gaatccctc aagctggaga agaaacttgg agctgggcag tttggggaag
841   tctggatggc cacctacaac aagcacacca aggtggcagt gaagacgatg aagccaggga
901   gcatgtcggt ggaggccttc ctggcagagg ccaacgtgat gaaaactctg cagcatgaca
961   agctggtcaa acttcatgcg gtggtcacca aggagcccat ctacatcatc acggagttca
1021  tggccaaagg aagcttgctg gactttctga aagtgatga gggcagcaag cagccattgc
1081  caaaactcat tgacttctca gcccagattg cagaaggcat ggccttcatc gagcagagga
1141  actacatcca ccgagacctc cgagctgcca acatcttggt ctctgcatcc ctggtgtgta
1201  agattgctga ctttggcctg gcccgggtca ttgaggacaa cgagtacacg gctcgggaag
1261  gggccaagtt ccccatcaag tggacagctc ctgaagccat caactttggc tccttcacca
1321  tcaagtcaga cgtctggtcc tttggtatcc tgctgatgga gatcgtcacc tacggccgga
1381  tcccttaccc agggatgtca aaccctgaag tgatccgagc tctggagcgt ggataccgga
1441  tgcctcgccc agagaactgc ccagaggagc tctacaacat catgatgcgc tgctggaaaa
1501  accgtccgga ggagcggccg accttcgaat acatccagag tgtgctggat gacttctaca
1561  cggccacaga gagccagtac aacagcagc atgatagggg aggaccaggg cagggccagg
1621  gggtgcccag gtggtggctg caaggtggct ccagcaccat ccgccagggc cacacccccc
1681  ttcctactcc cagacaccca ccctcgcttc agccacagtt tcctcatctg tccagtgggt
1741  aggttggact ggaaaatctc tttttgactc ttgcaatcca caatctgaca ttctcaggaa
1801  gcccccaagt tgatatttct atttcctgga atggttggat tttagttaca gctgtgattt
1861  ggaagggaaa ctttcaaaat agtgaaatga atatttaaat aaaagatata aatgccaaag
1921  tctt
``` cds 78-1595, 505 aa

Human HCK

FIG._1

```
  1   MGCMKSKFLQ VGGNTFSKTE TSASPHCPVY VPDPTSTIKP GPNSHNSNTP
 51   GIREAGSEDI IVVALYDYEA IHHEDLSFQK GDQMVVLEES GEWWKARSLA
101   TRKEGYIPSN YVARVDSLET EEWFFKGISR KDAERQLLAP GNMLGSFMIR
151   DSETTKGSYS LSVRDYDPRQ GDTVKHYKIR TLDNGGFYIS PRSTFSTLQE
201   LVDHYKKGND GLCQKLSVPC MSSKPQKPWE KDAWEIPRES LKLEKKLGAG
251   QFGEVWMATY NKHTKVAVKT MKPGSMSVEA FLAEANVMKT LQHDKLVKLH
301   AVVTKEPIYI ITEFMAKGSL LDFLKSDEGS KQPLPKLIDF SAQIAEGMAF
351   IEQRNYIHRD LRAANILVSA SLVCKIADFG LARVIEDNEY TAREGAKFPI
401   KWTAPEAINF GSFTIKSDVW SFGILLMEIV TYGRIPYPGM SNPEVIRALE
451   RGYRMPRPEN CPEELYNIMM RCWKNRPEER PTFEYIQSVL DDFYTATESQ
501   YQQQP
```

Human HCK, 505 aa
lysine in catalytic kinase domain (k269), indicated in bold

FIG._2

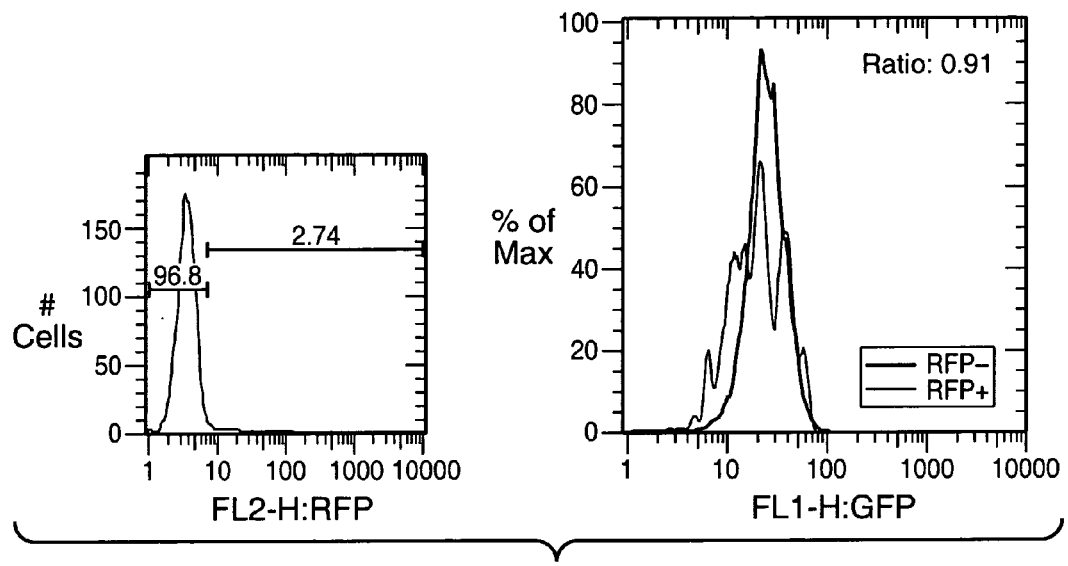
FIG._3A
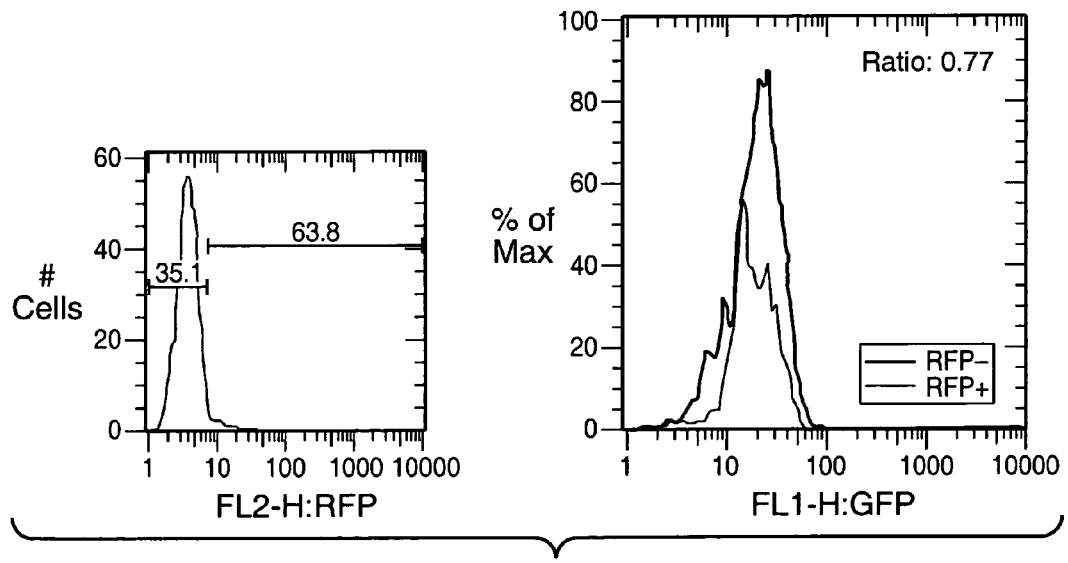
FIG._3B

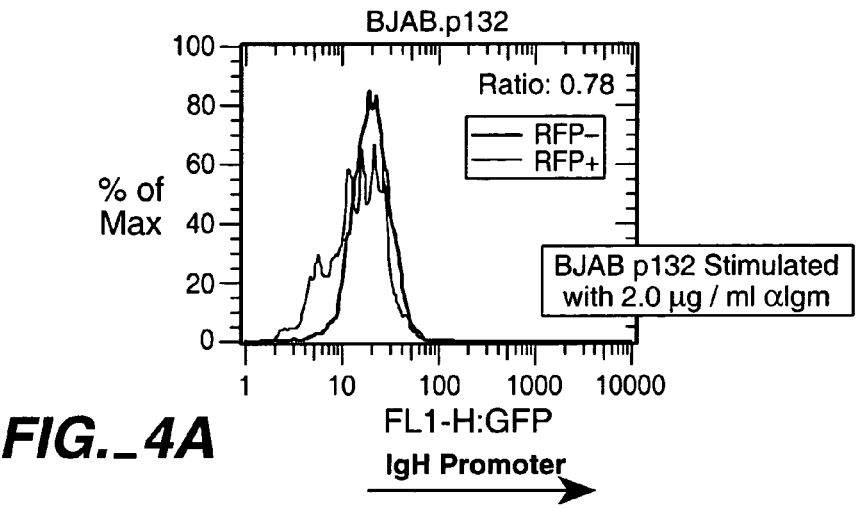
FIG._4A
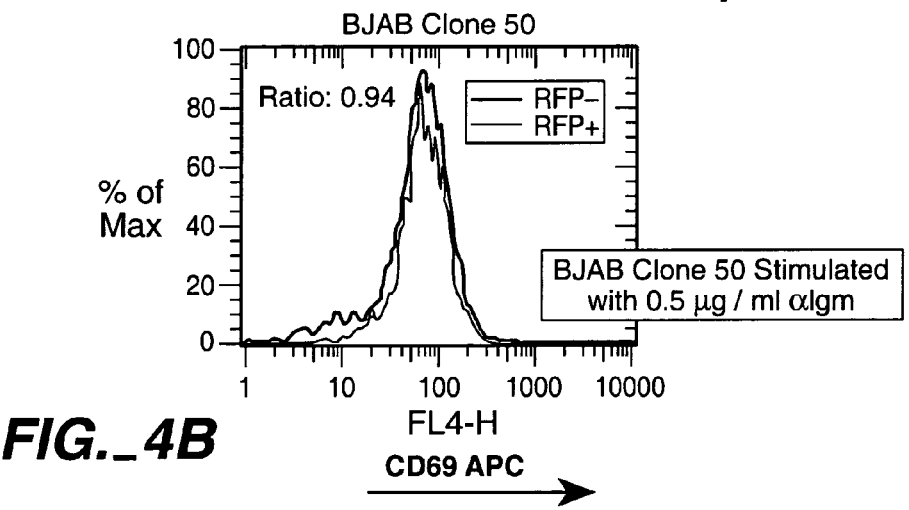
FIG._4B
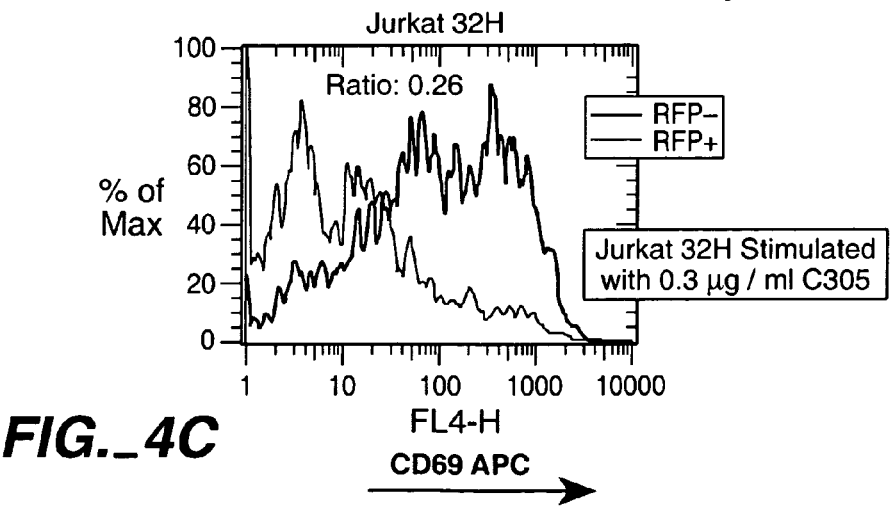
FIG._4C

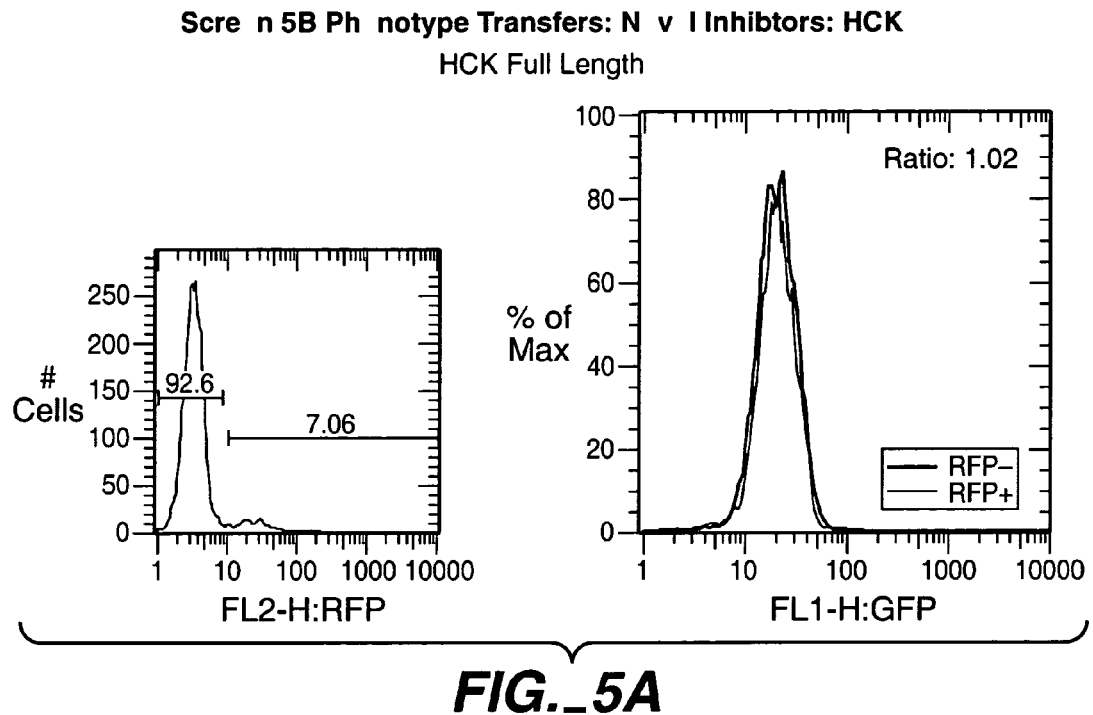
FIG._5A
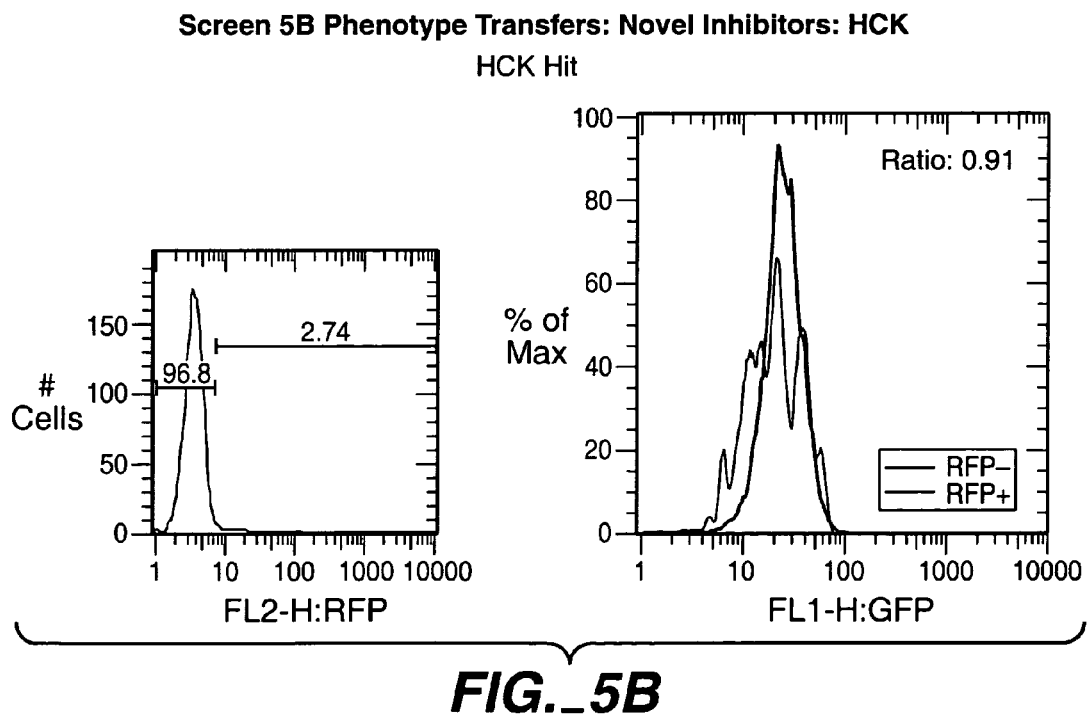
FIG._5B

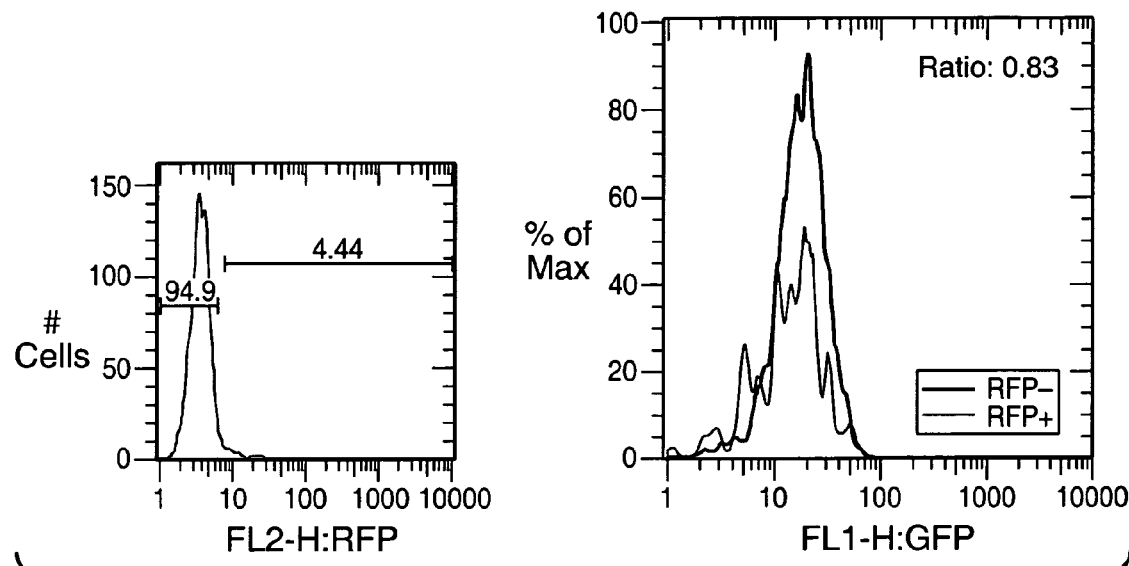
FIG._5C
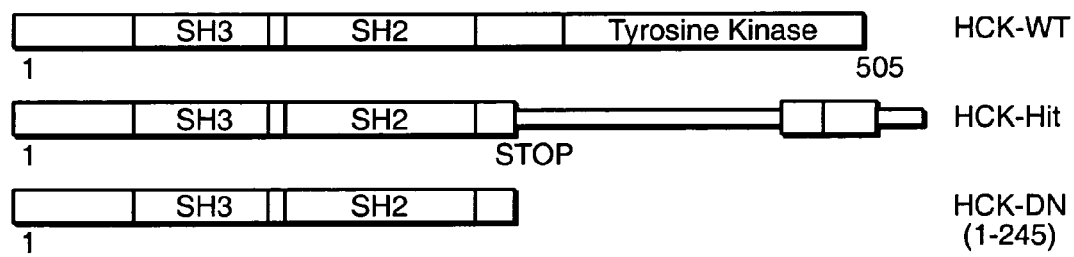
FIG._5D

TABLE 1

Human Autoimmune Diseases

| Disease | Self-Antigen | Immune Response |
|---|---|---|
| Organ-Specific Autoimmune Disease | | |
| Addison's disease | Adrenal cells | Autoantibodies |
| Autoimmune hemolytic anemia | Red blood cells | Autoantibodies |
| Goodpasture's disease | Renal and lung membranes | Autoantibodies |
| Graves' disease | Thyroid-stimulating hormone receptor | Autoantibodies |
| Hashimoto's thyroiditis | Thyroid proteins | $T_{DTH}$ cells, autoantibodies |
| Idiopathic thrombocytopenia | Platelet membranes | Autoantibodies |
| Insulin-dependent diatetes mellitus (IDDM) | Pancreatic beta cells | $T_{DTH}$ cells, autoantibodies |
| Myasthenia gravis | Acetylcholine receptors | Autoantibodies |
| Myocardial infarction | Heart muscle | Autoantibodies |
| Pernicious anemia | Gastric intrinsic factor | Autoantibodies |
| Poststreptococcal glomerulonephritis | Kidney | Immune complexes |
| Spontaneous inferility | Sperm | Autoantibodies |
| Systemic Autoimmune Disease | | |
| Ankylosing spondylitis | Vertebrae | Immune complexes |
| Multiple sclerosis | Brain or white matter | $T_{DTH}$ and $T_c$ cells, autoantibodies |
| Rheumatoid arthritis | Connective tissue | Autoantibodies, immune complexes |
| Scleroderma | Nuclei, heart, lungs, GI tract, Kidney | Autoantibodies |
| Sjogren's syndrome | Salivary gland, liver, kidney, thyroid | Autoantibodies |
| Systemic lupus erythematosus (SLE) | DNA, nuclear protein, RBC and platelet membranes | Autoantibodies, immune complexes |

*FIG._6*

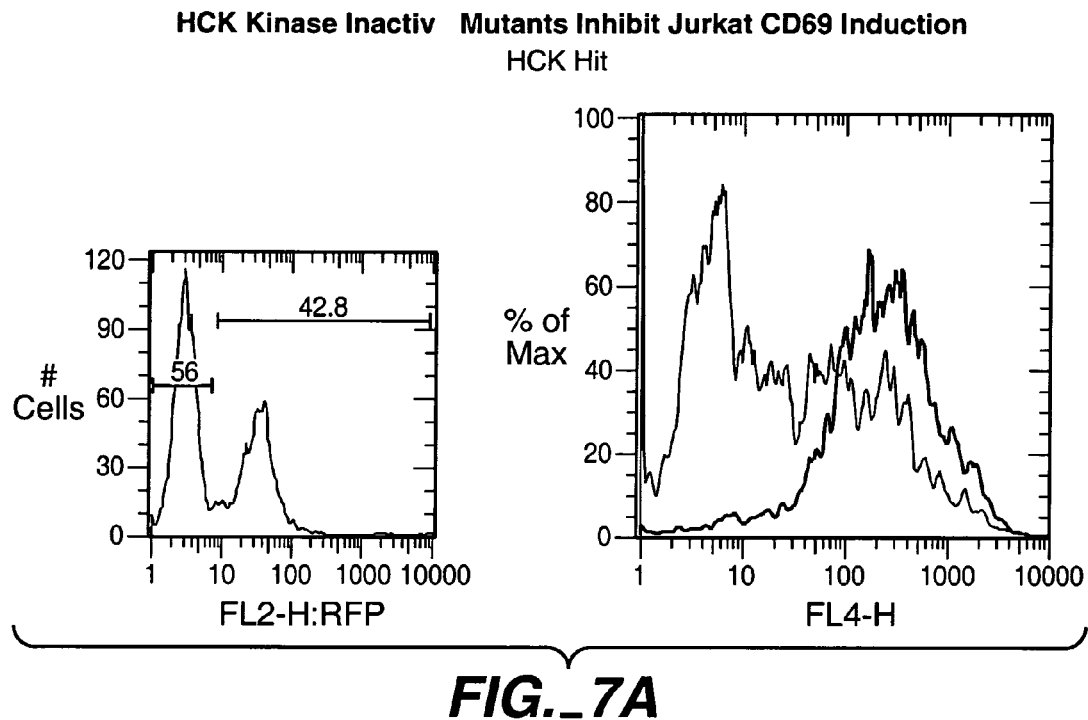
FIG._7A
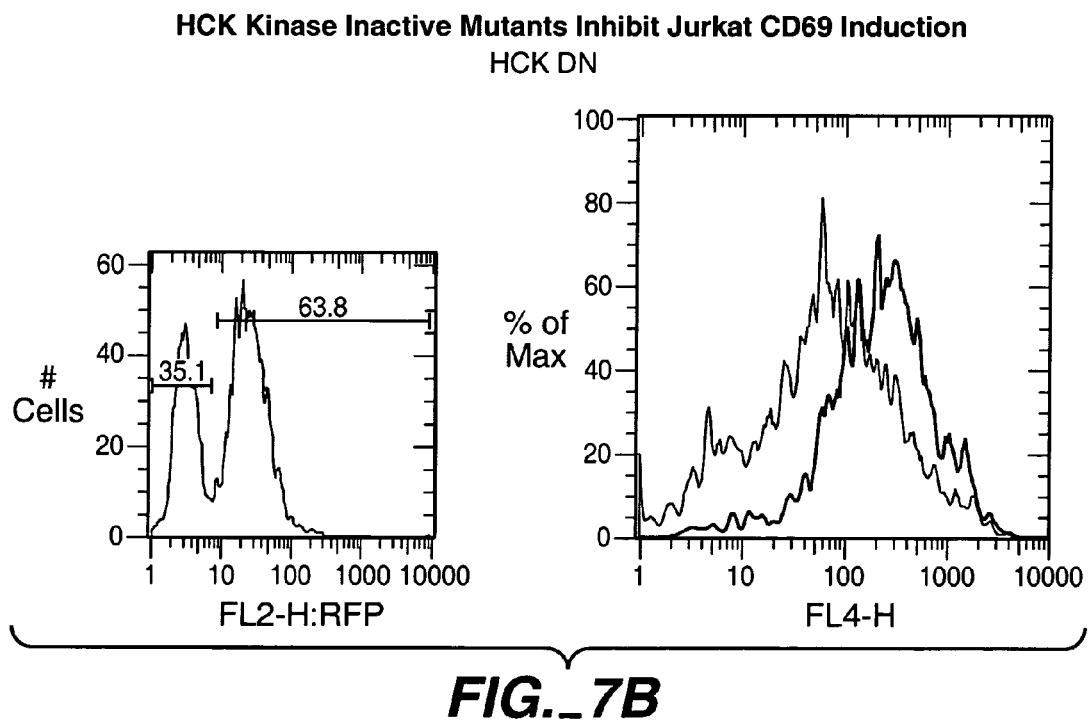
FIG._7B

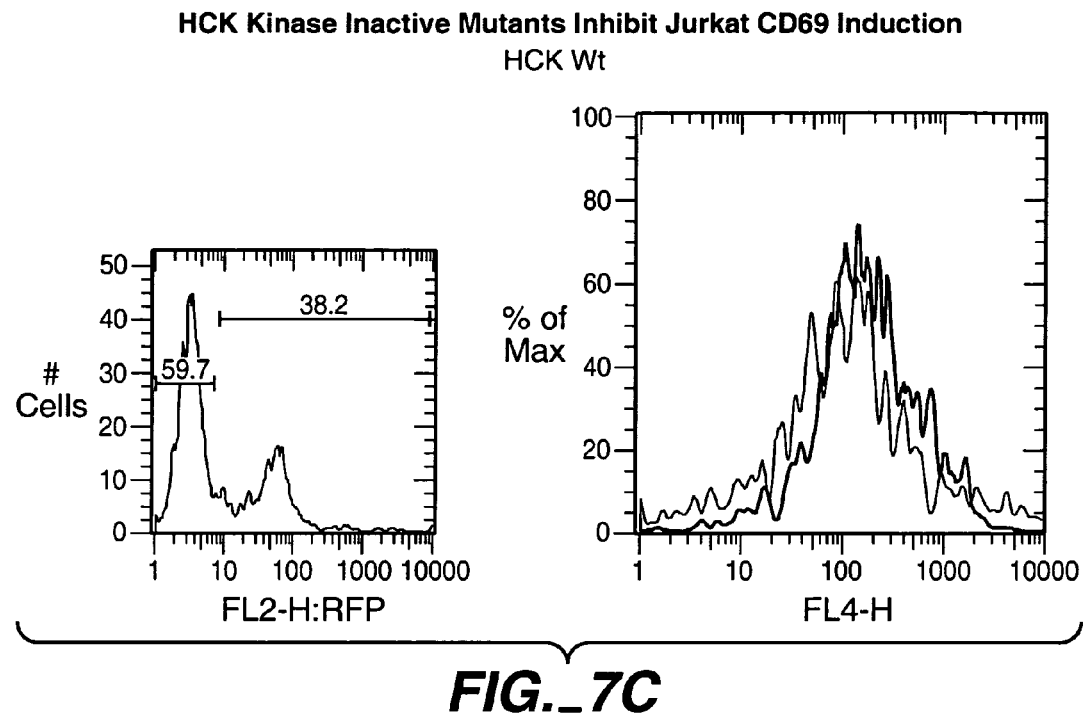
FIG._7C
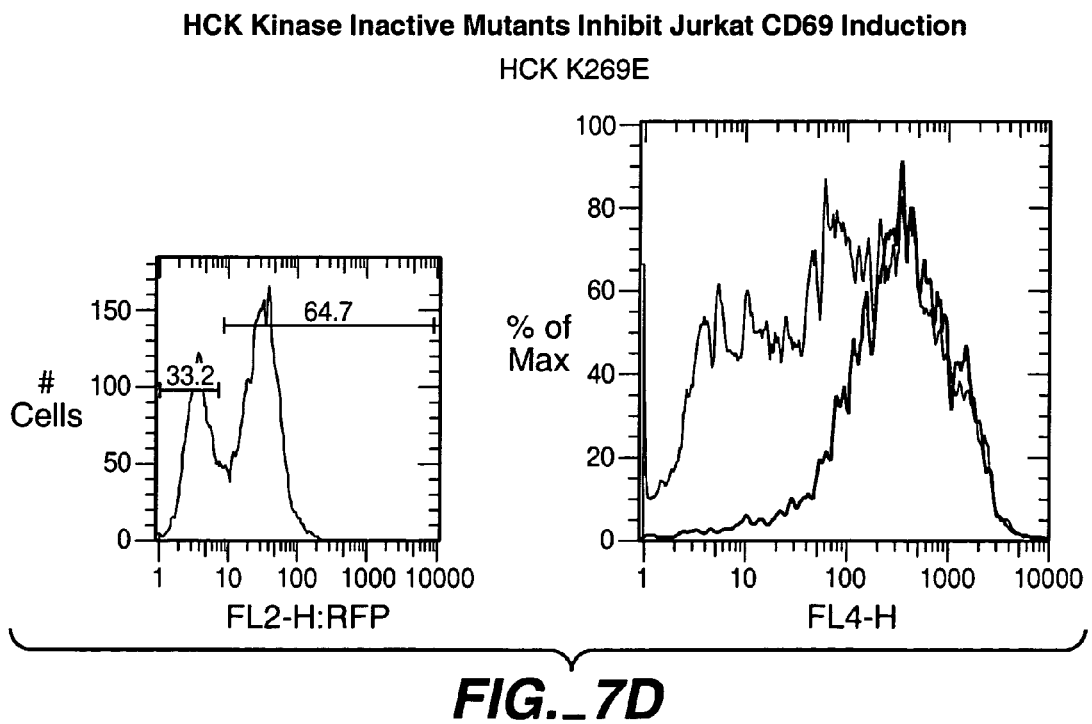
FIG._7D

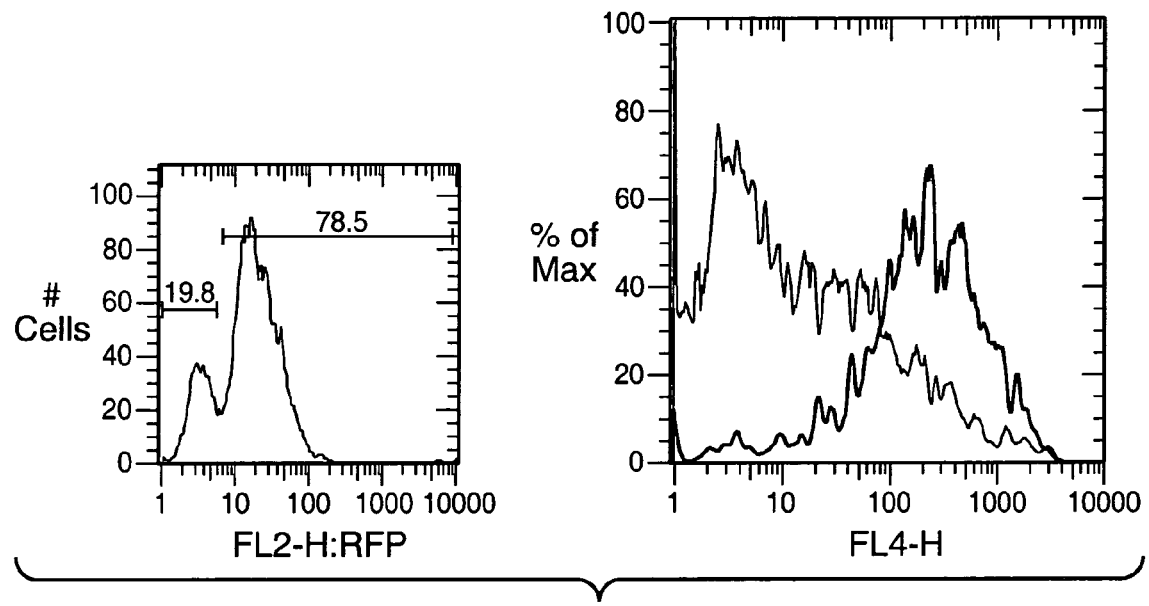
FIG._7E

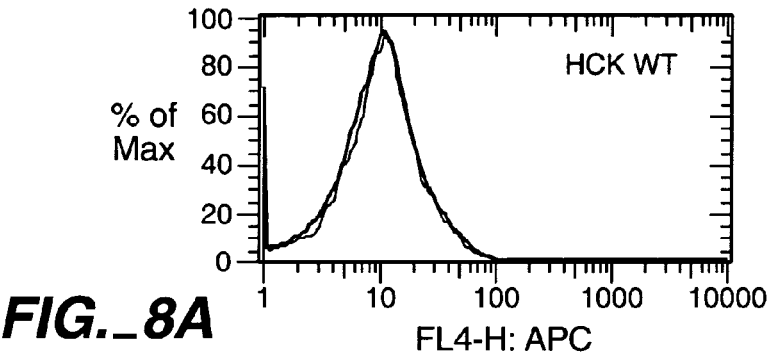
FIG._8A
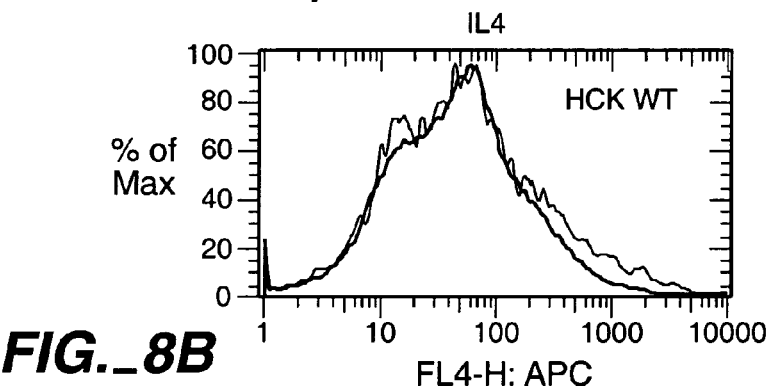
FIG._8B
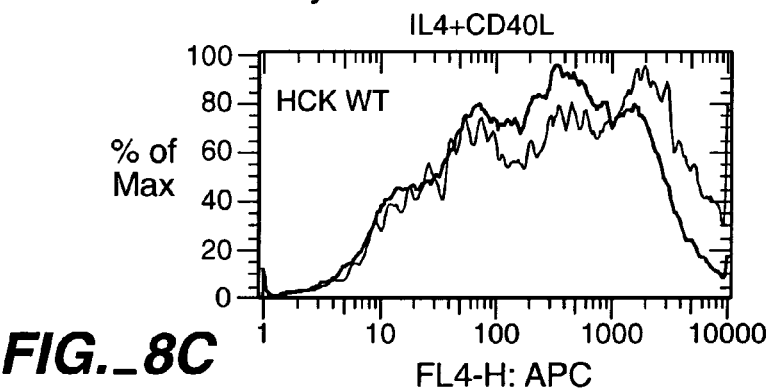
FIG._8C
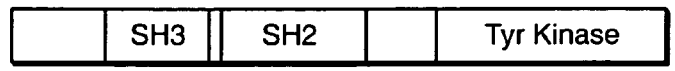
FIG._8D

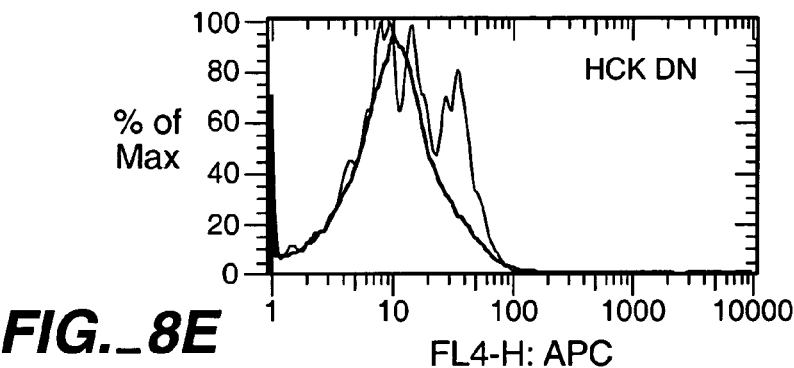
FIG._8E
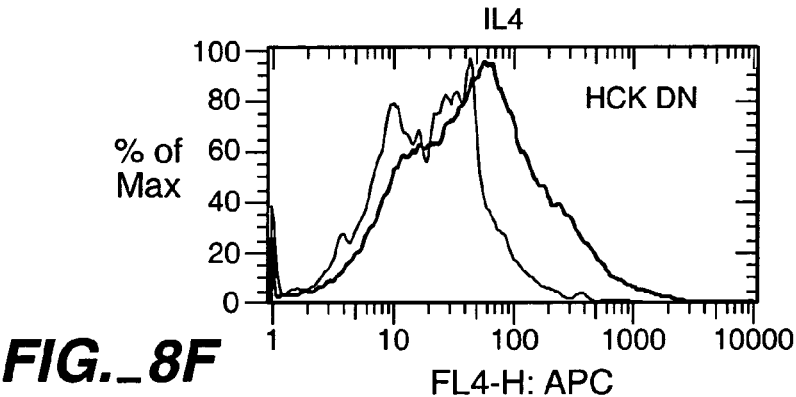
FIG._8F
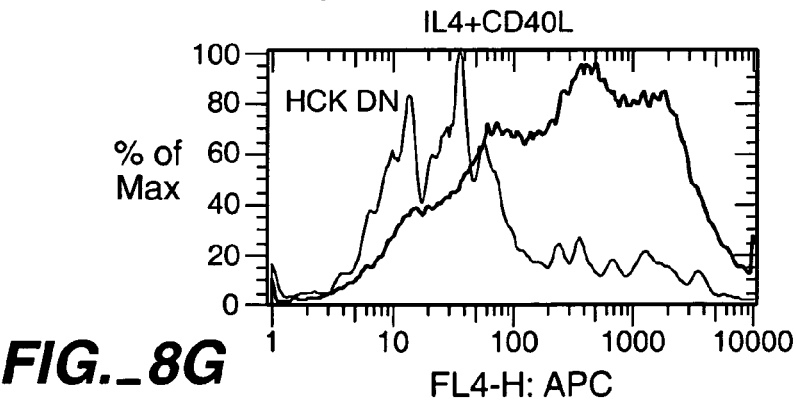
FIG._8G
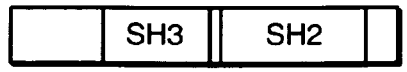
FIG._8H

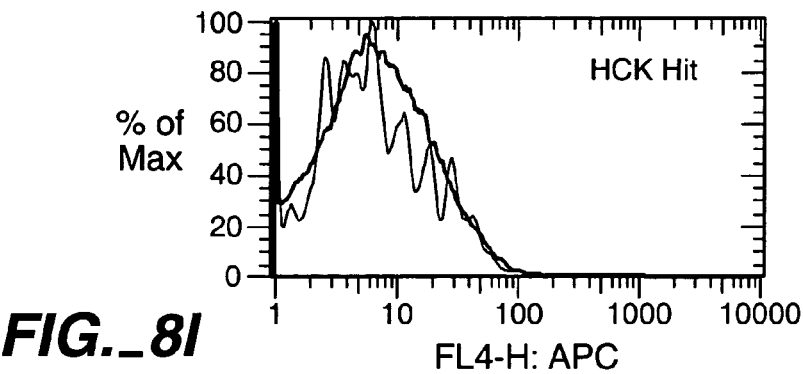
FIG._8I  HCK Mutants Inhibit Induced Expression of CD23 by IL4 and CD40L in Ramos Cells
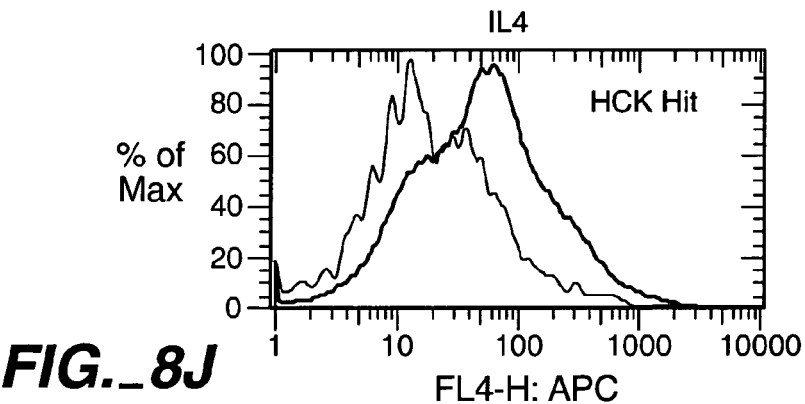
FIG._8J  HCK Mutants Inhibit Induced Expression of CD23 by IL4 and CD40L in Ramos Cells (IL4)
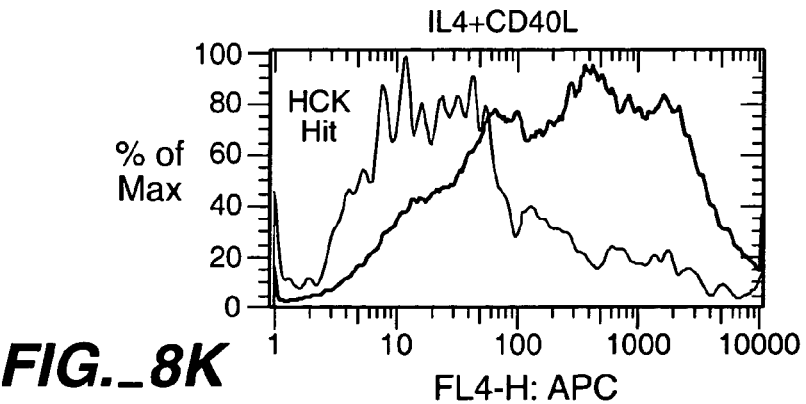
FIG._8K  HCK Mutants Inhibit Induced Expression of CD23 by IL4 and CD40L in Ramos Cells (IL4+CD40L)
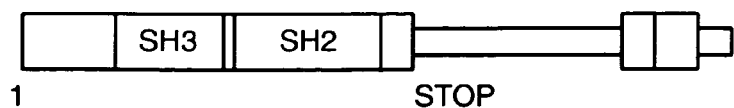
FIG._8L  HCK Hit

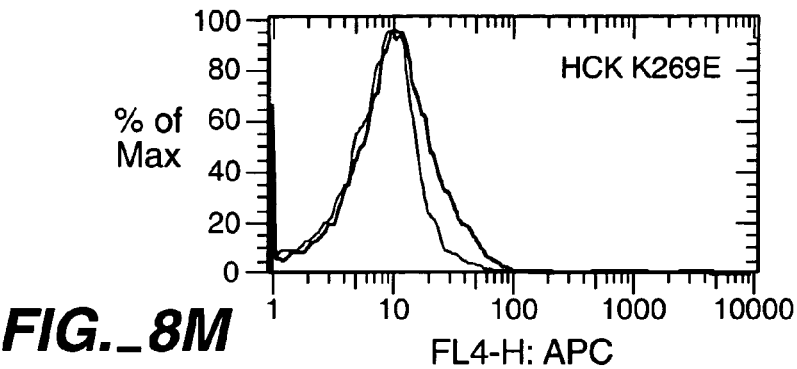
FIG._8M
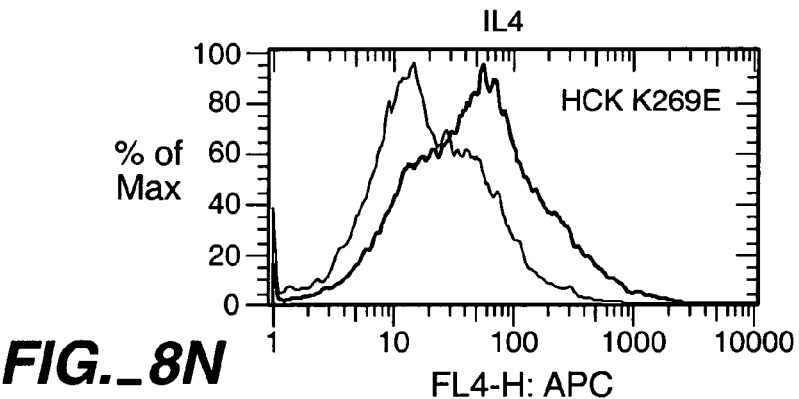
FIG._8N
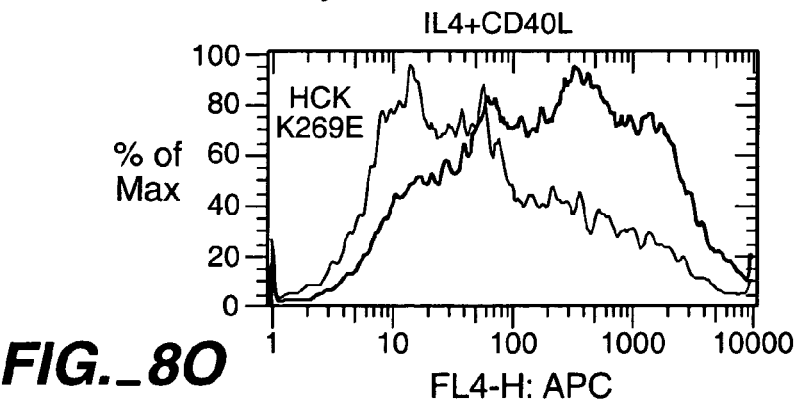
FIG._8O
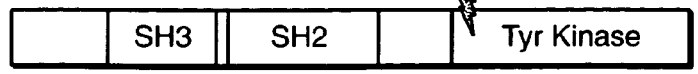
FIG._8P

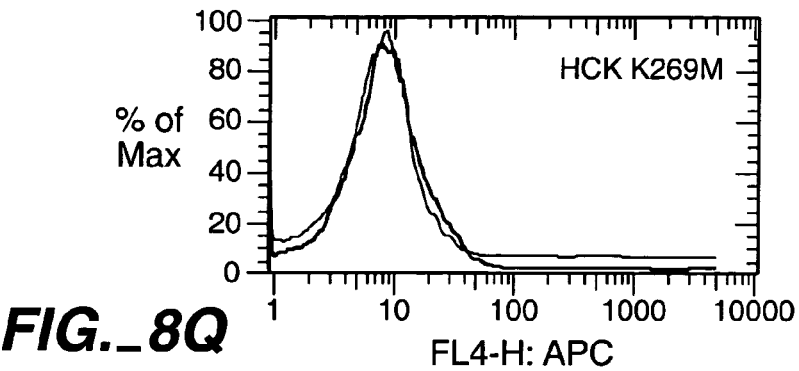
FIG._8Q HCK Mutants Inhibit Induced Expression of CD23 by IL4 and CD40L in Ramos Cells
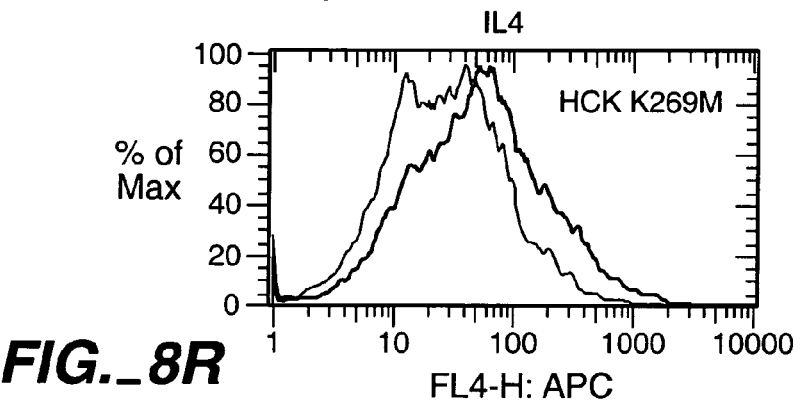
FIG._8R HCK Mutants Inhibit Induced Expression of CD23 by IL4 and CD40L in Ramos Cells (IL4)
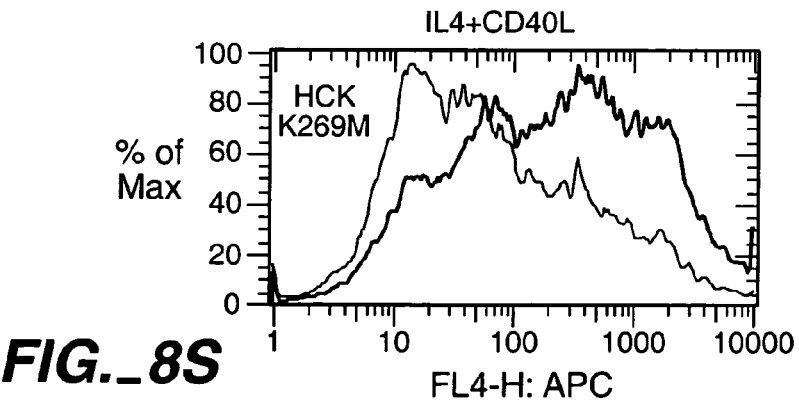
FIG._8S HCK Mutants Inhibit Induced Expression of CD23 by IL4 and CD40L in Ramos Cells (IL4+CD40L)
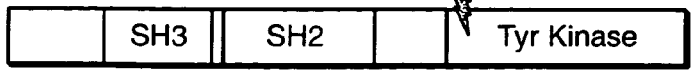
FIG._8T HCK Kinase Mutant K269M

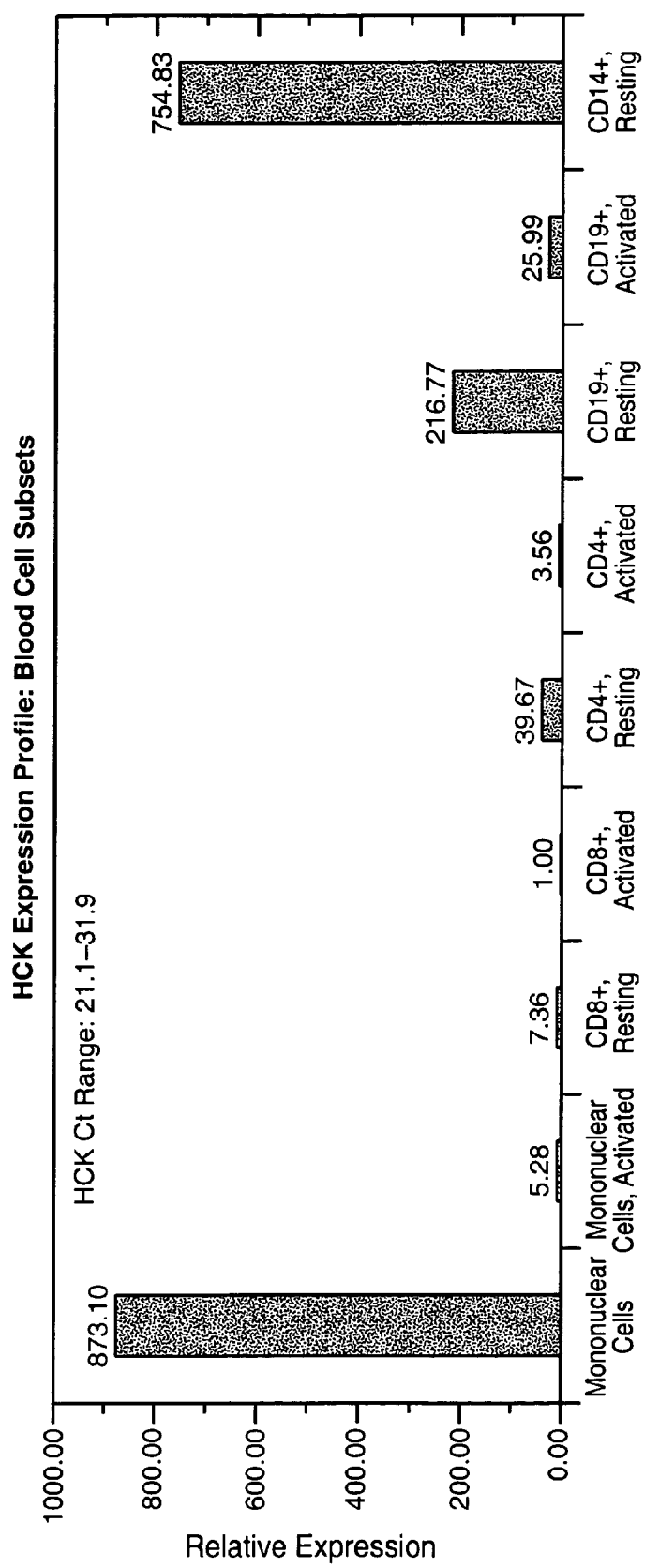
FIG._9A
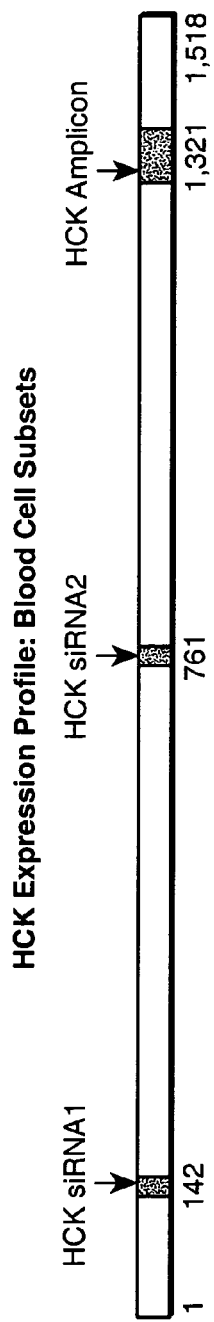
FIG._9B

MODULATORS OF LEUKOCYTE ACTIVATION, HCK COMPOSITIONS AND METHODS OF USE

FIELD OF THE INVENTION

The present invention relates to leukocyte activation and platelet proliferation, and provides nucleic acids and proteins which are capable of modulating leukocyte activation and platelet proliferation. The invention concerns disorders related to the dysfunction and dysregulation of leukocyte activation, as well as disorders related to the dysfunction and dysregulation of platelet proliferation. These disorders include autoimmune diseases, acute and chronic inflammatory diseases, lymphomas, leukemias, and Wiskott-Aldrich syndrome. The invention further concerns the immune response of a host receiving a transplant. The invention further concerns disorders related to the dysfunction or dysregulation of Hck.

BACKGROUND OF THE INVENTION

The immune response comprises a cellular response and a humoral response. The cellular response is mediated largely by T-lymphocytes (alternatively and equivalently referred to herein as T-cells), while the humoral response is mediated by B-lymphocytes (alternatively and equivalently referred to herein as B-cells).

B-cells produce and secrete antibodies in response to the presentation of antigen and MHC class II molecules on the surface of antigen presenting cells. Antigen presentation initiates B-cell activation with the engagement of the B-cell receptor (BCR) at the cell's surface. Following engagement, the BCR relays signals that are propagated through the cell's interior via signal transduction pathways. These signals lead to changes in B-cell gene expression and physiology, which underlie B-cell activation.

T-cells produce costimulatory molecules, including cytokines, that augment antibody production by B-cells during the humoral immune response. Cytokines also play a role in modulating the activity of T-cells themselves. Many T-cells act directly to engulf and destroy cells or agents that they recognize by virtue of the cell surface proteins they possess. The engagement of cell surface receptors on T-cells results in the propagation of intracellular signals that provoke changes in T-cell gene expression and physiology, which underlie the cellular immune response.

Antigen recognition alone is usually not sufficient to initiate a complete effector T- or B-cell response. The generation of many B-cell responses to antigen is dependent upon the interaction of B-cells with CD4+ helper T-cells directed against the same antigen. These helper T-cells express CD40L (CD154) which binds to the cell surface receptor, CD40, on resting B-cells. This interaction provides a critical activation signal to B-cells. Mutations in the CD40L lead to the X-linked immunodeficiency disorder hyper-IgM syndrome, which is characterized by low levels of IgA and IgG, normal to elevated levels of IgM, absence of germinal center formation, and decreased immune response. In addition, transgenic mice lacking CD40 exhibit reduced graft rejection. (Zanelli et al., Nature Medicine, 6: 629–630, 2000; Schonbeck et al., Cell Mol Life Sci, 58:4–43, 2001).

Non-lymphocyte myeloid derivatives are also activated by surface receptor engagement in immune response and in response to injury. For example, mast cells and basophils are activated by binding of antigen to surface IgE, while platelets are activated by the binding of thrombin to its receptor.

Intercellular communication between different types of lymphocytes, as well as between lymphocytes and non-lymphocytes in the normally functioning immune system is well known. Much of this communication is mediated by cytokines and their cognate receptors. Cytokine-induced signals begin at the cell surface with a cytokine receptor and are transmitted intracellularly via signal transduction pathways. Many types of cells produce cytokines, and cytokines can induce a variety of responses in a variety of cell types, including leukocytes. The response to a cytokine can be context-dependent as well as cell type specific.

Dysregulation of intercellular communication can perturb leukocyte activity and the regulation of immune responses. Such dysregulation is believed to underlie certain autoimmune disease states, hyper-immune states, and immune-compromised states. Such dysfunction may be cell autonomous or non-cell autonomous with respect to lymphocytes.

The activation of specific signaling pathways in leukocytes determines the quality, magnitude, and duration of immune responses. In response to transplantation, in acute and chronic inflammatory diseases, and in autoimmune responses, it is these pathways that are responsible for the induction, maintenance and exacerbation of undesirable leukocyte responses. Identification of these signaling pathways is desirable in order to provide diagnostic and prognostic tools, as well as therapeutic targets for modulating leukocyte function in a variety of disorders or abnormal physiological states. In addition, the ability to modulate these pathways and suppress normal immune responses is often desirable, for example in the treatment of hosts receiving a transplant.

While the extracellular domains and cognate ligands of lymphocyte receptors vary widely, many receptors have similar intracellular domains (such as the "immunoreceptor tyrosine-based activation motif" (ITAM)), and associate with common intracellular signaling molecules.

Tyrosine kinase activation is a critical event in the propagation of intracellular signals by many receptors on lymphocytes, including antigen receptors on B- and T-cells (for a review see Turner et al, Immunology Today, 21:148–154, 2000, incorporated herein in its entirety by reference).

With regard to the B-cell antigen receptor (BCR), the BCR is rapidly phosphorylated on tyrosine residues following engagement of the receptor by antigen or other crosslinking agents. This tyrosine phosphorylation leads to associations with several SH2-containing signaling proteins. SH2-containing proteins are known to bind to phosphorylated tyrosine residues in the context of specific amino acid sequences.

Many non-receptor tyrosine kinases have been shown to interact with tyrosine phosphorylated receptors in lymphocytes, including the antigen receptors of B- and T-cells. These non-receptor tyrosine kinases include members of the src family and the Bruton's tyrosine kinase (BTK) family. Importantly, many of these genes are associated with oncogenesis.

A non-receptor tyrosine kinase with an as yet undetermined role in lymphocytes is hematopoietic cell kinase (Hck). Hck is a tyrosine kinase comprising a consensus myristylation sequence, as well as SH2 and SH3 domains at the N-terminus, and a C-terminus tyrosine kinase domain possessing signature nucleotide-binding and catalytic tyrosine kinase domain motifs (Ziegler et al., Mol. Cell. Biol., 7:2276–2285, 1987; Quintrell et al., Mol. Cell. Biol., 7:2267–2275, 1987). Hck is highly expressed in cells of the myeloid lineage, particularly granulocytes. A role for Hck in the differentiation of these post-mitotic and short-lived cells has been suggested. In addition, chromosomal mapping of the Hck gene has implicated it in myeloid leukemias (Quintrell et al., supra).

HCK is also expressed in B cells, and is tyrosine phosphorylated in response to BCR stimulation. Further, in vitro kinase assays have demonstrated that HCK activity is increased in response to BCR stimulation. In addition HCK interacts with Bcr-abl, p120-Cbl, Btk, Ig-β and Ig-α, hBRAG, WASP and WIP, HIV Nef (in vitro) and the GP-130 chain of the IL-6 receptor (Zverkoczy et al., J. Biol. Chem., 275:20967–20979, 2000, and references therein; Scott et al., J. Biol. Chem., 277:28238–28246,2002 Brown et al., J. Virol., 73:9899–9907, 1999). In addition, WIP activates HCK, and WASP is an HCK substrate which is tyrosine phosphorylated by HCK.

In monocytes, Hck is upregulated and tyrosine phosphorylated in response to IL-2. Further, tyrosine kinase inhibitors inhibit Hck activation and the response of monocytes to IL-2 (Bosco et al., J. Immunol. 164:4575–4585, 2000). Hck is also responsive to CD38 and MHC II stimulation in monocytes (Zilber et al., Proc. Natl. Acad. Sci., 97:2840–5845, 2000 ).

In addition to kinases, phosphatases also play an important role in lymphocyte activation. Calcineurin is a calcium-sensitive protein serine/threonine phosphatase comprised of a catalytic and a regulatory subunit. Calcineurin is activated by the binding of Ca2+/calmodulin, and is inhibited by the immunosuppressants FK506 and cyclosporin A. Binding of cyclosporin to calcineurin blocks substrate access to the active site of the phosphatase (Liu et al., Cell, 66: 807, 1991).

The activation of calcineurin is an important regulatory step in lymphocyte activation. Calcineurin regulates phosphorylation of the nuclear factor in activated T-cells (NFAT) transcription factor, and thereby regulates nuclear import of NFAT and its ability to regulate transcription. The expression of many factors involved in lymphocyte activation, including cytokines (such as IL-2) and cell surface molecules (eg. CD40L) lies downstream of NFAT activation. (see Klee et al., J Biol Chem., 273:13367, 1998; Stankunas et al., Cold Spring Harbor Symposia Quant. Biol., 64: 505–516, 1999).

SUMMARY OF THE INVENTION

The present invention provides compositions and methods for modulating leukocyte and platelet activation. Compositions and methods for the treatment of disorders related to leukocyte and platelet dysfunction and dysregulation are also provided. Prophylactics and methods for the prevention of such disorders are also provided. Also provided are compositions and methods for the diagnostic and prognostic determination of such disorders. Further provided are assays for the identification of bioactive agents capable of modulating leukocyte and platelet activation.

Accordingly, in one aspect, the invention provides Hck nucleic acids which are capable of modulating leukocyte and platelet activation. In another aspect, the invention provides Hck proteins capable of modulating leukocyte and platelet activation.

In a preferred embodiment, the invention provides Hck nucleic acids which encode Hck proteins.

In a preferred embodiment, an Hck protein provided herein is capable of binding to an Hck binding partner selected from the group consisting of Nef, WASP, WIP, gp130, CD44, CD4, IL-2R, Btk, Bcr-abl, Ras-GAP, hBRAG, Ig-α, Ig-β, and p120Cbl.

In a preferred embodiment, an Hck protein provided herein is capable of modulating T-cell receptor (TCR)-induced expression of CD69.

In a preferred embodiment, an Hck protein provided herein is capable of modulating BCR-induced activation of the immunoglobulin heavy chain gene (IgH) promoter.

In a preferred embodiment, an Hck protein provided herein is capable of modulating BCR-induced immunoglobulin production.

In a preferred embodiment, an Hck protein provided herein is capable of reducing basal surface IgM expression in lymphocytes.

In a preferred embodiment, an Hck protein provided herein is capable of inhibiting CD23 induction by CD40L, IL-4, or the combination of CD40L and IL-4, in lymphocytes.

In a preferred embodiment, an Hck protein provided herein is capable of inhibiting BCR-induced calcium flux in B-lymphocytes.

The present invention also provides isolated polypeptides which specifically bind to an Hck protein. In one embodiment, the polypeptide is an antibody. In a preferred embodiment, the polypeptide is a monoclonal antibody. In a preferred embodiment, the monoclonal antibody is capable of reducing or eliminating the activity of Hck.

Also provided herein are methods of screening for a bioactive agent capable of binding to an Hck protein. The methods comprise combining an Hck protein and a candidate bioactive agent and determining the binding of candidate agent to Hck protein. In one embodiment, the method involves identifying the candidate agent.

Also provided herein are methods of screening for a bioactive agent capable of interfering with the binding of an Hck protein. The methods comprise combining a candidate bioactive agent, an Hck protein, and an Hck binding partner which will bind to Hck in the absence of candidate agent, and determining the binding of Hck to binding partner in the presence of candidate bioactive agent. In preferred embodiments, the Hck binding partner is selected from the group consisting of Nef, WASP, WIP, gp130, CD44, CD4, IL-2R, Btk, Bcr-abl, Ras-GAP, hBRAG, Ig-α, Ig-β, and p120Cbl. In a preferred embodiment, the method involves determining the binding of Hck to binding partner in the presence and absence of candidate bioactive agent. In one embodiment, Hck and Hck binding partner are combined first. In one embodiment, the method involves identifying the candidate agent.

Also provided herein are methods of screening for a bioactive agent capable of increasing the binding of an Hck protein. In one aspect, the method comprises combining a candidate bioactive agent, an Hck protein, and an Hck binding partner which will bind to Hck in the absence of candidate agent, and determining the binding of Hck to binding partner in the presence of candidate bioactive agent. In preferred embodiments, the Hck binding partner is selected from the group consisting of Nef, WASP, WIP, gp130, CD44, CD4, IL-2R, Btk, Bcr-abl, Ras-GAP, hBRAG, Ig-α, Ig-β, and p120Cbl. In a preferred embodiment, the method involves determining the binding of Hck to binding partner in the presence and absence of candidate bioactive agent. In one embodiment, Hck and Hck binding partner are combined first. In one embodiment, the method involves identifying the candidate agent.

Also provided herein are methods for screening for a bioactive agent capable of modulating the activity of an Hck protein. In one aspect, the method comprises contacting a candidate bioactive agent to a cell comprising a recombinant Hck nucleic acid and expressing an Hck protein. In one aspect, the method comprises contacting a library of candidate bioactive agents to a plurality of cells comprising a recombinant Hck nucleic acid and expressing an Hck protein. In one embodiment, the method involves determining the kinase activity of Hck protein. In one embodiment, the method involves determining the phosphorylation of an Hck substrate protein. In one embodiment, the method involves determining the tyrosine phosphorylation of Hck. In one embodiment, the method involves determining the binding of Hck to an Hck binding partner.

Also provided herein are methods of screening for a bioactive agent capable of modulating lymphocyte activation.

In a preferred embodiment, the methods comprise determining the ability of a candidate agent to bind to Hck.

In a preferred embodiment, the methods comprise detecting binding of candidate agent to Hck protein, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Preferred Hck proteins for use in these methods comprise an SH2 and an SH3 domain but lack a tyrosine kinase domain. In an especially preferred embodiment, Hck proteins used consist essentially of the amino acid sequence set forth by residues 1–211, 1–230, or 61–211 in SEQ ID NO:2.

In another preferred embodiment, a full length Hck protein comprising SH2, SH3, and tyrosine kinase domains, and preferably comprising the amino acid sequence set forth in SEQ ID NO:2, is used.

Bioactive agents that inhibit lymphocyte activation in these assays are useful as immunosuppressants.

By immunosuppressant is meant an agent that suppresses the body's ability to react to an antigen.

In another preferred embodiment, the methods comprise determining the ability of a candidate agent to modulate the binding of Hck to an Hck binding partner.

In a preferred embodiment, the methods comprise detecting inhibition of the binding of Hck protein to an Hck binding partner in the presence of candidate agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Preferred Hck proteins for use in these methods comprise an SH2 domain and an SH3 domain but lack a tyrosine kinase domain. In an especially preferred embodiment, Hck proteins used consist essentially of the amino acid sequence set forth by residues 1–211, 1–230, or 61–211 in SEQ ID NO:2.

In another preferred embodiment, a full length Hck protein comprising SH2, SH3 and tyrosine kinase domains, and preferably comprising the amino acid sequence set forth in SEQ ID NO:2, is used.

Bioactive agents that inhibit lymphocyte activation in these assays are useful as immunosuppressants.

In another preferred embodiment, the methods comprise determining the ability of a candidate bioactive agent to modulate the activity of an Hck protein.

In a preferred embodiment, the methods comprise detecting a decrease in the kinase activity of Hck in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Preferred Hck proteins for use in these methods consist essentially of a kinase domain. In an especially preferred embodiment, Hck proteins used consist essentially of the amino acid sequence set forth by residues 241–490, 241–505, or 230–505 in SEQ ID NO:2.

In another preferred embodiment, a full length Hck protein comprising an SH2 domain, an SH3 domain, and preferably comprising the amino acid sequence set forth in SEQ ID NO:2, is used.

Bioactive agents that inhibit lymphocyte activation in these assays are useful as immunosuppressants.

In a preferred embodiment, candidate bioactive agents used in these assays are small molecule chemical compounds, from about 100 to about 1500, more preferably about 100 to about 1200, more preferably about 100 to about 1000 more preferably about 200 to about 500 daltons.

In a preferred embodiment, a library of candidate bioactive agents is contacted to isolated or cell-free Hck protein.

In a preferred embodiment, determining lymphocyte activation in the methods herein comprises determining the level of expression of a surface marker which is associated with activation of the lymphocyte, in the presence of candidate agent. In a preferred embodiment, the surface marker is selected from the group consisting of CD40L, CD23, CD69, CD80 and CD86. In an especially preferred embodiment, the surface marker is CD69 or CD23.

In another preferred embodiment, determining lymphocyte activation in the methods herein comprises determining the level of activity of a promoter in the presence of candidate agent, which activity correlates with lymphocyte activation in the absence of candidate agent. In a preferred embodiment the promoter is an NFAT-responsive promoter, such as the IL-2 promoter. In another preferred embodiment, the promoter is the immunoglobulin heavy chain gene promoter.

In a preferred embodiment, determining lymphocyte activation involves sorting lymphocytes by FACS. Sorting may be done based on the level of expression of a surface marker which normally correlates with lymphocyte activation, or may be done based on the level of activity of a promoter which normally correlates with lymphocyte activation, or based on other criteria discussed herein.

Also provided herein are methods for inhibiting immunoglobulin production in a B cell. In one embodiment, the methods comprise introducing into a B cell an immunosuppressant identified by the methods provided herein. In one embodiment, the methods comprise introducing into a B cell an Hck antagonist. In a preferred embodiment, the Hck antagonist is an Hck antisense nucleic acid. In another preferred embodiment, the Hck antagonist is an Hck RNAi nucleic acid. In another preferred embodiment, the Hck antagonist is an intrabody that specifically binds to HCK and reduces or eliminates HCK bioactivity.

Also provided herein are methods for modulating lymphocyte activation in a patient having a lymphocyte activation disorder, comprising administering to a patient having a lymphocyte activation disorder a medicament comprising an antagonist of HCK protein activity.

Also provided herein are methods for inhibiting B cell and T cell activation in a patient having an autoimmune disease, comprising administering to a patient having an autoimmune disease a medicament comprising an HCK antagonist.

Also provided herein are methods for inhibiting B cell and T cell activation in a patient having an autoimmune disease, comprising administering to a patient having an autoimmune disease a medicament comprising an immunosuppressant obtained by the screening methods provided herein.

Also provided herein are methods for inhibiting immunoglobulin production in a patient having an autoimmune disease, comprising administering to a patient having an autoimmune disease a medicament comprising an Hck antagonist.

Also provided herein are methods for inhibiting immunoglobulin production in a patient having an autoimmune disease, comprising administering to a patient having an autoimmune disease a medicament comprising an immunosuppressant identified by the methods provided herein.

Also provided herein are methods for prolonging the survival of a graft in a mammalian host, comprising administering to a mammalian host receiving a graft a medicament comprising an HCK antagonist.

Also provided herein are methods for prolonging the survival of a graft in a mammalian host, comprising administering to a mammalian host receiving a graft a medicament comprising an immunosuppressant identified by the methods provided herein.

In a preferred embodiment, provided herein are small molecule chemical compositions useful for the prevention and treatment of acute inflammatory disorders, chronic inflammatory disorders, autoimmune disorders, and transplant rejection.

BRIEF DESCRIPTION OF THE DRAWINGS

FIG. 1 shows nucleotide sequence of human Hck, SEQ ID NO:1.

FIG. 2 shows amino acid sequence of human Hck, SEQ ID NO:2.

FIG. 4 shows results from experiments in which Hck mutants are expressed in the BJAB cell line, and BCR-induced IgH promoter activity (as reported by GFP expression) is measured. The results demonstrate that Hck mutants inhibit BCR-induced IgH promoter activity. Also shown are results from experiments in which Hck mutants are expressed in the BJAB cell line, or the Jurkat (T-cell) cell line, and BCR-induced or TCR-induced CD69 expression is measured. The results show that Hck mutant inhibit BCR-induced and TCR-induced CD69 expression in BJAB and Jurkat cells, respectively.

FIG. 5 shows results from experiments in which full length Hck or Hck mutants are expressed in the BJAB cell line, and BCR-induced IgH activity (as reported by GFP expression) is measured. The results show that overexpression of full length Hck has no effect on BCR-induced IgH promoter activity, while Hck mutants inhibit BCR-induced IgH promoter activity.

FIG. 6 is a table of human autoimmune diseases.

FIG. 7 shows the results from experiments in which full length Hck (wt), Hck truncation mutants (hit and DN) and Hck kinase-dead point mutants were expressed in Jurkat cells, and their effect on CD69 induction by C305 antibody (anti-TCR) was assessed. The results show that Hck truncation mutants and kinase-dead point mutants inhibit CD69 induction in Jurkat cells, while overexpression of wildtype Hck has no effect.

FIG. 8 shows the results from experiments in which full length Hck (wt), Hck truncation mutants (hit and DN) and Hck kinase-dead point mutants were expressed in Ramos cells, and their effect on CD23 expression induced by IL-4 or IL-4 and CD40L was assessed. The results show that Hck truncation mutants and kinase-dead point mutants inhibit CD23 induction in Ramos cells, while overexpression of wildtype Hck has no effect.

FIG. 9 shows an Hck expression profile in blood cell subsets which are resting or activated.

DETAILED DESCRIPTION OF THE INVENTION

Figure 3C:
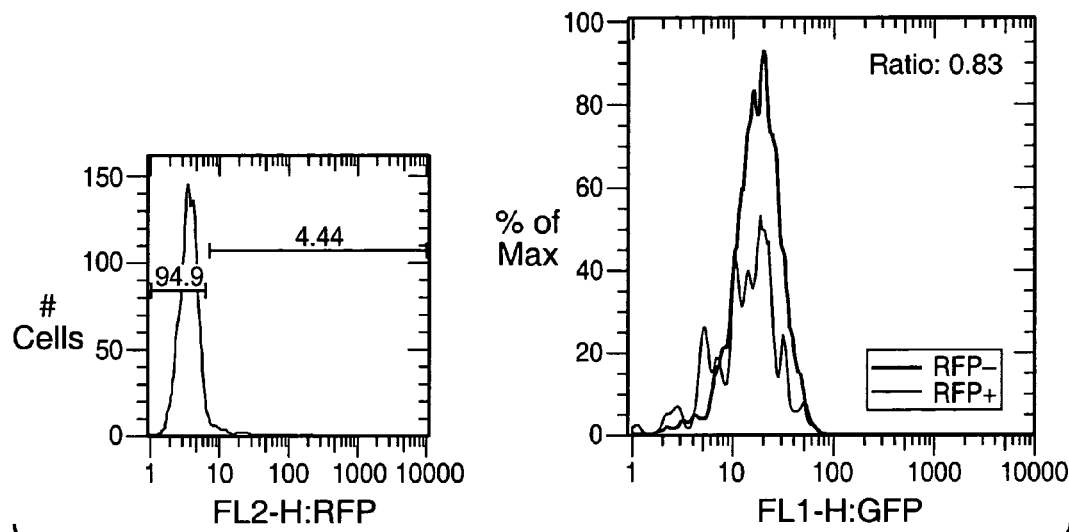
FIG. 3 structurally aligns two Hck dominant negative mutants with full length Hck, depicting the domains present and absent in each. The figure also shows results from experiments in which Hck mutants are expressed in the BJAB (B-cell) cell line, and BCR-induced IgH promoter activity (as reported by GFP expression) is measured. The results demonstrate that Hck mutants inhibit BCR-induced IgH promoter activity.
Figure 3D:
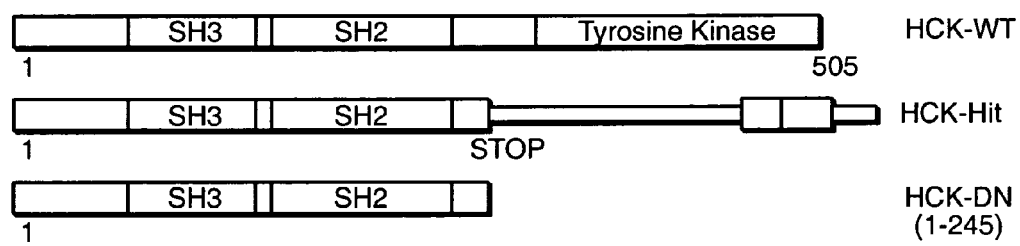

The present invention provides compositions and methods for modulating leukocyte and platelet activation. Compositions and methods for the treatment of disorders related to the dysfunction and dysregulation of leukocyte and platelet activation are also provided. Prophylactics and methods for the prevention of such disorders are also provided. Also provided are compositions and methods for the diagnostic and prognostic determination of such disorders. Further provided are assays for the identification of bioactive agents capable of modulating leukocyte and platelet activation.

In accordance with these objectives, in one aspect, the present invention provides Hck nucleic acids which are capable of modulating leukocyte and platelet activation. Also in accordance with these objectives, in another aspect, the invention provides Hck proteins capable of modulating leukocyte and platelet activation.

An Hck protein of the present invention may be identified in several ways. "Protein" in this sense includes proteins, polypeptides, and peptides. An Hck protein may be identified by its ability to bind to Hck binding partners as described herein. An Hck protein may be identified by its homology to src-like non-receptor tyrosine kinases. An Hck protein may be identified by the presence of a tyrosine kinase domain, an SH2 domain, an SH3 domain, or an N-terminal myristylation sequence, or any combination thereof. An Hck protein may also be identified by possession of tyrosine kinase activity.

An Hck protein may also be identified by its responsiveness to II-6, IL-2, or BCR stimulation in lymphocytes. An Hck protein may also be identified by its amino acid sequence identity or similarity to SEQ ID NO:2, or by the sequence identity or similarity of its encoding nucleic acid to SEQ ID NO:1.

Hck nucleic acids and proteins may initially be identified by sequence identity or similarity to SEQ ID NOs: 1 and 2, as further described below. In a preferred embodiment, Hck nucleic acids and Hck proteins have sequence identity or similarity to the sequences provided herein and one or more Hck bioactivities described herein. Such sequence identity or similarity can be based upon the overall nucleic acid or amino acid sequence.

In a preferred embodiment, an Hck protein provided herein comprises an amino acid sequence having at least about 85%, more preferably at least about 90%, more preferably at least about 95%, more preferably at least about 98% identity to the amino acid sequence set forth in SEQ ID NO:2. In a preferred embodiment, the Hck protein comprises the amino acid sequence set forth in SEQ ID NO:2. Preferably, the Hck protein also possesses one or more Hck bioactivities described herein.

Fragments are included in the definition of Hck proteins. In a preferred embodiment, an Hck protein provided herein comprises an amino acid sequence having at least about 85%, more preferably at least about 90%, more preferably at least about 95%, more preferably at least about 98% identity to a portion of the amino acid sequence set forth in SEQ ID NO:2. In an especially preferred embodiment, the Hck protein comprises a portion of the amino acid sequence set forth in SEQ ID NO:2. Portion, or fragment, in this sense includes sequences from at least 2 amino acids up to the full length sequence in SEQ ID NO:2 minus one amino acid at either the N- or C-terminus.

In a preferred embodiment, an Hck protein provided herein comprises a tyrosine kinase domain and lacks SH2 and SH3 domains. In a preferred embodiment, such an Hck protein comprises an amino acid sequence having at least about 85%, more preferably at least about 90%, more preferably at least about 95%, more preferably at least about 98% identity to the amino acid sequence set forth by residues 241–490, 241–505, or 230–505 in SEQ ID NO:2. In an especially preferred embodiment, the Hck protein comprises the amino acid sequence set forth by residues 241–490, 241–505, or 230–505 in SEQ ID NO:2.

SH2 domains are well known in the art. For example, see Pawson, Nature 373:573–580, 1995; Pawson et al., Cell, 71:359–362, 1992; Pawson, Adv. Cancer Res., 64:87–110, 1994. SH2 domains comprise signature polypeptide sequences by which they may be initially recognized, as is known by those in the art. SH2 domains mediate protein-protein interactions by binding to specific polypeptide sequences comprising phosphorylated tyrosine residues in a consensus SH2-binding domain.

SH3 domains are well known in the art. For example, see Pawson, Nature 373:573–580, 1995; Pawson et al., Cell, 71:359–362, 1992; Pawson, Adv. Cancer Res., 64:87–110, 1994. SH3 domains comprise signature polypeptide sequences by which they may be initially recognized, as is known by those in the art. SH3 domains mediate protein-protein interactions by binding to specific polypeptide sequences comprising histidine rich motifs in a consensus SH3-binding domain.

Tyrosine kinase domains are well known in the art. For example, see Ulrich et al., Cell, 61:203–212, 1990; Weiss et al., Cell, 94:277–280, 1998; Schlessinger, Cell, 103:211–225, 2000; Hubbard et al., J. Biol Chem., 273:11987–11990, 1998; Hanks et al., Science, 241:42–52, 1991. Tyrosine kinase domains comprise signature polypeptide sequences by which they may be initially recognized, as is known by those in the art. Tyrosine kinase domains possess an ATP-binding motif as well as a conserved lysine residue within the catalytic region which catalyzes the phosphorylation of substrate proteins. Mutation of the conserved lysine residue typically alters kinase activity.

Myristylation sequences are well known in the art. For example, see Resh, Cell, 76:411–413, 1994; Kaplan et al., Mol. Cell Biol., 8:2435–2441, 1988. Myristylation sequences are located the N-terminus of a polypeptide, and target the polypeptide for post-translational myristylation. This post-translational modification is involved in targeting a number of proteins to the plasma membrane and is often required for protein activation.

In a preferred embodiment, an Hck protein provided herein consists essentially of a tyrosine kinase domain. In a preferred embodiment, such an Hck protein consists essentially of an amino acid sequence having at least about 85%, more preferably at least about 90%, more preferably at least about 95%, more preferably at least about 98% identity to the amino acid sequence set forth by residues 241–490, 241–505, or 230–505 in SEQ ID NO:2. In an especially preferred embodiment, the Hck protein consists essentially of the amino acid sequence set forth by residues 241–490, 241–505, or 230–505 in SEQ ID NO:2.

In a preferred embodiment, an Hck protein provided herein comprises an SH2 domain and an SH3 domain, and lacks a tyrosine kinase domain. In a preferred embodiment, such an Hck protein comprises an amino acid sequence having at least about 85%, more preferably at least about 90%, more preferably at least about 95%, more preferably at least about 98% identity to the amino acid sequence set forth by residues 1–211, 1–230, or 62–211 in SEQ ID NO:2. In an especially preferred embodiment, the Hck protein comprises the amino acid sequence set forth by residues 1–211, 1–230, or 62–211 in SEQ ID NO:2.

In another preferred embodiment, an Hck protein provided herein consists essentially of an SH2 domain and an SH3 domain, and lacks a tyrosine kinase domain. In a preferred embodiment, such an Hck protein consists essentially of an amino acid sequence having at least about 85%, more preferably at least about 90%, more preferably at least about 95%, more preferably at least about 98% identity to the amino acid sequence set forth by residues 1–211, 1–230, or 62–211 in SEQ ID NO:2. In an especially preferred embodiment, the Hck protein consists essentially of the amino acid sequence set forth by residues 1–211, 1–230, or 62–211 in SEQ ID NO:2.

In a preferred embodiment, an Hck protein provided herein lacks a tyrosine kinase domain and comprises an amino acid sequence having at least about 85%, more preferably at least about 90%, more preferably at least about 95%, more preferably at least about 98% identity to the amino acid sequence set forth by residues 1–230 or 1–245 in SEQ ID NO:2. In an especially preferred embodiment, the Hck protein comprises the amino acid sequence set forth by residues 1–230 or 1–245 in SEQ ID NO:2.

In yet another preferred embodiment, an Hck protein provided herein lacks a tyrosine kinase domain and consists essentially of an amino acid sequence having at least about 85%, more preferably at least about 90%, more preferably at least about 95%, more preferably at least about 98% identity to the amino acid sequence set forth by residues 1–230 or 1–245 in SEQ ID NO:2. In an especially preferred embodiment, the Hck protein consists essentially of the amino acid sequence set forth by residues 1–230 or 1–245 in SEQ ID NO:2.

In a preferred embodiment, an Hck protein provided herein comprises an inactive tyrosine kinase domain which lacks a catalytic lysine residue within the tyrosine kinase domain, and comprises an amino acid sequence having at least about 85%, more preferably at least about 90%, more preferably at least about 95%, more preferably at least about 98% identity to the amino acid sequence set forth by SEQ ID NO:2. In one embodiment, an Hck protein comprising a point mutation at the lysine residue within the consensus tyrosine kinase domain is provided. In an especially preferred embodiment, the Hck protein comprises a point mutation in catalytic lysine residue corresponding to K269 in SEQ ID NO:2. In an especially preferred embodiment, the invention provides kinase-dead Hck point mutants comprising SEQ ID NO:2 except for point mutations at K269. Particularly preferred are point mutants K269M and K269E.

In one aspect, the present invention provides Hck nucleic acids, including Hck nucleic acids encoding Hck proteins.

In the case of an Hck nucleic acid encoding an Hck protein, the overall sequence identity of the nucleic acid sequence is commensurate with amino acid sequence identity, but takes into account the degeneracy in the genetic code and codon bias of different organisms. Accordingly, the nucleic acid sequence identity may be either lower or higher than that of the protein sequence. The nucleotide sequence set forth in SEQ ID NO:1 is that of human Hck nucleic acid. An Hck nucleic acid of the present invention comprises a nucleic acid sequence that preferably has greater than about 75% identity to the nucleic acid sequence set forth in SEQ ID NO:1, more preferably greater than about 80%, particularly greater than about 85% and most preferably greater than 90%. In some embodiments the sequence identity will be as high as about 93 to 95 or 98%.

In a preferred embodiment, the invention provides Hck nucleic acids having at least about 75%, more preferably 80%, more preferably 85%, more preferably 90%, more preferably 95%, more preferably 98% identity to the sequence set forth by nucleotides 78–1595 in SEQ ID NO:1. In a preferred embodiment, the Hck nucleic acid comprises nucleotides 78–1595 in SEQ ID NO:1.

In a preferred embodiment, the invention provides Hck nucleic acids having at least about 75%, more preferably 80%, more preferably 85%, more preferably 90%, more preferably 95%, more preferably 98% identity to the sequence set forth by nucleotides 78–767 in SEQ ID NO:1. In a preferred embodiment, the Hck nucleic acid comprises nucleotides 78–767 in SEQ ID NO:1.

Also provided herein are Hck proteins encoded by such Hck nucleic acids.

In a preferred embodiment, an Hck nucleic acid encodes an Hck protein. As will be appreciated by those in the art, due to the degeneracy of the genetic code, an extremely large number of nucleic acids may be made, all of which encode the Hck proteins of the present invention. Thus, having identified a particular amino acid sequence, those skilled in the art could make any number of different nucleic acids encoding the same by simply modifying the sequence of one or more codons in a way which does not change the amino acid sequence of the encoded Hck protein.

In a preferred embodiment, an Hck nucleic acid encodes an Hck protein comprising an amino acid sequence having at least about 85%, more preferably at least about 90%, more preferably at least about 95%, more preferably at least about 98% identity to the amino acid sequence set forth in SEQ ID NO:2.

In an especially preferred embodiment, an Hck nucleic acid provided herein encodes an Hck protein comprising the amino acid sequence set forth in SEQ ID NO:2.

In one embodiment, the Hck nucleic acid is determined through hybridization studies. Thus, for example, nucleic acids which hybridize under high stringency conditions to the nucleic acid sequences shown in SEQ ID NO:1 or their complements, or fragments thereof or their complements, are considered Hck nucleic acids. High stringency conditions are known in the art; see for example Maniatis et al., Molecular Cloning: A Laboratory Manual, 2d Edition, 1989, and Short Protocols in Molecular Biology, ed. Ausubel, et al., both of which are hereby incorporated by reference. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Acid Probes, "Overview of principles of hybridization and the strategy of nucleic acid assays" (1993). Generally, stringent conditions are selected to be about 5–10° C. lower than the thermal melting point ($T_m$) for the specific sequence at a defined ionic strength pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 sodium ion, typically about 0.01 to 1.0 M sodium ion concentration (or other salts) at pH 7.0 to 8.3 and the temperature is at least about 30° C. for short probes (e.g. 10 to 50 nucleotides) and at least about 60° C. for long probes (e.g. greater than 50 nucleotides). Stringent conditions may also be achieved with the addition of destabilizing agents such as formamide.

In another embodiment, less stringent hybridization conditions are used; for example, moderate or low stringency conditions may be used, as are known in the art; see Molecular Cloning, A Laboratory Manual, Sambrook et al., *Molecular Cloning, A Laboratory Manual,* 3rd edition, 2001, Cold Spring Harbor Press, Cold Spring Harbor, N.Y.; and Tijssen, supra.

Also provided herein are Hck antisense nucleic acids which will hybridize under high stringency conditions to an Hck nucleic acid comprising the nucleic acid sequence set forth in SEQ ID NO:1. In a preferred embodiment, the Hck antisense nucleic acid inhibits the expression of Hck protein. In a preferred embodiment, the Hck antisense nucleic acid inhibits Hck protein activity. In a preferred embodiment, the Hck antisense nucleic acid has at least one activity possessed by a dominant negative Hck protein described herein. Preferably, the Hck antisense nucleic acids comprises a nucleotide sequence complementary to a portion of the sequence set forth in SEQ ID NO:1.

As is known in the art, a number of different programs can be used to identify whether a protein or nucleic acid has sequence identity or similarity to a known sequence. Sequence identity and/or similarity is determined using standard techniques known in the art, including, but not limited to, the local sequence identity algorithm of Smith & Waterman, Adv. Appl. Math. 2:482 (1981), by the sequence identity alignment algorithm of Needleman & Wunsch, J. Mol. Biool. 48:443 (1970), by the search for similarity method of Pearson & Lipman, PNAS USA 85:2444 (1988), by computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., *Nucl. Acid Res.* 12:387–395 (1984), preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127–149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, J. Mol. Evol. 35:351–360 (1987); the method is similar to that described by Higgins & Sharp CABIOS 5:151–153 (1989). Useful PILEUP parameters including a default gap weight of 3.00, a default gap length weight of 0.10, and weighted end gaps.

Another example of a useful algorithm is the BLAST algorithm, described in Altschul et al., J. Mol. Biol. 215, 403–410, (1990) and Karlin et al., PNAS USA 90:5873–5787 (1993). A particularly useful BLAST program is the WU-BLAST-2 program which was obtained from Altschul et al., Methods in Enzymology, 266: 460–480 (1996). WU-BLAST-2 uses several search parameters, most of which are set to the default values. The adjustable parameters are set with the following values: overlap span=1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al. Nucleic Acids Res. 25:3389–3402. Gapped BLAST uses BLOSUM-62 substitution scores; threshold T parameter set to 9; the two-hit method to trigger ungapped extensions; charges gap lengths of k a cost of 10+k; $X_u$ set to 16, and $X_g$ set to 40 for database search stage and to 67 for the output stage of the algorithms. Gapped alignments are triggered by a score corresponding to ~22 bits.

A percent amino acid sequence identity value is determined by the number of matching identical residues divided by the total number of residues of the "longer" sequence in the aligned region. The "longer" sequence is the one having the most actual residues in the aligned region (gaps introduced by WU-Blast-2 to maximize the alignment score are ignored).

In a similar manner, "percent (%) nucleic acid sequence identity" with respect to the coding sequence of the polypeptides identified herein is defined as the percentage of nucleotide residues in a candidate sequence that are identical with the nucleotide residues in the coding sequence of the Hck protein. A preferred method utilizes the BLASTN module of WU-BLAST-2 set to the default parameters, with overlap span and overlap fraction set to 1 and 0.125, respectively.

The alignment may include the introduction of gaps in the sequences to be aligned. In addition, for sequences which contain either more or fewer amino acids than the protein encoded by the sequences in the Figures, it is understood that in one embodiment, the percentage of sequence identity will be determined based on the number of identical amino acids in relation to the total number of amino acids. Thus, for example, sequence identity of sequences shorter than that shown in the Figure, as discussed below, will be determined using the number of amino acids in the shorter sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described below for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleosides, frameshifts, unknown nucleosides, or other types of sequencing errors in any of the sequences; however, the correct sequences will fall within the homology and stringency definitions herein.

In a preferred embodiment, an Hck protein provided herein has one or more of the following characteristics: ability to bind to Nef, WASP, WIP, gp130, CD44, CD4, IL-2R, Btk, Bcr-abl, Ras-GAP, hBRAG, Ig-α, Ig-β, or p120Cbl; similarity, homology or identity to the amino acid sequence set forth in SEQ ID NO:2; homology to src-like non-receptor tyrosine kinases; tyrosine kinase activity; the ability to modulate leukocyte and platelet activation; the ability to modulate antigen-receptor induced CD69 expression in lymphocytes; the ability to modulate CD23 induction by IL-4, CD40L, or IL-4 and CD40L in lymphocytes; the ability to modulate BCR-induced calcium flux in B-lymphocytes; the ability to modulate immunoglobulin heavy chain gene (IgH) promoter activity in B lymphocytes; the ability to modulate intracellular calcium in lymphocytes; and the ability to modulate NFAT activity in lymphocytes. Homology and identity to SEQ ID NO:2 and src-like non-receptor tyrosine kinases can be determined as described above. In one embodiment, homology and identity are determined by performing a Blastp search in Genbank's non-redundant protein database using default parameters. In another embodiment, homology and identity are determined using the following database and parameters: Database: Non-redundant GenBank CDS translations+PDB+SwissProt+Spupdate+PIR; Lambda of 0.316, K of 0.133 and H of 0; Gapped Lambda of 0.27, K of 0.047, and H of 4.94e-324; Matrix is BLOSUM62; Gap Penalties: Existence: 11, Extension: 1.

In a preferred embodiment, the Hck protein comprises the amino acid sequence set forth in SEQ ID NO:2. The characteristics described below also apply to other preferred Hck proteins provided herein.

In some preferred embodiments, the Hck protein binds to an Hck binding partner selected from the group consisting of Nef, WASP, WIP, gp130, CD44, CD4, IL-2R, Btk, Bcr-abl, Ras-GAP, hBRAG, Ig-α, Ig-β, and p120Cbl. In a preferred embodiment, the Hck protein binds to an Hck binding partner in T-cells. In another preferred embodiment, the Hck protein binds to an Hck binding partner in B-cells. In another preferred embodiment, the Hck protein binds to an Hck binding partner in mast cells. In another preferred embodiment, the Hck protein binds to an Hck binding partner in monocytes. In another preferred embodiment, the Hck protein binds to an Hck binding partner in macrophages. In another preferred embodiment, the Hck protein binds to an Hck binding partner in peripheral blood lymphocytes. In another preferred embodiment, the Hck protein binds to an Hck binding partner in granulocytes. In another preferred embodiment, the Hck protein binds to an Hck binding partner in platelets. In an especially preferred embodiment, the Hck protein binds to an Hck binding partner in vitro.

Hck proteins of the present invention may be shorter or longer than the amino acid sequence encoded by the nucleic acid sequence shown in SEQ ID NO:1. Thus, in a preferred embodiment, included within the definition of Hck proteins are portions or fragments of the amino acid sequences encoded by the nucleic acid sequences provided herein. In one embodiment herein, fragments of Hck proteins are considered Hck proteins if a) they share at least one antigenic epitope; b) have at least the indicated sequence identity; c) and preferably have Hck protein activity as further defined herein. In some cases, where the sequence is used diagnostically, that is, when the presence or absence of Hck nucleic acid is determined, only the indicated sequence identity is required. The nucleic acids of the present invention may also be shorter or longer than the sequences in SEQ ID NO:1.

In addition, as is more fully outlined below, Hck proteins can be made that are longer than those depicted in SEQ ID NO:2; for example, by the addition of epitope or purification tags, the addition of other fusion sequences, or the elucidation of additional coding and non-coding sequences. As described below, the fusion of an Hck peptide to a fluorescent protein, such as Blue Fluorescent Protein (BFP) or Green Fluorescent Protein (GFP), including those of Aquorea and Renilla species, is particularly preferred. In another preferred embodiment, the fluorescent protein is a GFP from Ptilosarcus. In another preferred embodiment, the fluorescent protein is a GFP homologue from Anthozoa species (Matz et al., Nat. Biotech., 17:969–973, 1999).

In a preferred embodiment, when an Hck protein is to be used to generate antibodies, an Hck protein must share at least one epitope or determinant with the full length protein. By "epitope" or "determinant" herein is meant a portion of a protein which will generate and/or bind an antibody. Thus, in most instances, antibodies made to a smaller Hck protein will be able to bind to the full length protein. In a preferred embodiment, the epitope is unique; that is, antibodies generated to a unique epitope show little or no cross-reactivity. The term "antibody" includes antibody fragments, as are known in the art, including Fab Fab$_2$, single chain antibodies (Fv for example), chimeric antibodies, etc., either produced by the modification of whole antibodies or those synthesized de novo using recombinant DNA technologies.

In a preferred embodiment, the antibodies to an Hck protein are capable of reducing or eliminating the biological function of the Hck proteins described herein, as is described below. That is, the addition of anti-Hck antibodies (either polyclonal or preferably monoclonal) to Hck proteins (or cells containing Hck proteins) may reduce or eliminate their ability to modulate leukocyte and platelet activation. Generally, at least a 25% decrease in activity is preferred, with at least about 50% being particularly preferred and about a 95–100% decrease being especially preferred.

The anti-Hck antibodies of the invention bind to Hck proteins. In a preferred embodiment, the antibodies specifically bind to Hck proteins. By "specifically bind" herein is meant that the antibodies bind to the protein with a binding constant in the range of at least $10^{-4}$–$10^{-6}$ $M^{-1}$, with a preferred range being $10^{-7}$–$10^{-9}$ $M^{-1}$. Antibodies are further described below.

The Hck proteins and Hck nucleic acids of the present invention are preferably recombinant. As used herein and further defined below, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

The nucleic acid may be double stranded, single stranded, or contain portions of both double stranded and single stranded sequence. As will be appreciated by those in the art, the depiction of a single strand ("Watson") also defines the sequence of the other strand ("Crick"); thus the sequence depicted in SEQ ID NO:1 also discloses the complement of the sequence.

By the term "recombinant nucleic acid" herein is meant nucleic acid, originally formed in vitro, in general, by the manipulation of nucleic acid by endonucleases, in a form not normally found in nature. Thus an isolated Hck nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e. using the in vivo cellular machinery of the host cell rather than in vitro manipulations; however, such nucleic acids, once produced recombinantly, although subsequently replicated non-recombinantly, are still considered recombinant for the purposes of the invention. This includes nucleic acids which are incorporated into the genome of a host cell.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated or purified away from some or all of the proteins and compounds with which it is normally associated in its wild type host, and thus may be substantially pure. For example, an isolated protein is unaccompanied by at least some of the material with which it is normally associated in its natural state, preferably constituting at least about 0.5%, more preferably at least about 5% by weight of the total protein in a given sample. A substantially pure protein comprises at least about 75% by weight of the total protein, with at least about 80% being preferred, and at least about 90% being particularly preferred. The definition includes the production of an Hck protein from one organism in a different organism or host cell. Alternatively, the protein may be made at a significantly higher concentration than is normally seen, through the use of a inducible promoter or high expression promoter, such that the protein is made at increased concentration levels. Alternatively, the protein may be in a form not normally found in nature, as in the addition of an epitope tag or amino acid substitutions, insertions and deletions, as discussed below.

In one embodiment, the present invention provides Hck protein variants. These variants fall into one or more of three classes: substitutional, insertional or deletional variants. These variants ordinarily are prepared by site specific mutagenesis of nucleotides in the DNA encoding an Hck protein, using cassette or PCR mutagenesis or other techniques well known in the art, to produce DNA encoding the variant, and thereafter expressing the DNA in recombinant cell culture as outlined above. However, variant Hck protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the Hck protein amino acid sequence. The variants typically exhibit the same qualitative biological activity as the naturally occurring analogue, although variants can also be selected which have modified characteristics as will be more fully outlined below.

While the site or region for introducing an amino acid sequence variation is predetermined, the mutation per se need not be predetermined. For example, in order to optimize the performance of a mutation at a given site, random mutagenesis may be conducted at the target codon or region and the expressed Hck protein variants screened for the optimal combination of desired activity. Techniques for making substitution mutations at predetermined sites in DNA having a known sequence are well known, for example, M13 primer mutagenesis and PCR mutagenesis. Screening of the mutants is done using assays of Hck protein activities.

Amino acid substitutions are typically of single residues; insertions usually will be on the order of from about 1 to 20 amino acids, although considerably larger insertions may be tolerated. Deletions range from about 1 to about 20 residues, although in some cases deletions may be much larger.

Substitutions, deletions, insertions or any combination thereof may be used to arrive at a final derivative. Generally these changes are done on a few amino acids to minimize the alteration of the molecule. However, larger changes may be tolerated in certain circumstances. When small alterations in the characteristics of the Hck protein are desired, substitutions are generally made in accordance with the following chart:

CHART I

| Original Residue | Exemplary Substitutions |
| --- | --- |
| Ala | Ser |
| Arg | Lys |
| Asn | Gln, His |
| Asp | Glu |
| Cys | Ser |
| Gln | Asn |
| Glu | Asp |
| Gly | Pro |
| His | Asn, Gln |

CHART I-continued

| Original Residue | Exemplary Substitutions |
| --- | --- |
| Ile | Leu, Val |
| Leu | Ile, Val |
| Lys | Arg, Gln, Glu |
| Met | Leu, Ile |
| Phe | Met, Leu, Tyr |
| Ser | Thr |
| Thr | Ser |
| Trp | Tyr |
| Tyr | Trp, Phe |
| Val | Ile, Leu |

Substantial changes in function or immunological identity are made by selecting substitutions that are less conservative than those shown in Chart I. For example, substitutions may be made which more significantly affect: the structure of the polypeptide backbone in the area of the alteration, for example the alpha-helical or beta-sheet structure; the charge or hydrophobicity of the molecule at the target site; or the bulk of the side chain. The substitutions which in general are expected to produce the greatest changes in the polypeptide's properties are those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g. lysyl, arginyl, or histidyl, is substituted for (or by) an electronegative residue, e.g. glutamyl or aspartyl; or (d) a residue having a bulky side chain, e.g. phenylalanine, is substituted for (or by) one not having a side chain, e.g. glycine.

The variants typically exhibit the same qualitative biological activity and will elicit the same immune response as the naturally-occurring analogue. However, variants may also be selected to modify the characteristics of the Hck proteins as needed. In addition, the variant may be designed such that the biological activity of the Hck protein is altered. For example, catalytic residues or targeting sequences may be altered.

In a preferred embodiment, Hck variant proteins are provided which lack at least one Hck protein activity. In a preferred embodiment, the Hck variant protein lacks tyrosine kinase activity. In another preferred embodiment, the Hck variant protein lacks the ability to bind to at least one Hck binding partner selected from the group consisting of WASP, WIP, Nef, gp130, CD44, CD4, IL-2R, Btk, Bcr-abl, Ras-GAP, hBRAG, Ig-α, Ig-β, and p120Cbl. In another preferred embodiment, the Hck variant protein lacks the ability to phosphorylate an Hck substrate, preferably selected from the group consisting of WASP, enolase, Ras-GAP, p120Cbl, and Bcr-abl.

Among the preferred Hck variant proteins are variants with a point mutation or deletion at the conserved lysine residue of the catalytic tyrosine kinase domain. Particularly preferred are mutants having mutations in residues corresponding to K269 in SEQ ID NO:2. Particularly preferred are mutants corresponding to K269E and K269M, as related to SEQ ID NO:2.

In a preferred embodiment, an Hck variant protein provided herein exhibits dominant negative activity, i.e., inhibits the activity of wildtype Hck protein. Such proteins are sometimes referred to herein as dominant negative Hck proteins. Especially preferred are variant proteins which are capable of inhibiting the ability of wildtype Hck to mediate lymphocyte activation. Most preferred are variant proteins capable of inhibiting BCR-induced immunoglobulin production.

In one embodiment, a dominant negative Hck protein provided herein inhibits activation of the NFAT gene promoter in lymphocytes.

In a preferred embodiment, the dominant negative Hck protein inhibits activation of the IgH promoter in lymphocytes.

Without being bound by theory, in one aspect the dominant negative Hck protein acts downstream of TCR, BCR, surface IgE, or other surface antigen receptors, or other catalytic receptors, which will activate leukocytes or platelets when engaged.

In a preferred embodiment, Hck variant proteins are provided which have constitutive tyrosine kinase activity, or increased specific activity as compared to wildtype Hck. Increased activity may be due to a higher level of catalytic efficiency, a higher affinity for substrate, a lower level of inhibition, or a combination thereof.

In a preferred embodiment, such Hck variants increase basal lymphocyte activity. In one aspect, such Hck variant proteins potentiate or increase lymphocyte activation, for example in response to stimuli including but not limited to BCR and TCR engagement. In one aspect, such Hck variant proteins increase mast cell activation, for example in response to stimulation including but not limited to binding of antigen to surface IgE. In another embodiment, such Hck variants increase platelet proliferation. Such Hck variants find use in the treatment of immune-compromised disease states, such as AIDS, and in the treatment of platelet proliferation disorders, such as Wiskott Aldrich syndrome.

Covalent modifications of Hck polypeptides are included within the scope of this invention. One type of covalent modification includes reacting targeted amino acid residues of an Hck polypeptide with an organic derivatizing agent that is capable of reacting with selected side chains or the N-or C-terminal residues of an Hck polypeptide. Derivatization with bifunctional agents is useful, for instance, for crosslinking Hck to a water-insoluble support matrix or surface for use in the method for purifying anti-Hck antibodies or screening assays, as is more fully described below. Commonly used crosslinking agents include, e.g., 1,1-bis (diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), bifunctional maleimides such as bis-N-maleimido-1,8-octane and agents such as methyl-3-[(p-azidophenyl)dithio]propioimidate.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the "-amino groups of lysine, arginine, and histidine side chains [T. E. Creighton, *Proteins: Structure and Molecular Properties*, W.H. Freeman & Co., San Francisco, pp. 79–86 (1983)], acetylation of the N-terminal amine, and amidation of any C-terminal carboxyl group.

Another type of covalent modification of the Hck polypeptide included within the scope of this invention comprises altering the native glycosylation pattern of the polypeptide. "Altering the native glycosylation pattern" is intended for purposes herein to mean deleting one or more carbohydrate moieties found in native sequence Hck polypeptide, and/or adding one or more glycosylation sites that are not present in the native sequence Hck polypeptide.

Addition of glycosylation sites to Hck polypeptides may be accomplished by altering the amino acid sequence thereof. The alteration may be made, for example, by the addition of, or substitution by, one or more serine or threonine residues to the native sequence Hck polypeptide (for O-linked glycosylation sites). The Hck amino acid sequence may optionally be altered through changes at the DNA level, particularly by mutating the DNA encoding the Hck polypeptide at preselected bases such that codons are generated that will translate into the desired amino acids.

Another means of increasing the number of carbohydrate moieties on the Hck polypeptide is by chemical or enzymatic coupling of glycosides to the polypeptide. Such methods are described in the art, e.g., in WO 87/05330 published Sep. 11, 1987, and in Aplin and Wriston, *CRC Crit. Rev. Biochem.*, pp. 259–306 (1981).

Removal of carbohydrate moieties present on the Hck polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., *Arch. Biochem. Biophys.*, 259:52 (1987) and by Edge et al., *Anal. Biochem.*, 118:131 (1981). Enzymatic cleavage of carbohydrate moieties on polypeptides can be achieved by the use of a variety of endo-and exo-glycosidases as described by Thotakura et al., *Meth. Enzymol.*, 138:350 (1987).

Another type of covalent modification of Hck comprises linking the Hck polypeptide to one of a variety of nonproteinaceous polymers, e.g., polyethylene glycol, polypropylene glycol, or polyoxyalkylenes, in the manner set forth in U.S. Pat. Nos. 4,640,835; 4,496,689; 4,301,144; 4,670,417; 4,791,192 or 4,179,337.

Hck polypeptides of the present invention may also be modified in a way to form chimeric molecules comprising an Hck polypeptide fused to another, heterologous polypeptide or amino acid sequence. In one embodiment, such a chimeric molecule comprises a fusion of an Hck polypeptide with a tag polypeptide which provides an epitope to which an anti-tag antibody can selectively bind. In a preferred embodiment, such a tag is the "flag tag" described below. The epitope tag is generally placed at the amino-or carboxyl-terminus of the Hck polypeptide. The presence of such epitope-tagged forms of an Hck polypeptide can be detected using an antibody against the tag polypeptide. Also, provision of the epitope tag enables the Hck polypeptide to be readily purified by affinity purification using an anti-tag antibody or another type of affinity matrix that binds to the epitope tag. In an alternative embodiment, the chimeric molecule may comprise a fusion of an Hck polypeptide with an immunoglobulin or a particular region of an immunoglobulin. For a bivalent form of the chimeric molecule, such a fusion could be to the Fc region of an IgG molecule as discussed further below.

Various tag polypeptides and their respective antibodies are well known in the art. Examples include poly-histidine (poly-his) or poly-histidine-glycine (poly-his-gly) tags; the flu HA tag polypeptide and its antibody 12CA5 [Field et al., *Mol. Cell. Biol.*, 8:2159–2165 (1988)]; the c-myc tag and the 8F9, 3C7, 6E10, G4, B7 and 9E10 antibodies thereto [Evan et al., *Molecular and Cellular Biology*, 5:3610–3616 (1985)]; and the Herpes Simplex virus glycoprotein D (gD) tag and its antibody [Paborsky et al., *Protein Engineering*. 3(6):547–553 (1990)]. Other tag polypeptides include the Flag-peptide [Hopp et al., *BioTechnology*, 6:1204–1210

(1988)]; the KT3 epitope peptide [Martin et al., *Science*, 255:192–194 (1992)]; tubulin epitope peptide [Skinner et al., *J. Biol. Chem.*, 266:15163–15166 (1991)]; and the T7 gene 10 protein peptide tag [Lutz-Freyermuth et al., *Proc. Natl. Acad. Sci. USA*, 87:6393–6397 (1990)].

In an embodiment herein, Hck protein family members and Hck proteins from other organisms are cloned and expressed as outlined below. Thus, probe or degenerate polymerase chain reaction (PCR) primer sequences may be used to find other related Hck proteins from humans or other organisms. As will be appreciated by those in the art, particularly useful probe and/or PCR primer sequences include the unique areas of the Hck nucleic acid sequence. As is generally known in the art, preferred PCR primers are from about 15 to about 35 nucleotides in length, with from about 20 to about 30 being preferred, and may contain inosine as needed. The conditions for the PCR reaction are well known in the art. It is therefore also understood that provided along with the sequences in the sequences listed herein are portions of those sequences, wherein unique portions of 15 nucleotides or more are particularly preferred. The skilled artisan can routinely synthesize or cut a nucleotide sequence to the desired length.

Once isolated from its natural source, e.g., contained within a plasmid or other vector or excised therefrom as a linear nucleic acid segment, the recombinant Hck nucleic acid can be further used as a probe to identify and isolate other Hck nucleic acids. It can also be used as a "precursor" nucleic acid to make modified or variant Hck nucleic acids and proteins.

Of course, as will be recognized by the artisan, PCR may also be used to obtain large quantities of a desired Hck nucleic acid from a source comprising such an Hck nucleic acid.

Using the nucleic acids of the present invention which encode an Hck protein, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the Hck protein. The term "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. As another example, operably linked refers to DNA sequences linked so as to be contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used to express the Hck protein; for example, transcriptional and translational regulatory nucleic acid sequences from *Bacillus* are preferably used to express the Hck protein in *Bacillus*. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are known in the art, and are useful in the present invention.

In addition, the expression vector may comprise additional elements. For example, the expression vector may have two replication systems, thus allowing it to be maintained in two organisms, for example in mammalian or insect cells for expression and in a prokaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

A preferred expression vector system is a retroviral vector system such as is generally described in PCT/US97/01019 and PCT/US97/01048, both of which are hereby expressly incorporated by reference.

Hck proteins of the present invention are produced by culturing a host cell transformed with an expression vector containing Hck nucleic acid encoding an Hck protein, under the appropriate conditions to induce or cause expression of the Hck protein. The conditions appropriate for Hck protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis,* SF9 cells, C129 cells, 293 cells, Neurospora, BHK, CHO, COS, and HeLa cells, fibroblasts, Schwanoma cell lines, immortalized mammalian myeloid and lymphoid cell lines.

In a preferred embodiment, the Hck proteins are expressed in mammalian cells. Mammalian expression systems are also known in the art, and include retroviral systems. A mammalian promoter is any DNA sequence capable of binding mammalian RNA polymerase and initiating the downstream (3') transcription of a coding sequence for Hck protein into mRNA. A promoter will have a transcription initiating region, which is usually placed proximal to the 5' end of the coding sequence, and usually a TATA box, typically located 25–30 base pairs upstream of the transcription initiation site. The TATA box is thought to direct RNA polymerase II to begin RNA synthesis at the correct site. However, TATA-free transcription initiation is also well known. A mammalian promoter will also contain an upstream promoter element (enhancer element), typically located within 100 to 200 base pairs upstream of the TATA box if present. An upstream promoter element determines the rate at which transcription is initiated and can act in either orientation. Of particular use as mammalian promoters are the promoters from mammalian viral genes, since the viral genes are often highly expressed and have a broad host range. Examples include the SV40 early promoter, mouse mammary tumor virus LTR promoter, adenovirus major late promoter, herpes simplex virus promoter, and the CMV promoter.

Typically, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation. Examples of transcription terminator and polyadenlytion signals include those derived form SV40.

The methods of introducing exogenous nucleic acid into mammalian hosts, as well as other hosts, are well known in the art, and will vary with the host cell used. Techniques include dextran-mediated transfection, calcium phosphate precipitation, polybrene mediated transfection, protoplast fusion, electroporation, viral infection, encapsulation of the polynucleotide(s) in liposomes, and direct microinjection of the DNA into nuclei.

In a preferred embodiment, Hck proteins are expressed in bacterial systems. Bacterial expression systems are well known in the art.

A suitable bacterial promoter is any nucleic acid sequence capable of binding bacterial RNA polymerase and initiating the downstream (3') transcription of the coding sequence of Hck protein into mRNA. A bacterial promoter has a transcription initiation region which is usually placed proximal to the 5' end of the coding sequence. This transcription initiation region typically includes an RNA polymerase binding site and a transcription initiation site. Sequences encoding metabolic pathway enzymes provide particularly useful promoter sequences. Examples include promoter sequences derived from sugar metabolizing enzymes, such as galactose, lactose and maltose, and sequences derived from biosynthetic enzymes such as tryptophan. Promoters from bacteriophage may also be used and are known in the art. In addition, synthetic promoters and hybrid promoters are also useful; for example, the tac promoter is a hybrid of the trp and lac promoter sequences. Furthermore, a bacterial promoter can include naturally occurring promoters of non-bacterial origin that have the ability to bind bacterial RNA polymerase and initiate transcription.

In addition to a functioning promoter sequence, an efficient ribosome binding site is desirable. In *E. coli,* the ribosome binding site is called the Shine-Delgarno (SD) sequence and includes an initiation codon and a sequence 3–9 nucleotides in length located 3–11 nucleotides upstream of the initiation codon.

The expression vector may also include a signal peptide sequence that provides for secretion of the Hck protein in bacteria. The signal sequence typically encodes a signal peptide comprised of hydrophobic amino acids which direct the secretion of the protein from the cell, as is well known in the art. The protein is either secreted into the growth media (gram-positive bacteria) or into the periplasmic space, located between the inner and outer membrane of the cell (gram-negative bacteria).

The bacterial expression vector may also include a selectable marker gene to allow for the selection of bacterial strains that have been transformed. Suitable selection genes include genes which render the bacteria resistant to drugs such as ampicillin, chloramphenicol, erythromycin, kanamycin, neomycin and tetracycline. Selectable markers also include biosynthetic genes, such as those in the histidine, tryptophan and leucine biosynthetic pathways.

These components are assembled into expression vectors. Expression vectors for bacteria are well known in the art, and include vectors for *Bacillus subtilis, E. coli, Streptococcus cremoris,* and *Streptococcus lividans,* among others.

The bacterial expression vectors are transformed into bacterial host cells using techniques well known in the art, such as calcium chloride treatment, electroporation, and others.

In one embodiment, Hck proteins are produced in insect cells. Expression vectors for the transformation of insect cells, and in particular, baculovirus-based expression vectors, are well known in the art.

In a preferred embodiment, Hck protein is produced in yeast cells. Yeast expression systems are well known in the art, and include expression vectors for *Saccharomyces cerevisiae, Candida albicans* and *C. maltosa, Hansenula polymorpha, Kluyveromyces fragilis* and *K. lactis, Pichia guillerimondii* and *P. pastoris, Schizosaccharomyces pombe,* and *Yarrowia lipolytica.* Preferred promoter sequences for expression in yeast include the inducible GAL1,10 promoter, the promoters from alcohol dehydrogenase, enolase, glucokinase, glucose-6-phosphate isomerase, glyceraldehyde-3-phosphate-dehydrogenase, hexokinase, phosphofructokinase, 3-phosphoglycerate mutase, pyruvate kinase, and the acid phosphatase gene. Yeast selectable markers include ADE2, HIS4, LEU2, TRP1, and ALG7, which confers resistance to tunicamycin; the neomycin phosphotransferase gene, which confers resistance to G418; and the CUP1 gene, which allows yeast to grow in the presence of copper ions.

The Hck protein may also be made as a fusion protein, using techniques well known in the art. Thus, for example, for the creation of monoclonal antibodies, if the desired epitope is small, the Hck protein may be fused to a carrier protein to form an immunogen. Alternatively, the Hck protein may be made as a fusion protein to increase expression, or for other reasons. For example, when the Hck protein is an Hck peptide, the nucleic acid encoding the peptide may be linked to other nucleic acid for expression purposes. Similarly, Hck proteins of the invention can be linked to protein labels, such as green fluorescent protein (GFP), red fluorescent protein (RFP), blue fluorescent protein (BFP), yellow fluorescent protein (YFP), etc.

In one embodiment, the Hck nucleic acids, proteins and antibodies of the invention are labeled. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

In a preferred embodiment, the Hck protein is purified or isolated after expression. Hck proteins may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the Hck protein may be purified using a standard anti-Hck antibody column. Ultrafiltration and diafiltration techniques, in conjunction with protein concentration, are also useful. For general guidance in suitable purification techniques, see Scopes, R., Protein Purification, Springer-Verlag, NY (1982). The degree of purification necessary will vary depending on the use of the Hck protein. In some instances no purification will be necessary.

Once expressed and purified if necessary, the Hck proteins and nucleic acids are useful in a number of applications.

The nucleotide sequences (or their complement) encoding Hck proteins have various applications in the art of molecular biology, including uses as hybridization probes, in chromosome and gene mapping and in the generation of antisense RNA and DNA. Hck protein nucleic acid will also be useful for the preparation of Hck proteins by the recombinant techniques described herein.

The full-length native sequence Hck protein gene, or portions thereof, may be used as hybridization probes for a cDNA library or genomic library to isolate other genes (for instance, those encoding naturally-occurring variants of Hck protein or Hck protein from other species) which have a desired sequence identity to the Hck protein coding sequence. Optionally, the length of the probes will be about 20 to about 50 bases. The hybridization probes may be derived from the nucleotide sequences herein or from genomic sequences including promoters, enhancer elements and introns of native sequences as provided herein. By way of example, a screening method will comprise isolating the coding region of the Hck protein gene using the known DNA sequence to synthesize a selected probe of about 40 bases. Hybridization probes may be labeled by a variety of labels, including radionucleotides such as $^{32}P$ or $^{35}S$, or enzymatic labels such as alkaline phosphatase coupled to the probe via avidin/biotin coupling systems. Labeled probes having a sequence complementary to that of the Hck protein gene of the present invention can be used to screen libraries of human cDNA, genomic DNA or mRNA to determine which members of such libraries the probe hybridizes.

Nucleotide sequences encoding an Hck protein can also be used to construct hybridization probes for mapping the gene which encodes that Hck protein and for the genetic analysis of individuals with genetic disorders. The nucleotide sequences provided herein may be mapped to a chromosome and specific regions of a chromosome using known techniques, such as in situ hybridization, linkage analysis against known chromosomal markers, and hybridization screening with libraries.

Nucleic acids which encode Hck protein or its modified forms can also be used to generate either transgenic animals or "knock out" animals which, in turn, are useful in the development and screening of therapeutically useful reagents. A transgenic animal (e.g., a mouse or rat) is an animal having cells that contain a transgene, which transgene was introduced into the animal or an ancestor of the animal at a prenatal, e.g., an embryonic stage. A transgene is a DNA which is integrated into the genome of a cell from which a transgenic animal develops. In one embodiment, cDNA encoding an Hck protein can be used to clone genomic DNA encoding an Hck protein in accordance with established techniques and the genomic sequences used to generate transgenic animals that contain cells which express the desired Hck DNA. In another embodiment, cDNA is used in the formation of a transgene. Methods for generating transgenic animals, particularly animals such as mice or rats, have become conventional in the art and are described, for example, in U.S. Pat. Nos. 4,736,866 and 4,870,009. Typically, particular cells would be targeted for the Hck protein transgene expression with tissue-specific enhancers. Transgenic animals that include a copy of a transgene encoding an Hck protein introduced into the germ line of the animal at an embryonic stage can be used to examine the effect of increased expression of the desired nucleic acid. Such animals can be used as tester animals for reagents thought to confer protection from, for example, pathological conditions associated with its overexpression. In accordance with this facet of the invention, an animal is treated with the reagent and a reduced incidence of the pathological condition, compared to untreated animals bearing the transgene, would indicate a potential therapeutic intervention for the pathological condition.

Alternatively, non-human homologues of the Hck protein can be used to construct an Hck protein "knock out" animal which has a defective or altered gene encoding an Hck protein as a result of homologous recombination between the endogenous gene encoding an Hck protein and altered genomic DNA encoding an Hck protein introduced into an embryonic cell of the animal. For example, cDNA encoding an Hck protein can be used to clone genomic DNA encoding an Hck protein in accordance with established techniques. A portion of the genomic DNA encoding an Hck protein can be deleted or replaced with another gene, such as a gene encoding a selectable marker which can be used to monitor integration. Typically, several kilobases of unaltered flanking DNA (both at the 5' and 3' ends) are included in the vector [see e.g., Thomas and Capecchi, Cell, 51:503 (1987) for a description of homologous recombination vectors]. The vector is introduced into an embryonic stem cell line (e.g., by electroporation) and cells in which the introduced DNA has homologously recombined with the endogenous DNA are selected [see e.g., Li et al., Cell 69:915 (1992)]. The selected cells are then injected into a blastocyst of an animal (e.g., a mouse or rat) to form aggregation chimeras [see e.g., Bradley, in *Teratocarcinomas and Embryonic Stem Cells: A Practical Approach,* E. J. Robertson, ed. (IRL, Oxford, 1987), pp. 113–152]. A chimeric embryo can then be implanted into a suitable pseudopregnant female foster animal and the embryo brought to term to create a "knock out" animal. Progeny harboring the homologously recombined DNA in their germ cells can be identified by standard techniques and used to breed animals in which all cells of the animal contain the homologously recombined DNA. Knockout animals can be characterized for instance, for their ability to defend against certain pathological conditions and for their development of pathological conditions due to absence of the Hck protein.

It is understood that the models described herein can be varied. For example, "knock-in" models can be formed, or the models can be cell-based rather than animal models.

Nucleic acid encoding the Hck polypeptides, antagonists or agonists may also be used in gene therapy. In gene therapy applications, genes are introduced into cells in order to achieve in vivo synthesis of a therapeutically effective genetic product, for example for replacement of a defective gene. "Gene therapy" includes both conventional gene therapy where a lasting effect is achieved by a single treatment, and the administration of gene therapeutic agents, which involves the one time or repeated administration of a therapeutically effective DNA or mRNA. Antisense RNAs and DNAs can be used as therapeutic agents for blocking the expression of certain genes in vivo. It has already been shown that short antisense oligonucleotides can be imported into cells where they act as inhibitors, despite their low intracellular concentrations caused by their restricted uptake by the cell membrane. (Zamecnik et al., *Proc. Natl. Acad. Sci. USA* 83, 4143–4146 [1986]). The oligonucleotides can be modified to enhance their uptake, e.g. by substituting their negatively charged phosphodiester groups by uncharged groups.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. The currently preferred in vivo gene transfer techniques include transfection with viral (typically retroviral) vectors and viral coat protein-liposome mediated transfection (Dzau et al., *Trends in Biotechnology* 11, 205–210 [1993]). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, proteins that target intracellular localization and enhance intracellular half-life. The technique of receptor-mediated endocytosis is described, for example, by Wu et al, *J. Biol. Chem.* 262, 4429–4432 (1987); and Wagner et al., *Proc. Natl. Acad. Sci. USA* 87 3410–3414 (1990). For review of gene marking and gene therapy protocols see Anderson et al., *Science* 256, 808–813 (1992).

In a preferred embodiment, the Hck proteins, nucleic acids, variants, modified proteins, cells and/or transgenics containing the said nucleic acids or proteins are used in screening assays. Identification of the Hck proteins provided herein permits the design of drug screening assays for compounds that bind Hck proteins, interfere with Hck protein binding, modulate Hck activity, modulate lymphocyte activation, and modulate platelet and lymphocyte proliferation.

The assays described herein preferably utilize the human Hck protein, although other mammalian proteins may also be used, including rodents (mice, rats, hamsters, guinea pigs, etc.), farm animals (cows, sheep, pigs, horses, etc.) and primates. These latter embodiments may be preferred in the development of animal models of human disease. In some embodiments, as outlined herein, truncated Hck proteins may be used.

In a preferred embodiment, the methods comprise combining an Hck protein and a candidate bioactive agent, and determining the binding of the candidate agent to the Hck protein. In other embodiments, further discussed below, binding interference or bioactivity is determined.

The term "candidate bioactive agent" or "exogeneous compound" as used herein describes any molecule, e.g., protein, small organic molecule, carbohydrates (including polysaccharides), polynucleotide, lipids, etc. Generally a plurality of assay mixtures are run in parallel with different agent concentrations to obtain a differential response to the various concentrations. Typically, one of these concentrations serves as a negative control, i.e., at zero concentration or below the level of detection. In addition, positive controls, i.e. the use of agents known to bind Hck protein, may be used.

Candidate agents encompass numerous chemical classes, though typically they are organic molecules, preferably small organic compounds having a molecular weight of more than 100 and less than about 2,500 daltons, more preferably between 100 and 2000, more preferably between about 100 and about 1250, more preferably between about 100 and about 1000, more preferably between about 100 and about 750, more preferably between about 200 and about 500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Particularly preferred are peptides.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In a preferred embodiment, a library of different candidate bioactive agents are used. Preferably, the library should provide a sufficiently structurally diverse population of randomized agents to effect a probabilistically sufficient range of diversity to allow binding to a particular target. Accordingly, an interaction library should be large enough so that at least one of its members will have a structure that gives it affinity for the target. Although it is difficult to gauge the required absolute size of an interaction library, nature provides a hint with the immune response: a diversity of $10^7$–$10^8$ different antibodies provides at least one combination with sufficient affinity to interact with most potential antigens faced by an organism. Published in vitro selection techniques have also shown that a library size of $10^7$ to $10^8$ is sufficient to find structures with affinity for the target. A library of all combinations of a peptide 7 to 20 amino acids in length, such as generally proposed herein, has the potential to code for $20^7$ ($10^9$) to $20^{20}$. Thus, with libraries of $10^7$ to $10^8$ different molecules the present methods allow a "working" subset of a theoretically complete interaction library for 7 amino acids, and a subset of shapes for the $20^{20}$ library. Thus, in a preferred embodiment, at least $10^6$, preferably at least $10^7$, more preferably at least $10^8$ and most preferably at least $10^9$ different sequences are simultaneously analyzed in the subject methods. Preferred methods maximize library size and diversity.

In a preferred embodiment, the candidate bioactive agents are proteins. By "protein" herein is meant at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids. For example, homo-phenylalanine, citrulline and noreleucine are considered amino acids for the purposes of the invention. "Amino acid" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations. Chemical blocking groups or other chemical substituents may also be added.

In a preferred embodiment, the candidate bioactive agents are naturally occurring proteins or fragments of naturally occurring proteins. Thus, for example, cellular extracts containing proteins, or random or directed digests of proteinaceous cellular extracts, may be used. In this way libraries of procaryotic and eukaryotic proteins may be made for screening in the systems described herein. Particularly preferred in this embodiment are libraries of bacterial, fungal, viral, and mammalian proteins, with the latter being preferred, and human proteins being especially preferred.

In a preferred embodiment, the candidate bioactive agents are peptides of from about 5 to about 30 amino acids, with from about 5 to about 20 amino acids being preferred, and from about 7 to about 15 being particularly preferred, and 12 and 18 amino acids being most preferred. The peptides may be digests of naturally occurring proteins as is outlined above, random peptides, or "biased" random peptides. By "randomized" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized candidate bioactive proteinaceous agents.

In one embodiment, the library is fully randomized, with no sequence preferences or constants at any position. In a preferred embodiment, the library is biased. That is, some positions within the sequence are either held constant, or are selected from a limited number of possibilities. For example, in a preferred embodiment, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, etc., or to purines, etc.

In a preferred embodiment, the candidate bioactive agents are nucleic acids. By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage, et al., Tetrahedron, 49(10):1925 (1993) and references therein; Letsinger, *J. Org. Chem.*, 35:3800 (1970); Sprinzl, et al, *Eur. J. Biochem.*, 81:579 (1977); Letsinger, et al., *Nucl. Acids Res.*, 14:3487 (1986); Sawai, et al., *Chem. Lett.*, 805 (1984), Letsinger, et al., *J. Am. Chem. Soc.*, 110:4470 (1988); and Pauwels, et al., *Chemica Scripta*, 26:141 (1986)), phosphorothioate (Mag, et al., *Nucleic Acids Res.*, 19:1437 (1991); and U.S. Pat. No. 5,644,048), phosphorodithioate (Briu, et al., *J. Am. Chem. Soc.*, 111:2321 (1989)), O-methylphophoroamidite linkages (see Eckstein, Oligonucleotides and Analogues: A Practical Approach, Oxford University Press), and peptide nucleic acid backbones and linkages (see Egholm, *J. Am. Chem. Soc.*, 114:1895 (1992); Meier, et al., *Chem. Int. Ed. Engl.*, 31:1008 (1992); Nielsen, *Nature*, 365:566 (1993); Carlsson, et al., *Nature*, 380:207 (1996), all of which are incorporated by reference)). Other analog nucleic acids include those with positive backbones (Denpcy, et al., *Proc. Natl. Acad. Sci. USA*, 92:6097 (1995)); non-ionic backbones (U.S. Pat. Nos. 5,386,023; 5,637,684; 5,602,240; 5,216,141; and 4,469,863; Kiedrowski, et al., *Angew. Chem. Intl. Ed. English*, 30:423 (1991); Letsinger, et al., *J. Am. Chem. Soc.*, 110:4470 (1988); Letsinger, et al., Nucleoside & Nucleotide, 13:1597 (1994); Chapters 2 and 3, ASC Symposium Series 580, "Carbohydrate Modifications in Antisense Research", Ed. Y. S. Sanghui and P. Dan Cook; Mesmaeker, et al., *Bioorganic & Medicinal Chem. Lett.* 4:395 (1994); Jeffs, et al., *J. Biomolecular NMR*, 34:17 (1994); Tetrahedron Lett., 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars, as well as "locked nucleic acids", are also included within the definition of nucleic acids (see Jenkins, et al., *Chem. Soc. Rev., (*1995) pp. 169–176). Several nucleic acid analogs are described in Rawls, C & E News, Jun. 2, 1997, page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

For an example of how nucleic acids may be used as candidate agents to screen for a change in phenotype, see Holland et al., J. Exp. Med., 194:1263–1276, 2001. See also Hitoshi et al., Immunity, 8:461–471, 1998. Both of which are expressly incorporated herein by reference.

As described above generally for proteins, nucleic acid candidate bioactive agents may be naturally occurring nucleic acids, random nucleic acids, or "biased" random nucleic acids. For example, digests of procaryotic or eukaryotic genomes may be used as is outlined above for proteins.

In a preferred embodiment, the candidate bioactive agents are organic chemical moieties or small molecule chemical compositions, a wide variety of which are available in the literature. Preferred small molecule chemical compounds are from about 100 to about 1000 daltons, more preferably from about 100 to about 500 daltons.

In a preferred embodiment, the candidate bioactive agents are linked to a fusion partner. By "fusion partner" or "functional group" herein is meant a sequence that is associated with the candidate bioactive agent, that confers upon all members of the library in that class a common function or ability. Fusion partners can be heterologous (i.e. not native to the host cell), or synthetic (not native to any cell). Suitable fusion partners include, but are not limited to: a) presentation structures, which provide the candidate bioactive agents in a conformationally restricted or stable form; b) targeting sequences, which allow the localization of the candidate bioactive agent into a subcellular or extracellular compartment; c) rescue sequences which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; or f) any combination of a), b), c), d), and e), as well as linker sequences as needed.

Generally, in a preferred embodiment of the methods herein, for example for binding assays, the Hck protein or the candidate agent is non-diffusibly bound to an insoluble support having isolated sample receiving areas (e.g. a microtiter plate, an array, etc.). The insoluble supports may be made of any composition to which the compositions can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, teflon™, etc. Microtiter plates and arrays are especially convenient because a large number of assays can be carried out simultaneously, using small amounts of reagents and samples. In some cases magnetic beads and the like are included. The particular manner of binding of the composition is not crucial so long as it is compatible with the reagents and overall methods of the invention, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety. Also included in this invention are screening assays wherein solid supports are not used; examples of such are described below.

In a preferred embodiment, the Hck protein is bound to the support, and a candidate bioactive agent is added to the assay. Alternatively, the candidate agent is bound to the support and the Hck protein is added. Novel binding agents include specific antibodies, non-natural binding agents identified in screens of chemical libraries, peptide analogs, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the Hck protein may be done in a number of ways. In a preferred embodiment, the candidate bioactive agent is labeled, and binding determined directly. For example, this may be done by attaching all or a portion of the Hck protein to a solid support, adding a labelled candidate agent (for example a fluorescently labeled agent), washing off excess reagent, and determining whether the label is present on the solid support. Various blocking and washing steps may be utilized as is known in the art.

By "labeled" herein is meant that the compound is either directly or indirectly labeled with a label which provides a detectable signal, e.g. radioisotope, fluorescers, enzyme, antibodies, particles such as magnetic particles, chemiluminescers, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the proteins (or proteinaceous candidate agents) may be labeled at tyrosine positions using $^{125}I$, or with fluorophores. Alternatively, more than one component may be labeled with different labels; using $^{125}I$ for the proteins, for example, and a fluorophor for the candidate agents.

In a preferred embodiment, the binding of the candidate bioactive agent is determined through the use of competitive binding assays. In this embodiment, the competitor is a binding moiety known to bind to the target molecule (i.e. Hck protein), such as an antibody, peptide, binding partner, ligand, etc. In a preferred embodiment, the competitor is selected from the group consisting of Nef, WASP, WIP, gp130, CD44, CD4, IL-2R, Btk, Bcr-abl, Ras-GAP, hBRAG, Ig-α, Ig-β, and p120Cbl. Under certain circumstances, there may be competitive binding as between the bioactive agent and the binding moiety, with the binding moiety displacing the bioactive agent. This assay can be used to determine candidate agents which interfere with binding of Hck to its binding partner. "Binding interference", or grammatical equivalents, as used herein means that native binding of the Hck protein differs in the presence of the candidate agent. The binding can be eliminated or can be with a reduced affinity. In one embodiment, interference is caused by, for example, a conformational change, rather than direct competition for the native binding site.

In one embodiment, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4° C. and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In a preferred embodiment, the competitor is added first, followed by the candidate bioactive agent. Displacement of the competitor is an indication that the candidate bioactive agent is binding to the Hck protein and thus is capable of binding to, and potentially modulating, the activity of the Hck protein. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In an alternative embodiment, the candidate bioactive agent is added first, with incubation and washing, followed by the competitor. The absence of binding by the competitor may indicate that the bioactive agent is bound to the Hck protein with a higher affinity. Thus, if the candidate bioactive agent is labeled, the presence of the label on the support, coupled with a lack of competitor binding, may indicate that the candidate agent is capable of binding to the Hck protein.

In a preferred embodiment, the methods comprise differential screening to identity bioactive agents that are capable of modulating the activity of the Hck proteins. Such assays can be done with the Hck protein or cells comprising Hck protein. Hck protein may be recombinant Hck protein produced and collected as described herein, or may be a cell lysate from a cell comprising an Hck protein or a recombinant Hck protein. In one embodiment, the methods comprise combining an Hck protein and a competitor in a first sample. A second sample comprises a candidate bioactive agent, an Hck protein and a competitor. The binding of the competitor is determined for both samples, and a change, or difference in binding between the two samples indicates the presence of an agent capable of binding to the Hck protein and modulating its activity. That is, if the binding of the competitor is different in the second sample relative to the first sample, the agent is capable of binding to the Hck protein and modulating its activity.

Alternatively, a preferred embodiment utilizes differential screening to identify drug candidates that bind to the native Hck protein, but cannot bind to modified Hck proteins. The structure of the Hck protein may be modeled, and used in rational drug design to synthesize agents that interact with a catalytic, binding, or regulatory domain.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Screening for agents that modulate the activity of an Hck protein may also be done. In a preferred embodiment, methods for screening for a bioactive agent capable of modulating the activity of an Hck protein comprise the steps of adding a candidate bioactive agent to a sample of an Hck protein (or a cell comprising an Hck protein) and determining an alteration in the biological activity of the Hck protein. A sample of an Hck protein may be obtained by recombinantly producing and collecting Hck protein, as described herein, or by obtaining a cell lysate from a cell comprising an Hck protein or a recombinant Hck protein by means known in the art. "Modulating the activity of an Hck protein" includes an increase in activity, a decrease in activity, or a change in the type or kind of activity present. Thus, in this embodiment, the candidate agent may bind to an Hck protein (although this may not be necessary), and should alter its biological or biochemical activity as defined herein. The methods include both in vitro screening methods, as are generally outlined above, and in vivo screening of cells for alterations in the presence, cellular distribution, subcellular distribution, activity or amount of Hck protein. In vitro assays may be performed using cell lysates following in vivo manipulations involved in screens.

By "Hck protein activity" or grammatical equivalents herein is meant at least one of the Hck protein's biological activities, including, but not limited to, modulation of leukocyte activation; modulation of platelet activation; modulation of lymphocyte proliferation; modulation of platelet proliferation; modulation of lymphocyte activation; modulation of B-lymphocyte activation; modulation of B-lymphocyte activation by BCR stimulation; modulation of T-lymphocyte activation; modulation of T-lymphocyte activation by TCR stimulation; modulation of mast cell activation by stimulation of surface IgE; modulation of B-lymphocyte differentiation; modulation of IgM, IgG induction in B-lymphocytes; modulation of immunoglobulin heavy chain gene promoter activity in lymphocytes; modulation of NFAT activity in lymphocytes; modulation of immunoglobulin secretion by B-lymphocytes; modulation of cytokine production in leukocytes; modulation of surface protein expression including CD23, CD69, CD80 and CD86 in lymphocytes; the ability to modulate CD23 induction by IL-4, CD40L, or IL-4 and CD40L in lymphocytes; modulation of intracellular calcium concentration; modulation of release of calcium from intracellular stores; modulation of intracellular calcium concentration change in response to BCR stimulation; binding to Nef, WASP, WIP, gp130, CD44, CD4, IL-2R, Btk, Bcr-abl, Ras-GAP, hBRAG, Ig-$\alpha$, Ig-$\beta$, and p120Cbl; kinase activity; tyrosine kinase activity; kinase activity directed at WASP; and tyrosine kinase activity directed at WASP.

In a preferred embodiment, the activity of the Hck protein is decreased; in another preferred embodiment, the activity of the Hck protein is increased. Thus, bioactive agents that are antagonists are preferred in some embodiments, and bioactive agents that are agonists are preferred in other embodiments.

In an especially preferred embodiment, methods of screening for candidate bioactive agents capable of modulating the kinase activity, preferably the tyrosine kinase activity, of an Hck protein are provided. In vitro kinase assays for measuring Hck kinase activity are known, for example see reviews of Reth, Ann. Rev. Immunol., 10:97–131, 1992; Kim et al., Immunol. Rev. 132:126–145, 1993; Schlessinger, Cell, 103:211–225, 2000, and references therein. Substrates for use in kinase assays include, but are not limited to, enloase, p120Cbl, Bcr-abl, WASP, and RAS-GTPase-activating protein. WASP is especially preferred. Candidate agents may be added to cells comprising Hck protein, or nucleic acid encoding Hck protein, and Hck kinase assays may be performed using cell lysates, or Hck protein recovered from such cells. Alternatively, Hck phosphorylation substrate may be added to cells, and its phosphorylation measured within cells or in cell lysates. In a preferred embodiment, in vitro kinase assays are done, using isolated or in vitro translated Hck protein.

In a preferred embodiment, the Hck protein used (or encoded) for kinase assays comprises a tyrosine kinase domain and lacks SH2 and SH3 domains. In a preferred embodiment, such an Hck protein comprises an amino acid sequence having at least about 85%, more preferably at least about 90%, more preferably at least about 95%, more preferably at least about 98% identity to the amino acid sequence set forth by residues 241–490, 241–505, or 230–505 in SEQ ID NO:2. In an especially preferred embodiment, the Hck protein comprises the amino acid sequence set forth by residues 241–490, 241–505, or 230–505 in SEQ ID NO:2.

In another preferred embodiment, the Hck protein used (or encoded) for kinase assays consists essentially of a tyrosine kinase domain. In a preferred embodiment, such an Hck protein consists essentially of an amino acid sequence having at least about 85%, more preferably at least about 90%, more preferably at least about 95%, more preferably at least about 98% identity to the amino acid sequence set forth by residues 241–490, 241–505, or 230–505 in SEQ ID NO:2. In an especially preferred embodiment, the Hck protein consists essentially of the amino acid sequence set forth by residues 241–490, 241–505, or 230–505 in SEQ ID NO:2.

In another preferred embodiment, an Hck protein (or nucleic acid encoding the same) comprising an SH2 domain, an SH3 domain, and a tyrosine kinase domain is used in kinase assays. In a preferred embodiment, such an Hck protein comprises an amino acid sequence having at least about 85%, more preferably at least about 90%, more preferably at least about 95%, more preferably at least about 98% identity to the amino acid sequence set forth by SEQ ID NO:2. In an especially preferred embodiment, the Hck protein comprises SEQ ID NO:2.

Screening for agents that modulate B-cell activation and T-cell activation may also be done.

In a preferred embodiment, the methods comprise determining the ability of a candidate agent to bind to Hck.

In a preferred embodiment, the methods comprise detecting binding of candidate agent to Hck protein, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

It will be understood that while agents that normally induce lymphocyte activation (i.e., activation agents) are used, the screening method is designed to identify agents that are capable of inhibiting lymphocyte activation. Accordingly, the presence of a bioactive agent that is capable of inhibiting lymphocyte activation may preclude activation of the lymphocyte by the activation agent. Such agents are nevertheless referred to herein as activation agents, and the step of contacting the cells with such an activation agent is frequently referred to herein as "inducing lymphocyte activation", even though a candidate bioactive agent may inhibit such activation by the agent. This nomenclature applies to the methods that follow as well.

By immunosuppressant is meant an agent that suppresses the body's ability to react to an antigen.

Preferred Hck proteins for use in these methods comprise an SH2 and an SH3 domain but lack a tyrosine kinase domain. In an especially preferred embodiment, Hck proteins used consist essentially of the amino acid sequence set forth by residues 1–211, 1–230, or 61–211 in SEQ ID NO:2.

In another preferred embodiment, a full length Hck protein comprising SH2, SH3, and tyrosine kinase domains, and preferably comprising the amino acid sequence set forth in SEQ ID NO:2, is used.

Bioactive agents that inhibit lymphocyte activation in these assays are useful as immunosuppressants.

In another preferred embodiment, the methods comprise determining the ability of a candidate agent to modulate the binding of Hck to an Hck binding partner.

In a preferred embodiment, the methods comprise detecting decreased binding of Hck protein to an Hck binding partner in the presence of candidate agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Preferred Hck proteins for use in these methods comprise an SH2 domain and an SH3 domain but lack a tyrosine kinase domain. In an especially preferred embodiment, Hck proteins used consist essentially of the amino acid sequence set forth by residues 1–211, 1–230, or 61–211 in SEQ ID NO:2.

In another preferred embodiment, a full length Hck protein comprising SH2, SH3 and tyrosine kinase domains, and preferably comprising the amino acid sequence set forth in SEQ ID NO:2, is used.

In a preferred embodiment, the Hck binding partner is selected from the group consisting of Nef, gp130, WASP, WIP, CD44, CD4, IL-2R, Btk, Bcr-abl, Ras-GAP, hBRAG, Ig-α, Ig-β, and p120Cbl.

By decreased binding of Hck protein to Hck binding partner is meant a detectable decrease in binding as compared to binding in the absence of agent, or absence of binding.

Bioactive agents that inhibit lymphocyte activation in these assays are useful as immunosuppressants.

In another preferred embodiment, the methods comprise determining the ability of a candidate bioactive agent to modulate the activity of an Hck protein.

In a preferred embodiment, the methods comprise detecting a decrease in the kinase activity of Hck in the presence of candidate bioactive agent, contacting the candidate bioactive agent to a lymphocyte, and determining lymphocyte activation in the presence of said candidate agent. In a preferred embodiment, lymphocyte activation in the presence and absence of candidate agent is determined. In a preferred embodiment, an agent that normally induces lymphocyte activation is used. Lymphocyte activation is measured in the presence, and optionally, the absence of candidate agent following contact with the agent that normally induces lymphocyte activation. A preferred activation agent for use with B lymphocytes is anti-IgM antibody. A preferred activation agent for use with T lymphocytes is C305, i.e. anti-TCR antibody. In another embodiment, lymphocyte activation is induced using a phorbol ester, such as PMA, in combination with a calcium ionophore, such as ionomycin. In another embodiment, costimulation of CD3/CD28 in primary T-cells is done.

Preferred Hck proteins for use in these methods consist essentially of a kinase domain. In an especially preferred embodiment, Hck proteins used consist essentially of the amino acid sequence set forth by residues 241–490, 241–505, or 230–505 in SEQ ID NO:2.

In another preferred embodiment, full length Hck proteins comprising an SH2 domain, an SH3 domain, a tyrosine kinase domain, and preferably comprising the amino acid sequence set forth in SEQ ID NO:2, are used.

In a preferred embodiment, Hck protein is combined with Hck substrate protein and the phosphorylation of substrate protein is determined. By substrate protein is meant any protein capable of being phosphorylated by Hck. Especially preferred substrate proteins are WASP, p120Cbl, Ras-GAP, enolase and Ccr-abl.

By decrease in kinase activity is meant a detectable decrease in the ability of Hck to phosphorylate substrate as compared to its ability to phosphorylate substrate in the absence of agent, or loss of the ability to phosphorylate substrate.

Bioactive agents that inhibit lymphocyte activation in these assays are useful as immunosuppressants.

In a preferred embodiment, the methods comprise contacting a bioactive agent, which agent is determined to bind Hck, interfere with Hck binding, or modulate the activity of Hck, to a lymphocyte, stimulating the lymphocyte with either IL-4, CD40L, or CD40L and IL-4 in combination, and detecting an inhibition of the induction of CD23 expression. Preferred cells for use in these assays are Ramos cells.

Bioactive agents that inhibit lymphocyte activation in these assays are useful as immunosuppressants.

In a preferred embodiment, candidate bioactive agents used in these assays are small molecule chemical compounds, from about 100 to about 1500, more preferably about 100 to about 1200, more preferably about 100 to about 1000 more preferably about 200 to about 500 daltons.

In a preferred embodiment, a library of candidate bioactive agents is contacted to isolated or cell-free Hck protein.

In another preferred embodiment, a library of candidate bioactive agents is contacted to a population of cells comprising Hck.

In a preferred embodiment, determining lymphocyte activation in the methods herein comprises determining the level of expression of a surface marker which is associated with activation of the lymphocyte, in the presence of candidate agent. In a preferred embodiment, the level of surface marker expression is determined in the presence and absence of candidate agent. In a preferred embodiment, the surface marker is selected from the group consisting of CD40L, CD23, CD69, CD80 and CD86. In an especially preferred embodiment, the surface marker used is CD69 or CD23.

In another preferred embodiment, determining lymphocyte activation in the methods herein comprises determining the level of activity of a promoter in the presence of candidate agent, which activity correlates with lymphocyte activation in the absence of candidate agent. In a preferred embodiment, the level of promoter activity is determined in the presence and absence of candidate agent. In a preferred embodiment the promoter is an NFAT-responsive promoter, such as the IL-2 promoter. In an especially preferred embodiment, the promoter is the IgH promoter, further described below.

In a preferred embodiment, determining lymphocyte activation involves sorting lymphocytes by FACS.

In some embodiments, the methods involve determining lymphocyte activation by other means, which may also include the use of FACS. As will be appreciated, lymphocyte activation as well as non-lymphocyte leukocyte activation and platelet activation can be determined in a number of ways. It will be appreciated that mechanisms of leukocyte and platelet activation and methods for determining activation are known (see for example Kay, Immunol. Invest. 17:679–705, 1988; Lukacs et. al., Chem. Immunol. 72:102–120, 1999; Stankunas et al., Cold Spring Harbor Symposia on Quant. Biol., 64: 505–516, 1999; Metcalf et. al., Physiol. Rev. 77:1033–1079, 1997; Hematol. Oncol. Clin. North Am., 4:1–26, 1990; Brass et. al., Adv. Exp. Med. Biol., 344:17–36, 1993; Brass et. al., Thromb. Haemost., 70:217–223, 1993; *Cellular and Molecular Immunology* Abbas et. al., W. B. Saunders, ISBN 0-7216-3032-4, Chapters 7, 9, 12, and 14). Particularly relevant are the methods disclosed by Holland et al., J. Exp. Med., 194:1263–1276, 2001, expressly incorporated herein by reference.

In some embodiments, indicators of lymphocyte activation are used. There are a number of parameters that may be evaluated or assayed to determine lymphocyte activation, including, but not limited to, IgH promoter activity, NFAT activity, Ig secretion, IgG and IgM production, lymphocyte proliferation, expression cell surface markers correlated with lymphocyte activation, cytokine production, release of calcium from intracellular stores, amount of SYK protein, level of SYK protein ubiquitination, SYK protein tyrosine kinase activity, and IL-2 expression. These parameters may be assayed and used as indicators to evaluate the effect of candidate drug agents on lymphocyte activation. In this manner, rapid, accurate screening of candidate agents may be performed to identify agents that modulate lymphocyte activation.

By a "population of cells" or "library of cells" herein is meant at least two cells, with at least about $10^3$ being preferred, at least about $10^6$ being particularly preferred, and at least about $10^8$ to $10^9$ being especially preferred. The population or sample can contain a mixture of different cell types from either primary or secondary cultures although samples containing only a single cell type are preferred, for example, the sample can be from a cell line, particularly tumor cell lines, as outlined below. In a preferred embodiment, cells that are replicating or proliferating are used; this may allow the use of retroviral vectors for the introduction of candidate bioactive agents. Alternatively, non-replicating cells may be used, and other vectors (such as adenovirus and lentivirus vectors) can be used. In addition, although not required, the cells are compatible with dyes and antibodies.

Preferred cell types for use in the invention include, but are not limited to, mammalian cells, including animal (rodents, including mice, rats, hamsters and gerbils), primates, and human cells, particularly including tumor cells of all types, including breast, skin, lung, cervix, colorectal, leukemia, brain, etc. More preferable cell types include Jurkat cells and the Ig(+) and IgM secreting B-cell lines CL-01, LA350, BJAB, and CA46. Primary cells are also preferred, including peripheral blood mononuclear cells (PBMCs) and peripheral blood lymphocytes (PBLs). The lymphocytic Ramos cell line is also preferred.

Preferred cell surface markers useful as indicators of lymphocyte activation in the methods herein exhibit low background expression in the absence of lymphocyte activation. Especially preferred cell surface markers include CD40L, CD23, CD69, CD80, CD86. CD69 and CD23 are especially preferred.

Agents that recognize such surface molecules (e.g. antibodies) can be used as an affinity ligand, and attached to a solid support such as a bead, a surface,etc., and used to pull out cells that are undergoing T-cell and B-cell activation. Similarly, these agents can be coupled to a fluorescent dye such as PerCP, and then used as the basis of a fluorescence-activated cell sorting (FACS) separation.

FACS analysis can be used in conjunction with antibodies recognizing lymphocyte surface markers that are correlated with lymphocyte activation. FACS analysis is used to sort cells based on the expression of these markers to detect unstimulated and stimulated lymphocytes. In a preferred embodiment, sorted lymphocytes are used to retrieve candidate bioactive agents introduced thereto.

In a preferred embodiment, IgH promoter activity and NFAT activity are measured using lymphocyte clones comprising an IgH promoter or an NFAT-responsive promoter (such as IL-2 promoter) operably linked to a reporter gene. For example, a surface Ig(+), IgM secreting B-cell line such as the BJAB, CL-01, CA46, or LA350 cell line is transfected with a construct comprising GFP/2a/TK fusion under the control of an IgH promoter, Eµ and 3'α enhancer elements (for example, see Lieberson et al. EMBO J., 14:6229–6238, 1995). Stable transfectants (referred to herein as immunoglobulin heavy chain reporter cell lines) are selected and maintained in gancyclovir. Preferred immunoglobulin heavy chain reporter cell lines for use in the present invention exhibit low background GFP expression and strong basal activity and/or inducible activity in the presence of positive control. Such cell lines can be generated with the use of retroviral constructs.

Release of calcium from intracellular calcium stores may be assayed using membrane permeant vital calcium sensing fluorescent dyes, as are well known in the art. For example, see Calcium Green™, Calcium Orange™, from Molecular Probes, Eugene, Oreg., catalog numbers C-3010, C-3013, for example.

A preferred embodiment utilizes a cell proliferation assay. For example, B-cells proliferate when activated. By "proliferation assay" herein is meant an assay that allows the determination that a cell population is either proliferating, i.e. replicating, or not proliferating.

In a preferred embodiment, the proliferation assay is a dye inclusion assay. A dye inclusion assay relies on dilution effects to distinguish between proliferating and non-proliferating cells. Briefly, a dye (generally a fluorescent dye as outlined below) is introduced to cells and taken up by the cells. Once taken up, the dye is trapped in the cell, and does not diffuse out. As the cell population divides, the dye is proportionally diluted. That is, after the introduction of the inclusion dye, the cells are allowed to incubate for some period of time; cells that lose fluorescence over time are dividing, and the cells that remain fluorescent are arrested in a non-growth phase.

The rate of loss of fluorescence is indicative of the rate of proliferation. An increase in proliferation rate above that of unstimulated cells is indicative of B-cell activation.

These methods may also be applied to platelets.

Generally, the introduction of the inclusion dye may be done in one of two ways. Either the dye cannot passively enter the cells (e.g. it is charged), and the cells must be treated to take up the dye; for example through the use of an electric pulse. Alternatively, the dye can passively enter the cells, but once taken up, it is modified such that it cannot diffuse out of the cells. For example, enzymatic modification of the inclusion dye may render it charged, and thus unable to diffuse out of the cells. For example, the Molecular Probes CellTracker™ dyes are fluorescent chloromethyl derivatives that freely diffuse into cells, and then glutathione S-transferase-mediated reaction produces membrane impermeant dyes.

Suitable inclusion dyes include, but are not limited to, the Molecular Probes line of CellTracker™ dyes, including, but not limited to CellTracker™ Blue, CellTracker™ Yellow-Green, CellTracker™ Green, CellTracker™ Orange, PKH26 (Sigma), and others known in the art; see the Molecular Probes Handbook; chapter 15 in particular.

In general, inclusion dyes are provided to the cells at a concentration ranging from about 100 ng/ml to about 5 µg/ml, with from about 500 ng/ml to about 1 µg/ml being preferred. A wash step may or may not be used. In a preferred embodiment, a candidate bioactive agent is combined with the cells as described herein. The cells and the inclusion dye are incubated for some period of time, to allow cell division and thus dye dilution.

Assays for the level of surface Ig expression in resting cells, preferably Ramos cells or primary B-cells, may also be done. The methods involve a first step of screening for an agent capable of binding to Hck, or capable of modulating the binding of Hck to Hck binding partner, or capable of modualting Hck activity, and a second step of contacting such an agent to a Ramos cell, or other B-cell line cell, or primary B-cell, and determining the level of surface Ig expression. An agent that reduces the basal level of surface Ig is particularly preferred.

Without being bound by theory, it is recognized herein that Hck proteins are involved in the regulation of signal transduction in lymphocytes and platelets. Particularly, Hck proteins are recognized herein as being critical regulators of B-cell and T-cell activation, as well as platelet proliferation. As discussed above, the activation of specific signaling pathways in lymphocytes determines the quality, magnitude, and duration of immune responses. In transplantation, acute and chronic inflammatory diseases, and autoimmunity, it is these pathways that are responsible for the induction, maintenance and exacerbation of undesirable lymphocyte responses.

Accordingly, in one aspect, the invention provides compositions and methods for the treatment of lymphocyte activation disorders and platelet activation or proliferation disorders, as described below.

In a preferred embodiment, the present invention provides Hck proteins and nucleic acids, as well as agents that bind to them and/or modulate their activity, including and preferably small molecule chemical compositions as discussed herein, which are useful in the treatment of acute and chronic inflammatory diseases and autoimmune diseases, as well as in the treatment of a host receiving a transplant. Among these diseases are those listed in FIG. 6.

In another preferred embodiment, the present invention provides Hck proteins and nucleic acids, as well as agents that bind to them and/or modulate their activity, including and preferably small molecule chemical compositions as discussed herein, which are useful in the treatment of physiological states that are characterized by or lead to the presentation of some or all symptoms characteristic of acute inflammatory disease, chronic inflammatory disease, autoimmune disease, or response to transplantation.

It will be understood that these diseases and states may or may not be associated with altered Hck activity. That is, Hck compositions (proteins, nucleic acids, anti-Hck antibodies, agonists, antagonists) find use in the prevention and/or treatment of diseases and states which do not have Hck dysregulation or dysfunction as a molecular basis, but still involve lymphocyte activation or platelet proliferation. That is, a disease or state need not be associated with Hck activity for the present compositions and methods to be useful in preventing or treating it. Many autoimmune diseases fall into this category.

In another preferred embodiment, the present invention provides Hck proteins and nucleic acids, as well as agents that bind to them and/or modulate their activity, including and preferably small molecule chemical compositions as discussed herein, which are useful as prophylactics for the prevention of acute inflammatory disease, chronic inflammatory disease, autoimmune disease, and response to transplantation.

In a preferred embodiment, the present invention provides Hck proteins and nucleic acids, as well as agents that bind to them and/or modulate their activity, including and preferably small molecule chemical compositions as discussed herein, which are useful as prophylactics for the prevention of physiological states that are characterized by or least to the presentation of some or all symptoms characteristic of acute inflammatory disease, chronic inflammatory disease, autoimmune disease, or response to transplantation.

In a preferred embodiment, Hck proteins and nucleic acids provided herein are useful for the inhibition of antigen receptor-induced lymphocyte activation, as characterized by the induction of CD69, CD23, and other markers of activation. Particularly useful for this purpose is a dominant negative Hck protein lacking a tyrosine kinase domain and comprising amino acids 1–211, 1–230, or 62–211 in SEQ ID NO:2, or an amino acid sequence having at least about 85%, more preferably 90%, more preferably 95%, more preferably 98% identity to these sequence. Also preferred are kinase dead Hck proteins which comprise a tyrosine kinase domain but lack a catalytic lysine residue therein. Preferred Hck point mutants are K269E and K269M, relating to SEQ ID NO:2. Antisense Hck nucleic acids are also preferred for this purpose. Double stranded nucleic acids for use in RNA interference (see Caplan, Trends in Biotechnology, 20: 49–51, 2002) are also preferred for this purpose. Intrabodies which specifically bind to Hck are als preferred. Hck antagonists identified by the methods herein, including and preferably small molecule chemical compounds, are especially preferred for this purpose.

In an especially preferred embodiment, Hck proteins and nucleic acids provided herein are useful for the inhibition of immunoglobulin production by B lymphocytes that normally results from BCR activation by antigen. Particularly useful for this purpose is a dominant negative Hck protein lacking a tyrosine kinase domain and comprising amino acids 1–211, 1–230, or 62–211 in SEQ ID NO:2, or an amino acid sequence having at least about 85%, more preferably 90%, more preferably 95%, more preferably 98% identity to these sequences. Also preferred are kinase dead Hck proteins which comprise a tyrosine kinase domain but lack a catalytic lysine residue therein. Antisense Hck nucleic acids are also preferred for this purpose. Double stranded nucleic acids for use in RNA interference (see Caplan, Trends in Biotechnology, 20: 49–51, 2002) are also preferred for this purpose. Hck antagonists identified by the methods herein, including and preferably small molecule chemical compounds, are especially preferred for this purpose.

In another embodiment, the present invention provides Hck proteins and nucleic acids, as well as agents that bind to them and/or modulate their activity, including and preferably small molecule chemical compositions as discussed herein, which are useful for the treatment of platelet proliferation disorders such as Wiskott Aldrich syndrome.

Without being bound by theory, Hck proteins, being mediators of signal transduction in lymphocytes, particularly signal transduction events underlying lymphocyte activation, are involved in the regulation of proliferation of lymphocytes, and have utility as modulators of lymphocyte proliferation. Further, disorders associated with Hck dysfunction or dysregulation include lymphocyte proliferation disorders, such as leukemias, lymphomas, and Wiskott-Aldrich syndrome.

Accordingly, in a preferred embodiment, the present invention provides Hck proteins and nucleic acids, as well as agents capable of binding to them or modulating their activity, including and preferably small molecule chemical compositions as discussed herein, which are useful in the treatment of disorders involving T-cell and B-cell proliferation, including leukemias, lymphomas, and Wiskott-Aldrich syndrome.

Without being bound by theory, Hck proteins, being mediators of signal transduction in platelets, are involved in the regulation of proliferation of platelets, and have utility as modulators of platelet proliferation. Further, disorders associated with Hck dysfunction or dysregulation include platelet proliferation disorders, such as Wiskott-Aldrich syndrome.

It is recognized in the art that signaling pathways involved in the regulation of cell proliferation frequently participate in, directly or indirectly, the regulation of cell survival and programmed cell death. It is further recognized in the art that the dysregulation of mechanisms of programmed cell death can lead to cancer, particularly in lymphocytes. For example, overexpression of Bcl-2, which promotes cell survival through the inhibition of apoptotic processes, is thought to be responsible for the survival of excessive numbers of lymphocytes in a form of lymphoma (Reed et al., Science, 236:1295–1299, 1987; Tsujimoto et al., Science, 228:1440–1443, 1985).

Accordingly, the present invention provides Hck proteins and nucleic acids, as well as agents capable of binding to them and/or modulating their activity, including and preferably small molecule chemical compositions as discussed herein, which are useful in the treatment of disorders involving T-cell and B-cell survival and programmed cell death, including cancer.

The proteins and nucleic acids provided herein can also be used for screening purposes wherein the protein-protein interactions of the Hck proteins can be identified. Genetic systems have been described to detect protein-protein interactions. The first work was done in yeast systems, namely the "yeast two-hybrid" system. The basic system requires a protein-protein interaction in order to turn on transcription of a reporter gene. Subsequent work was done in mammalian cells. See Fields et al., Nature 340:245 (1989); Vasavada et al., PNAS USA 88:10686 (1991); Fearon et al., PNAS USA 89:7958 (1992); Dang et al., Mol. Cell. Biol. 11:954 (1991); Chien et al., PNAS USA 88:9578 (1991); and U.S. Pat. Nos. 5,283,173, 5,667,973, 5,468,614, 5,525,490, and 5,637,463. A preferred system is described in Ser. Nos.

09/050,863, filed Mar. 30, 1998 and 09/359,081 filed Jul. 22, 1999, entitled "Mammalian Protein Interaction Cloning System". For use in conjunction with these systems, a particularly useful shuttle vector is described in Ser. No. 09/133,944, filed Aug. 14, 1998, entitled "Shuttle Vectors".

In general, two nucleic acids are transformed into a cell, where one is a "bait" such as the gene encoding an Hck protein or a portion thereof, and the other encodes a test candidate. Only if the two expression products bind to one another will an indicator, such as a fluorescent protein, be expressed. Expression of the indicator indicates when a test candidate binds to the Hck protein, and identifies the candidate as being part of a T-cell, B-cell, or platelet Hck signaling pathway. A test candidate so identified may then be used as bait to identify binding proteins that are also identified as being part of a T-cell, B-cell, or platelet Hck signaling pathway. Additionally, Hck proteins may be used to identify new baits, or agents that bind to Hck proteins. Additionally, the two-hybrid system can be used wherein a test candidate is added in addition to the bait and the Hck protein encoding nucleic acids to determine agents which interfere with the binding of bait to the Hck protein.

In one embodiment, a mammalian two-hybrid system is preferred. Mammalian systems provide post-translational modifications of proteins which may contribute significantly to their ability to interact. In addition, a mammalian two-hybrid system can be used in a wide variety of mammalian cell types to mimic the regulation, induction, processing, etc. of specific proteins within a particular cell type. For example, proteins involved in a disease state (i.e., cancer, apoptosis related disorders) could be tested in the relevant disease cells. Similarly, for testing of random proteins, assaying them under the relevant cellular conditions will give the highest positive results. Furthermore, the mammalian cells can be tested under a variety of experimental conditions that may affect intracellular protein-protein interactions, such as in the presence of hormones, drugs, growth factors and cytokines, radiation, chemotherapeutics, cellular and chemical stimuli, etc., that may contribute to conditions which can affect protein-protein interactions.

Assays involving binding such as the two-hybrid system may take into account non-specific binding proteins (NSB).

Expression in various cell types, and assays for Hck activity are described above. The activity assays can be performed to confirm the activity of Hck proteins which have already been identified by their sequence identity/similarity to Hck (SEQ ID NO:2), as well as to further confirm the activity of lead compounds identified as modulators of Hck activity.

The components provided herein for the assays provided herein may also be combined to form kits. The kits can be based on the use of Hck proteins and/or nucleic acids encoding Hck proteins. In one embodiment, other components are provided in the kit. Such components include one or more of packaging, instructions, antibodies, and labels. Additional assays such as those used in diagnostics are further described below.

Bioactive agents may be identified by the methods provided herein. Compounds with pharmacological activity are able to enhance or interfere with the activity of the Hck protein. The compounds having the desired pharmacological activity may be administered in a physiologically acceptable carrier to a host, as further described below.

The present discovery relating to the role of Hck proteins in leukocytes thus provides methods for inducing or preventing leukocyte activation and platelet proliferation. In a preferred embodiment, methods for inducing or inhibiting lymphocyte activation and platelet proliferation are provided. In a preferred embodiment, the Hck proteins, and particularly Hck protein fragments, are useful in the study or treatment of conditions which involve dysfunction or dysregulation of Hck protein activity, i.e. to diagnose, treat or prevent Hck associated disorders. "Hck associated disorders" or "disease states" or "physiological states associated with Hck dysfunction or dysregulation" include conditions involving insufficient, excessive, and inappropriate Hck activity. Among these disorders are lymphocyte activation disorders and platelet proliferation disorders.

Thus, in one embodiment, methods for regulating lymphocyte activation in cells or organisms are provided. In one embodiment, the methods comprise administering to a cell or individual, an Hck protein in a therapeutic amount. Alternatively, an anti-Hck antibody that reduces or eliminates the biological activity of the endogenous Hck protein is administered. Particularly preferred are intrabodies, which are useful for the inhibition of intracellular Hck protein in situ. The use of intrabodies is known in the art, for example, see Marasco, Curr. Top. Microbiol. Immunol. 260:247–270, 2001. Alternatively and preferably an Hck dominant negative protein variant is administered. In another preferred embodiment, a bioactive agent as identified by the methods provided herein is administered. In a further preferred embodiment, a small molecule chemical composition which inhibits Hck activity is administered. Alternatively, the methods comprise administering to a cell or individual a recombinant nucleic acid encoding an Hck protein. In one embodiment, nucleic acid encoding an Hck dominant negative variant protein is administered. In another embodiment, an Hck antisense nucleic acid is administered. In another embodiment, an Hck RNAi is administered. RNAi's are well known in the art, for example, see Caplan, Trends in Biotechnology, 20: 49–51, 2002.

In one embodiment, the activity of Hck is increased. As will be appreciated by those in the art, this may be accomplished in any number of ways. In a preferred embodiment, the activity of Hck is increased by increasing the amount of Hck in the cell, for example by overexpressing the endogenous Hck or by administering a gene encoding an Hck protein, using known gene-therapy techniques, for example. In a preferred embodiment, the gene therapy techniques include the incorporation of the exogenous gene using enhanced homologous recombination (EHR), for example as described in PCT/US93/03868, hereby incorporated by reference in its entirety. Alternatively, Hck activity may be increased by administering an agent determined to increase Hck activity or expression by the methods provided herein.

In one embodiment, the activity of Hck is decreased. As will be appreciated by those in the art, this may be accomplished in any number of ways. In a preferred embodiment, the activity of Hck is decreased by decreasing the amount of Hck mRNA in the cell, for example by expressing Hck antisense RNA. Double stranded nucleic acids for use in RNA interference (see Caplan, Trends in Biotechnology, 20: 49–51, 2002) are also preferred for this purpose. Alternatively, endogenous Hck activity is decreased by administering a dominant negative Hck protein or a gene encoding a dominant negative Hck protein. Alternatively, endogenous Hck activity is decreased by administering anti-Hck antibody or a gene encoding anti-Hck antibody or an epitope recognizing portion thereof. Particularly preferred are intrabodies, which are useful for the inhibition of intracellular Hck protein in situ. Known gene-therapy techniques may be used to administer these agents. In a preferred embodiment, the gene therapy techniques involve incorporation of the exogenous gene into the host genome using enhanced homologous recombination (EHR), for example as described in PCT/US93/03868, hereby incorporated by reference in its entirety. Alternatively, Hck activity may be decreased by administering an agent determined to decrease Hck activity or expression by the methods provided herein.

It appears that Hck protein is an important protein in leukocyte activation, particularly lymphocyte activation and platelet proliferation. Accordingly, disorders based on mutant or variant Hck genes may be determined. In one embodiment, the invention provides methods for identifying cells containing variant Hck genes comprising determining all or part of the sequence of at least one endogenous Hck gene in a cell. As will be appreciated by those in the art, this may be done using any number of sequencing techniques. In a preferred embodiment, the invention provides methods of identifying the Hck genotype of an individual comprising determining all or part of the sequence of at least one Hck gene of the individual. This is generally done in at least one tissue of the individual, and may include the evaluation of a number of tissues or different samples of the same tissue. The method may include comparing the sequence of the sequenced Hck gene to a known Hck gene, i.e. a wild-type gene.

The sequence of all or part of the Hck gene can then be compared to the sequence of a known Hck gene to determine if any differences exist. This can be done using any number of known sequence identity programs, such as Bestfit, etc. In a preferred embodiment, the presence of a difference in the sequence between the Hck gene of the patient and the known Hck gene is indicative of a disease state or a propensity for a disease state, particularly a lymphocyte activation disorder ot a platelet proliferation disorder.

In one embodiment, the invention provides methods for diagnosing an Hck related condition in an individual. The methods comprise measuring the activity of Hck in a tissue from the individual or patient, which may include a measurement of the amount or specific activity of an Hck protein. This activity is compared to the activity of Hck from either an unaffected second individual or from an unaffected tissue from the first individual. When these activities are different, the first individual may be at risk for an Hck associated disorder. In this way, for example, monitoring of various disease conditions may be done by monitoring the absolute Hck activity in a sample or the specific activity of an Hck protein from a sample. Similarly, activity levels may correlate with prognosis.

In a preferred embodiment, Hck activity levels are determined in lymphocytes of an affected individual. In another preferred embodiment, Hck activity levels are determined in platelets of an affected individual.

In one aspect, the expression levels of Hck genes (encoding Hck proteins) are determined in different patient samples or cells for which either diagnostic or prognostic information is desired. Gene expression monitoring is done on genes encoding Hck proteins. In one aspect, the expression levels of Hck genes are determined for different cellular states, such as normal cells and activated cells. By comparing Hck gene expression levels in cells in different states, information including both up- and down-regulation of Hck genes is obtained, which can be used in a number of ways. For example, the evaluation of a particular treatment regime may be evaluated: does a chemotherapeutic drug act to improve the long-term prognosis in a particular patient. Similarly, diagnosis may be done or confirmed by comparing patient samples. Furthermore, these gene expression levels allow screening of drug candidates with an eye to mimicking or altering a particular expression level. This may be done by making biochips comprising probes that determine the presence of Hck genes, which biochips can be used in these screens. These methods can also be done on the protein basis; that is, Hck protein expression levels can be evaluated for diagnostic and prognostic purposes or to screen candidate agents for their effects on Hck protein expression. ELISA methods, and array-based protein detection methods are know to those skilled in the art.

In a preferred embodiment, Hck expression levels are determined in lymphocytes in the presence of candidate agents. This determination is done to screen for agents capable of reducing Hck expression, which find use as immunosuppressants and as agents for the inhibition of immunoglobulin production by B-lymphocytes.

In a preferred embodiment, nucleic acid probes to Hck nucleic acids and their complements are made. The nucleic acid probes are designed to be substantially complementary to Hck nucleic acids, i.e., the target sequence, such that hybridization of the target sequence and the probe occurs. As outlined below, this complementarity need not be perfect; there may be any number of base pair mismatches which will interfere with hybridization between the target sequence and the single stranded nucleic acids of the present invention. However, if the number of mismatches is so great that no hybridization can occur under even the least stringent of hybridization conditions, the sequence is not a complementary target sequence. Thus, by "substantially complementary" herein is meant that the probes are sufficiently complementary to the target sequences to hybridize under normal reaction conditions, particularly high stringency conditions, as outlined herein.

A "nucleic acid probe" is generally single stranded but can be partially single and partially double stranded. The strandedness of the probe is dictated by the structure, composition, and properties of the target sequence. In general, the nucleic acid probes range from about 8 to about 100 bases long, with from about 10 to about 80 bases being preferred, and from about 30 to about 50 bases being particularly preferred. In some embodiments, much longer nucleic acids can be used, up to hundreds of bases (e.g., whole genes).

As will be appreciated by those in the art, nucleic acids can be attached or immobilized to a solid support in a wide variety of ways. By "immobilized" and grammatical equivalents herein is meant the association or binding between the nucleic acid probe and the solid support is sufficient to be stable under the conditions of binding, washing, analysis, and removal. The binding can be covalent or non-covalent. By "non-covalent binding" and grammatical equivalents herein is meant one or more of either electrostatic, hydrophilic, and hydrophobic interactions. Included in non-covalent binding is the covalent attachment of a molecule, such as, streptavidin to the support and the non-covalent binding of the biotinylated probe to the streptavidin. By "covalent binding" and grammatical equivalents herein is meant that the two moieties, the solid support and the probe, are attached by at least one bond, including sigma bonds, pi bonds and coordination bonds. Covalent bonds can be formed directly between the probe and the solid support or can be formed by a cross linker or by inclusion of a specific reactive group on either the solid support or the probe or both molecules. Immobilization may also involve a combination of covalent and non-covalent interactions.

In general, the probes are attached to the biochip in a wide variety of ways, as will be appreciated by those in the art. As described herein, the nucleic acids can either be synthesized first, with subsequent attachment to the biochip, or can be directly synthesized on the biochip.

The biochip comprises a suitable solid substrate. By "substrate" or "solid support" or other grammatical equivalents herein is meant any material that can be modified to contain discrete individual sites appropriate for the attachment or association of the nucleic acid probes and is amenable to at least one detection method. As will be appreciated by those in the art, the number of possible substrates are very large, and include, but are not limited to, glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses, plastics, etc. In general, the substrates allow optical detection and do not appreciably show fluorescence.

In a preferred embodiment, the surface of the biochip and the probe may be derivatized with chemical functional groups for subsequent attachment of the two. Thus, for example, the biochip is derivatized with a chemical functional group including, but-not limited to, amino groups, carboxy groups, oxo groups and thiol groups, with amino groups being particularly preferred. Using these functional groups, the probes can be attached using functional groups on the probes. For example, nucleic acids containing amino groups can be attached to surfaces comprising amino groups, for example using linkers as are known in the art; for example, homo-or hetero-bifunctional linkers as are well known (see 1994 Pierce Chemical Company catalog, technical section on cross-linkers, pages 155–200, incorporated herein by reference). In addition, in some cases, additional linkers, such as alkyl groups (including substituted and heteroalkyl groups) may be used.

In this embodiment, oligonucleotides, corresponding to the nucleic acid probe, are synthesized as is known in the art, and then attached to the surface of the solid support. As will be appreciated by those skilled in the art, either the 5' or 3' terminus may be attached to the solid support, or attachment may be via an internal nucleoside.

In an additional embodiment, the immobilization to the solid support may be very strong, yet non-covalent. For example, biotinylated oligonucleotides can be made, which bind to surfaces covalently coated with streptavidin, resulting in attachment.

Alternatively, the oligonucleotides may be synthesized on the surface, as is known in the art. For example, photoactivation techniques utilizing photopolymerization compounds and techniques are used. In a preferred embodiment, the nucleic acids can be synthesized in situ, using well known photolithographic techniques, such as those described in WO 95/25116; WO 95/35505; U.S. Pat. Nos. 5,700,637 and 5,445,934; and references cited within, all of which are expressly incorporated by reference; these methods of attachment form the basis of the Affimetrix GeneChip™ technology.

"Differential expression," or grammatical equivalents as used herein, refers to both qualitative as well as quantitative differences in the genes' temporal and/or cellular expression patterns within and among the cells. Thus, a differentially expressed gene can qualitatively have its expression altered, including an activation or inactivation, in, for example, a normal versus an apoptotic cell. That is, genes may be turned on or turned off in a particular state, relative to another state. As is apparent to the skilled artisan, any comparison of two or more states can be made. Such a qualitatively regulated gene will exhibit an expression pattern within a state or cell type which is detectable by standard techniques in one such state or cell type, but is not detectable in both. Alternatively, the determination is quantitative in that expression is increased or decreased; that is, the expression of the gene is either upregulated, resulting in an increased amount of transcript, or downregulated, resulting in a decreased amount of transcript. The degree to which expression differs need only be large enough to quantify via standard characterization techniques, such as by use of Affymetrix GeneChip™ expression arrays, Lockhart, Nature Biotechnology 14:1675–1680 (1996), hereby expressly incorporated by reference. Other techniques include, but are not limited to, quantitative reverse transcriptase PCR, Northern analysis and RNase protection.

Though discussed above with respect to transcripts, it will be appreciated by those in the art that this may be done by evaluation at either the gene transcript, or the protein level; that is, the amount of gene expression may be monitored using nucleic acid probes to the DNA or RNA gene transcript, and the quantification of gene expression levels, or, alternatively, the final gene product itself (protein) can be monitored, for example through the use of antibodies to the Hck protein and standard immunoassays (ELISAs, etc.) or other techniques, including mass spectroscopy assays, 2D gel electrophoresis assays, etc.

In another method detection of the mRNA is performed in situ. In this method permeabilized cells or tissue samples are contacted with a detectably labeled nucleic acid probe for sufficient time to allow the probe to hybridize with the target mRNA. Following washing to remove the non-specifically bound probe, the label is detected. For example a digoxygenin labeled riboprobe (RNA probe) that is complementary to the mRNA encoding an Hck protein is detected by binding the digoxygenin with an anti-digoxygenin secondary antibody and exposing to nitro blue tetrazolium and 5-bromo-4-chloro-3-indoyl phosphate.

In another preferred method, expression of Hck protein is determined using in situ imaging techniques employing antibodies to Hck proteins. In this method cells are contacted with from one to many antibodies to the Hck protein(s). Following washing to remove non-specific antibody binding, the presence of the antibody or antibodies is detected. In one embodiment the antibody is detected by incubating with a secondary antibody that contains a detectable label. In another method the primary antibody to the Hck protein(s) contains a detectable label. In another preferred embodiment each one of multiple primary antibodies contains a distinct and detectable label. This method finds particular use in simultaneous screening for a plurality of Hck proteins. The label may be detected in a fluorometer which has the ability to detect and distinguish emissions of different wavelengths. Labels may be detected using a fluorescence microscope which has multiple fluorescence channels. In addition, a fluorescence activated cell sorter (FACS) can be used in this method. As will be appreciated by one of ordinary skill in the art, numerous other histological imaging techniques are useful in the invention and the antibodies can also be used in ELISA, immunoblotting (Western blotting), immunoprecipitation, BIACORE technology, and the like.

In one embodiment, the Hck proteins of the present invention may be used to generate polyclonal and monoclonal antibodies to Hck proteins, which are useful as described herein. Similarly, the Hck proteins can be coupled, using standard technology, to affinity chromatography columns. These columns may then be used to purify Hck antibodies. In a preferred embodiment, the antibodies are generated to epitopes unique to the Hck protein; that is, the antibodies show little or no cross-reactivity to other proteins. These antibodies find use in a number of applications. For example, the Hck antibodies may be coupled to standard affinity chromatography columns and used to purify Hck proteins as further described below. The antibodies may also be used as blocking polypeptides, as outlined above, since they will specifically bind to the Hck protein.

The anti-Hck protein antibodies may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the Hck protein or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid a, synthetic trehalose dicorynomycolate). The immunization protocol may be selected by one skilled in the art without undue experimentation.

The anti-Hck protein antibodies may, alternatively, be monoclonal antibodies. Monoclonal antibodies may be prepared using hybridoma methods, such as those described by Kohler and Milstein, *Nature*, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include the Hck protein or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell [Goding, *Monoclonal Antibodies: Principles and Practice*, Academic Press, (1986) pp. 59–103]. Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromyeloma cell lines also have been described for the production of human monoclonal antibodies [Kozbor, *J. Immunol.*, 133:3001 (1984); Brodeur et al., *Monoclonal Antibody Production Techniques and Applications*, Marcel Dekker, Inc., New York, (1987) pp. 51–63].

The culture medium in which the hybridoma cells are cultured can then be assayed for the presence of monoclonal antibodies directed against Hck protein. Preferably, the binding specificity of monoclonal antibodies produced by the hybridoma cells is determined by immunoprecipitation or by an in vitro binding assay, such as radioimmunoassay (RIA) or enzyme-linked immunosorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones may be subcloned by limiting dilution procedures and grown by standard methods [Goding, supra]. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein a-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences [U.S. Pat. No. 4,816,567; Morrison et al., supra] or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art.

Alternatively, intrabodies may be prepared that are capable of binding to Hck intracellularly. Wirtz et al., Prot. Sci. 8(11):2245–50 (1999); Ohage et al. J. Mol. Biol. 291 (5):1129–34 and Ohage et al. J. Biol. Chem. 291(5): 1119–28 (1999), the disclosures of which are expressly incorporated by reference herein. Preferably such intrabodies are lipid soluble and lack a constant region. Intrabodies are particularly useful for the treatment of lymphocyte activation disorders, including those associated with Hck dysregulation or dysfunction.

The anti-Hck protein antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., *Nature*, 321:522–525 (1986); Riechmann et al., *Nature*, 332:323–329 (1988); and Presta, *Curr. Op. Struct. Biol.*, 2:593–596 (1992)].

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers [Jones et al., *Nature*, 321:522–525 (1986); Riechmann et al., *Nature*, 332:323–327 (1988); Verhoeyen et al., *Science*, 239:1534–1536 (1988)], by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries [Hoogenboom and Winter, *J. Mol. Biol.*, 227:381 (1991); Marks et al., *J. Mol. Biol.*, 222:581 (1991)]. The techniques of Cole et al. and Boerner et al. are also available for the preparation of human monoclonal antibodies (Cole et al., *Monoclonal Antibodies and Cancer Therapy*, Alan R. Liss, p. 77 (1985) and Boerner et al., *J. Immunol.*, 147(1):86–95 (1991). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., *Bio/Technology* 10, 779–783 (1992); Lonberg et al., *Nature* 368 856–859 (1994); Morrison, *Nature* 368, 812–13 (1994);Fishwild et al., *Nature Biotechnology* 14, 845–51 (1996); Neuberger, *Nature Biotechnology* 14, 826 (1996); Lonberg and Huszar, *Intern. Rev. Immunol.* 13 65–93 (1995).

Bispecific antibodies are monoclonal, preferably human or humanized, antibodies that have binding specificities for at least two different antigens. In the present case, one of the binding specificities is for the Hck protein, the other one is for any other antigen, and preferably for a cell-surface protein or receptor or receptor subunit, preferably for a protein on the surface of a dysregulated or dysfunctional lymphocyte or platelet.

Methods for making bispecific antibodies are known in the art. Traditionally, the recombinant production of bispecific antibodies is based on the co-expression of two immunoglobulin heavy-chain/light-chain pairs, where the two heavy chains have different specificities [Milstein and Cuello, *Nature*, 305:537–539 (1983)]. Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., *EMBO J.* 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., *Methods in Enzymology*, 121:210 (1986).

Heteroconjugate antibodies are also within the scope of the present invention. Heteroconjugate antibodies are composed of two covalently joined antibodies. Such antibodies have, for example, been proposed to target immune system cells to unwanted cells [U.S. Pat. No. 4,676,980], and for treatment of HIV infection [WO 91/00360; WO 92/200373; EP 03089]. It is contemplated that the antibodies may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

The anti-Hck protein antibodies of the invention have various utilities. For example, anti-Hck protein antibodies may be used in diagnostic assays for an Hck protein, e.g., detecting its expression in specific cells, tissues, or serum. Various diagnostic assay techniques known in the art may be used, such as, for example, competitive binding assays, direct or indirect sandwich assays, and immunoprecipitation assays conducted in either heterogeneous or homogeneous phases [Zola, *Monoclonal Antibodies: a Manual of Techniques,* CRC Press, Inc. (1987) pp. 147–158]. The antibodies used in the diagnostic assays can be labeled with a detectable moiety. The detectable moiety should be capable of producing, either directly or indirectly, a detectable signal. For example, the detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galactosidase or horseradish peroxidase. Any method known in the art for conjugating the antibody to the detectable moiety may be employed, including those methods described by Hunter et al., *Nature,* 144:945 (1962); David et al., *Biochemistry,* 13:1014 (1974); Pain et al., *J. Immunol. Meth.,* 40:219 (1981); and Nygren, *J. Histochem. and Cytochem.,* 30:407 (1982).

Anti-Hck protein antibodies also are useful for the affinity purification of Hck protein from recombinant cell culture or natural sources. In this process, the antibodies against Hck protein are immobilized on a suitable support, such a Sephadex resin or filter paper, using methods well known in the art. The immobilized antibody then is contacted with a sample containing the Hck protein to be purified, and thereafter the support is washed with a suitable solvent that will remove substantially all the material in the sample except the Hck protein, which is bound to the immobilized antibody. Finally, the support is washed with another suitable solvent that will release the Hck protein from the antibody.

The anti-Hck protein antibodies may also be used in treatment. In one embodiment, the genes encoding the antibodies are provided, such that the antibodies bind to and modulate the Hck protein within the cell.

In one embodiment, a therapeutically effective dose of an Hck protein, agonist or antagonist is administered to a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for Hck protein degradation, systemic versus localized delivery, as well as the age, body weight, general health, sex, diet, time of administration, drug interaction and the severity of the condition may be necessary, and will be ascertainable with routine experimentation by those skilled in the art.

A "patient" for the purposes of the present invention includes both humans and other animals, particularly mammals. Thus the methods are applicable to both human therapy and veterinary applications. In the preferred embodiment the patient is a mammal, and in the most preferred embodiment the patient is human.

The administration of the Hck protein, agonist or antagonist of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the composition may be directly applied as a solution or spray. Depending upon the manner of introduction, the compounds may be formulated in a variety of ways. The concentration of therapeutically active compound in the formulation may vary from about 0.1–100% wt.

The pharmaceutical compositions of the present invention comprise an Hck protein, agonist or antagonist (including antibodies and bioactive agents as described herein, most preferably small molecule chemical compositions as described herein) in a form suitable for administration to a patient. In the preferred embodiment, the pharmaceutical compositions are in a water soluble form, such as being present as pharmaceutically acceptable salts, which is meant to include both acid and base addition salts. "Pharmaceutically acceptable acid addition salt" refers to those salts that retain the biological effectiveness of the free bases and that are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, and ethanolamine.

The pharmaceutical compositions may also include one or more of the following: carrier proteins such as serum albumin; buffers; fillers such as microcrystalline cellulose, lactose, corn and other starches; binding agents; sweeteners and other flavoring agents; coloring agents; and polyethylene glycol. Additives are well known in the art, and are used in a variety of formulations.

Combinations of the compositions may be administered. Moreover, the compositions may be administered in combination with other therapeutics, including growth factors or chemotherapeutics and/or radiation. Targeting agents (i.e. ligands for receptors on cancer cells) may also be combined with the compositions provided herein.

In one embodiment provided herein, the antibodies are used for immunotherapy, thus, methods of immunotherapy are provided. By "immunotherapy" is meant treatment of Hck protein related disorders with an antibody raised against an Hck protein. Immunotherapy may also be used to treat lymphocyte disorders not associated with Hck activity, but treatable by Hck modulation. As used herein, immunotherapy can be passive or active. Passive immunotherapy, as defined herein, is the passive transfer of antibody to a recipient (patient). Active immunization is the induction of antibody and/or T-cell responses in a recipient (patient). Induction of an immune response can be the consequence of providing the recipient with an Hck protein antigen to which antibodies are raised. As appreciated by one of ordinary skill in the art, the Hck protein antigen may be provided by injecting an Hck protein against which antibodies are desired to be raised into a recipient, or contacting the recipient with an Hck protein nucleic acid, capable of expressing the Hck protein antigen, under conditions for expression of the Hck protein antigen.

In a preferred embodiment, a therapeutic compound is conjugated to an antibody, preferably an Hck protein antibody. The therapeutic compound may be a cytotoxic agent. In this method, targeting the cytotoxic agent to apoptotic cells or tumor tissue or cells, results in a reduction in the number of afflicted cells, thereby reducing symptoms associated with apoptosis or cancer. Cytotoxic agents are numerous and varied and include, but are not limited to, cytotoxic drugs or toxins or active fragments of such toxins. Suitable toxins and their corresponding fragments include diptheria A chain, exotoxin A chain, ricin A chain, abrin A chain, curcin, crotin, phenomycin, enomycin and the like. Cytotoxic agents also include radiochemicals made by conjugating radioisotopes to antibodies raised against Hck proteins, or binding of a radionuclide to a chelating agent that has been covalently attached to the antibody.

In a preferred embodiment, Hck protein genes are administered as DNA vaccines, either single nucleic acids or combinations of Hck protein genes. Naked DNA vaccines are generally known in the art; see Brower, Nature Biotechnology 16:1304–1305 (1998). Methods for the use of nucleic acids as DNA vaccines are well known to one of ordinary skill in the art, and include placing an Hck protein gene or portion of an Hck protein nucleic acid under the control of a promoter for expression in a patient. The Hck protein gene used for DNA vaccines can encode full-length Hck proteins, but more preferably encodes portions of the Hck proteins including peptides derived from the Hck protein. In a preferred embodiment a patient is immunized with a DNA vaccine comprising a plurality of nucleotide sequences derived from an Hck protein gene. Similarly, it is possible to immunize a patient with a plurality of Hck protein genes or portions thereof, as defined herein. Without being bound by theory, following expression of the polypeptide encoded by the DNA vaccine, cytotoxic T-cells, helper T-cells and antibodies are induced which recognize and destroy or eliminate cells expressing Hck proteins.

In a preferred embodiment, the DNA vaccines include a gene encoding an adjuvant molecule with the DNA vaccine. Such adjuvant molecules include cytokines that increase the immunogenic response to the Hck protein encoded by the DNA vaccine. Additional or alternative adjuvants are known to those of ordinary skill in the art and find use in the invention.

The invention also includes the use of Hck protein compositions, Hck antagonists, or Hck antibodies, in the preparation of a medicament for the treatment of lymphocyte activation disorders and lymphocyte proliferation disorders.

All references cited herein are expressly incorporated by reference in their entirety. Moreover, all sequences displayed, cited by reference or accession number in the references are incorporated by reference herein.

We claim:

1. A method of screening for an immunosuppressant, comprising:
   a) combining a candidate bioactive agent, an HCK protein, and an HCK substrate protein, wherein said HCK protein comprises an amino acid sequence having at least about 95% identity to the amino acid sequence set forth in SEQ ID NO:2;
   b) detecting an inhibition of phosphorylation of said HCK substrate protein in the presence of said candidate bioactive agent;
   c) contacting said candidate bioactive agent to a lymphocyte;
   d) inducing activation of said lymphocyte; and
   e) determining the activation of said lymphocyte in the presence of said candidate bioactive agent;
   wherein said HCK protein will phosphorylate said HCK substrate protein in the absence of said candidate bioactive agent, and wherein a decrease in the activation of said lymphocyte in the presence of said candidate bioactive agent indicates that said candidate bioactive agent is an immunosuppressant.

2. The method of claim 1, wherein said HCK protein comprises the amino acid sequence set forth in SEQ ID NO:2.

3. The method of claim 1, wherein said HCK protein consists essentially of a tyrosine kinase domain.

4. A method of screening for an immunosuppressant, comprising:

a) combining a candidate bioactive agent, an HCK protein, and an HCK binding partner, wherein said HCK protein comprises an amino acid sequence having at least about 95% identity to the amino acid sequence set forth in SEQ ID NO:2, and wherein said HCK binding partner is selected from the group consisting of Nef, gp130, WASP, WIP, CD44, CD4, IL-2R, Btk, Bcr-abl, Ras-GAP, hBRAG, Ig-α, Ig-β, and p120Cbl;

b) detecting a decrease in the binding of said HCK protein to said HCK binding partner in the presence of said candidate bioactive agent;

c) contacting said candidate bioactive agent to a lymphocyte;

d) inducing activation of said lymphocyte; and e) determining the activation of said lymphocyte in the presence of said candidate bioactive agent;

wherein said HCK protein will bind to said HCK binding partner in the absence of said candidate bioactive agent, and wherein a decrease in the activation of said lymphocyte in the presence of said candidate bioactive agent indicates that said candidate bioactive agent is an immunosuppressant.

5. The method of claim 4, wherein said HCK protein comprises the amino acid sequence set forth in SEQ ID NO:2.

6. The method of claim 4, wherein said HCK protein consists essentially of an SH3 domain and an SH2 domain.

7. A method of screening for an immunosuppressant, comprising:

a) combining a candidate bioactive agent, and an HCK protein, wherein said HCK protein comprises an amino acid sequence having at least about 95% identity to the amino acid sequence set forth in SEQ ID NO:2;

b) detecting binding of said HCK protein to said candidate bioactive agent;

c) contacting said candidate bioactive agent to a lymphocyte;

d) inducing activation of said lymphocyte; and e) determining the activation of said lymphocyte in the presence of said candidate bioactive agent; wherein a decrease in the activation of said lymphocyte in the presence of said candidate bioactive agent indicates that said candidate bioactive agent is an immunosuppressant.

8. The method of claim 7, wherein said HCK protein comprises the amino acid sequence set forth in SEQ ID NO:2.

9. The method of claim 7, wherein said HCK protein consists essentially of an SH3 domain and an SH2 domain.

10. The method of any one of claims 4, and 7, wherein said candidate bioactive agent is a small molecule chemical compound from about 200 to about 500 daltons in size.

11. The method of any one of claims 1, 4, and 7, wherein said lymphocyte is a B lymphocyte.

12. The method of claim 11, wherein inducing the activation of said B lymphocyte is done by activating the B cell receptor (BCR).

13. The method of claim 11, wherein determining the activation of said lymphocyte comprises determining the activity of the immunoglobulin heavy chain gene (IgH) promoter.

14. The method of claim 11, wherein determining the activation of said lymphocyte comprises determining the expression of CD69.

15. The method of any one of claims 1, 4, and 7, wherein said lymphocyte is a T lymphocyte.

16. The method according to claim 15, wherein inducing the activation of said T lymphocyte is done by activating the T cell receptor (TCR).

17. The method of claim 15, wherein determining the activation of said lymphocyte comprises determining the expression of CD69.

18. The method of anyone of claims 1, 4, and 7, wherein a library of candidate bioactive agents is combined with said HCK protein.

19. The method of anyone of claims 1, 4, and 7, wherein determining the activation of said lymphocyte involves sorting said lymphocyte by FACS.

20. A method of screening for an immunosuppressant, comprising:

a) combining a candidate bioactive agent, an HCK protein, and an HCK substrate protein, wherein said HCK protein comprises an amino acid sequence having at least about 95% identity to the amino acid sequence set forth by residues 241–490, 24 1–505, or 230–505 in SEQ ID NO:2;

b) detecting an inhibition of phosphorylation of said HCK substrate protein in the presence of said candidate bioactive agent;

c) contacting said candidate bioactive agent to a lymphocyte;

d) inducing activation of said lymphocyte; and e) determining the activation of said lymphocyte in the presence of said candidate bioactive agent;

wherein said HCK protein will phosphorylate said HCK substrate protein in the absence of said candidate bioactive agent, and wherein a decrease in the activation of said lymphocyte in the presence of said candidate bioactive agent indicates that said candidate bioactive agent is an immunosuppressant.

21. The method of claim 20, wherein said HCK protein comprises the amino acid sequence set forth by residues 241–490, 241–505, or 230–505 in SEQ ID NO:2.

22. The method of claim 1, wherein said HCK substrate protein is selected from the group consisting of Bcr-abl, Ras-GAP, p120Cbl, WASP, WIP, and enolase.

23. A method of screening for an immunosuppressant, comprising:

a) combining a candidate bioactive agent, an HCK protein, and an HCK binding partner, wherein said HCK protein comprises an amino acid sequence having at least about 95% identity to the amino acid sequences set forth by residues 1–211, 1–230, or 62–211 in SEQ ID NO:2, and wherein said HCK binding partner is selected from the group consisting of Nef, gp130, WASP, WIP, CD44, CD4, IL-2R, Btk, Bcr-abl, Ras-GAP, hBRAG, Ig-α, Ig-β, and p120Cbl;

b) detecting a decrease in the binding of said HCK protein to said HCK binding partner in the presence of said candidate bioactive agent;

c) contacting said candidate bioactive agent to a lymphocyte;

d) inducing activation of said lymphocyte; and e) determining the activation of said lymphocyte in the presence of said candidate bioactive agent;

wherein said HCK protein will bind to said HCK binding partner in the absence of said candidate bioactive agent, and wherein a decrease in the activation of said lymphocyte in the presence of said candidate bioactive agent indicates that said candidate bioactive agent is an immunosuppressant.

24. The method of claim 23, wherein said HCK protein comprises the amino acid sequences set forth by residues 1–211, 1–230, or 62–211 in SEQ ID NO:2.

25. A method of screening for an immunosuppressant, comprising:
  a) combining a candidate bioactive agent, and an HCK protein, wherein said HCK protein comprises an amino acid sequence having at least about 95% identity to the amino acid sequences set forth by residues 1–211, 1–230, or 62–211 in SEQ ID NO:2;
  b) detecting binding of said HCK protein to said candidate bioactive agent;
  c) contacting said candidate bioactive agent to a lymphocyte;
  d) inducing activation of said lymphocyte; and
  e) determining the activation of said lymphocyte in the presence of said candidate bioactive agent; wherein a decrease in the activation of said lymphocyte in the presence of said
  candidate bioactive agent indicates that said candidate bioactive agent is an immunosuppressant.

26. The method of claim 25, wherein said HCK protein comprises the amino acid sequences set forth by residues 1–211, 1–230, or 62–211 in SEQ ID NO:2.

* * * * *

```
                        SEQUENCE LISTING

<160> NUMBER OF SEQ ID NOS: 2

<210> SEQ ID NO 1
<211> LENGTH: 1924
<212> TYPE: DNA
<213> ORGANISM: Homo sapiens
<220> FEATURE:
<221> NAME/KEY: CDS
<222> LOCATION: (78)..(1595)
<223> OTHER INFORMATION:

<400> SEQUENCE: 1
acctcagggg ctgccgagct ggggggggcgc tcaagctgcg aggatccggg ctgcccgcga      60
gacgaggagc gggcgcg atg ggg tgc atg aag tcc aag ttc ctc cag gtc       110
                   Met Gly Cys Met Lys Ser Lys Phe Leu Gln Val
                    1               5                  10 gga ggc aat aca ttc tca aaa act gaa acc agc gcc agc cca cac tgt      158
Gly Gly Asn Thr Phe Ser Lys Thr Glu Thr Ser Ala Ser Pro His Cys
                15                  20                  25 cct gtg tac gtg ccg gat ccc aca tcc acc atc aag ccg ggg cct aat      206
Pro Val Tyr Val Pro Asp Pro Thr Ser Thr Ile Lys Pro Gly Pro Asn
        30                  35                  40 agc cac aac agc aac aca cca gga atc agg gag gca ggc tct gag gac      254
Ser His Asn Ser Asn Thr Pro Gly Ile Arg Glu Ala Gly Ser Glu Asp
    45                  50                  55 atc atc gtg gtt gcc ctg tat gat tac gag gcc att cac cac gaa gac      302
Ile Ile Val Val Ala Leu Tyr Asp Tyr Glu Ala Ile His His Glu Asp
60                  65                  70                  75 ctc agc ttc cag aag ggg gac cag atg gtg gtc cta gag gaa tcc ggg      350
Leu Ser Phe Gln Lys Gly Asp Gln Met Val Val Leu Glu Glu Ser Gly
                80                  85                  90 gag tgg tgg aag gct cga tcc ctg gcc acc cgg aag gag ggc tac atc      398
Glu Trp Trp Lys Ala Arg Ser Leu Ala Thr Arg Lys Glu Gly Tyr Ile
```

```
                    95                  100                 105
cca agc aac tat gtc gcc cgc gtt gac tct ctg gag aca gag gag tgg    446
Pro Ser Asn Tyr Val Ala Arg Val Asp Ser Leu Glu Thr Glu Glu Trp
        110                 115                 120 ttt ttc aag ggc atc agc cgg aag gac gca gag cgc caa ctg ctg gct    494
Phe Phe Lys Gly Ile Ser Arg Lys Asp Ala Glu Arg Gln Leu Leu Ala
125                 130                 135 ccc ggc aac atg ctg ggc tcc ttc atg atc cgg gat agc gag acc act    542
Pro Gly Asn Met Leu Gly Ser Phe Met Ile Arg Asp Ser Glu Thr Thr
140                 145                 150                 155 aaa gga agc tac tct ttg tcc gtg cga gac tac gac cct cgg cag gga    590
Lys Gly Ser Tyr Ser Leu Ser Val Arg Asp Tyr Asp Pro Arg Gln Gly
                160                 165                 170 gat acc gtg aaa cat tac aag atc cgg acc ctg gac aac ggg ggc ttc    638
Asp Thr Val Lys His Tyr Lys Ile Arg Thr Leu Asp Asn Gly Gly Phe
            175                 180                 185 tac ata tcc ccc cga agc acc ttc agc act ctg cag gag ctg gtg gac    686
Tyr Ile Ser Pro Arg Ser Thr Phe Ser Thr Leu Gln Glu Leu Val Asp
        190                 195                 200 cac tac aag aag ggg aac gac ggg ctc tgc cag aaa ctg tcg gtg ccc    734
His Tyr Lys Lys Gly Asn Asp Gly Leu Cys Gln Lys Leu Ser Val Pro
205                 210                 215 tgc atg tct tcc aag ccc cag aag cct tgg gag aaa gat gcc tgg gag    782
Cys Met Ser Ser Lys Pro Gln Lys Pro Trp Glu Lys Asp Ala Trp Glu
220                 225                 230                 235 atc cct cgg gaa tcc ctc aag ctg gag aag aaa ctt gga gct ggg cag    830
Ile Pro Arg Glu Ser Leu Lys Leu Glu Lys Lys Leu Gly Ala Gly Gln
                240                 245                 250 ttt ggg gaa gtc tgg atg gcc acc tac aac aag cac acc aag gtg gca    878
Phe Gly Glu Val Trp Met Ala Thr Tyr Asn Lys His Thr Lys Val Ala
            255                 260                 265 gtg aag acg atg aag cca ggg agc atg tcg gtg gag gcc ttc ctg gca    926
Val Lys Thr Met Lys Pro Gly Ser Met Ser Val Glu Ala Phe Leu Ala
        270                 275                 280 gag gcc aac gtg atg aaa act ctg cag cat gac aag ctg gtc aaa ctt    974
Glu Ala Asn Val Met Lys Thr Leu Gln His Asp Lys Leu Val Lys Leu
285                 290                 295 cat gcg gtg gtc acc aag gag ccc atc tac atc atc acg gag ttc atg    1022
His Ala Val Val Thr Lys Glu Pro Ile Tyr Ile Ile Thr Glu Phe Met
300                 305                 310                 315 gcc aaa gga agc ttg ctg gac ttt ctg aaa agt gat gag ggc agc aag    1070
Ala Lys Gly Ser Leu Leu Asp Phe Leu Lys Ser Asp Glu Gly Ser Lys
                320                 325                 330 cag cca ttg cca aaa ctc att gac ttc tca gcc cag att gca gaa ggc    1118
Gln Pro Leu Pro Lys Leu Ile Asp Phe Ser Ala Gln Ile Ala Glu Gly
            335                 340                 345 atg gcc ttc atc gag cag agg aac tac atc cac cga gac ctc cga gct    1166
Met Ala Phe Ile Glu Gln Arg Asn Tyr Ile His Arg Asp Leu Arg Ala
        350                 355                 360 gcc aac atc ttg gtc tct gca tcc ctg gtg tgt aag att gct gac ttt    1214
Ala Asn Ile Leu Val Ser Ala Ser Leu Val Cys Lys Ile Ala Asp Phe
365                 370                 375 ggc ctg gcc cgg gtc att gag gac aac gag tac acg gct cgg gaa ggg    1262
Gly Leu Ala Arg Val Ile Glu Asp Asn Glu Tyr Thr Ala Arg Glu Gly
380                 385                 390                 395 gcc aag ttc ccc atc aag tgg aca gct cct gaa gcc atc aac ttt ggc    1310
Ala Lys Phe Pro Ile Lys Trp Thr Ala Pro Glu Ala Ile Asn Phe Gly
                400                 405                 410 tcc ttc acc atc aag tca gac gtc tgg tcc ttt ggt atc ctg ctg atg    1358
Ser Phe Thr Ile Lys Ser Asp Val Trp Ser Phe Gly Ile Leu Leu Met
```

```
Ser Phe Thr Ile Lys Ser Asp Val Trp Ser Phe Gly Ile Leu Leu Met
            415                 420                 425 gag atc gtc acc tac ggc cgg atc cct tac cca ggg atg tca aac cct    1406
Glu Ile Val Thr Tyr Gly Arg Ile Pro Tyr Pro Gly Met Ser Asn Pro
            430                 435                 440 gaa gtg atc cga gct ctg gag cgt gga tac cgg atg cct cgc cca gag    1454
Glu Val Ile Arg Ala Leu Glu Arg Gly Tyr Arg Met Pro Arg Pro Glu
            445                 450                 455 aac tgc cca gag gag ctc tac aac atc atg atg cgc tgc tgg aaa aac    1502
Asn Cys Pro Glu Glu Leu Tyr Asn Ile Met Met Arg Cys Trp Lys Asn
460                 465                 470                 475 cgt ccg gag gag cgg ccg acc ttc gaa tac atc cag agt gtg ctg gat    1550
Arg Pro Glu Glu Arg Pro Thr Phe Glu Tyr Ile Gln Ser Val Leu Asp
            480                 485                 490 gac ttc tac acg gcc aca gag agc cag tac caa cag cag cca tga        1595
Asp Phe Tyr Thr Ala Thr Glu Ser Gln Tyr Gln Gln Gln Pro
            495                 500                 505 tagggaggac cagggcaggg ccaggggtg cccaggtggt ggctgcaagg tggctccagc    1655
accatccgcc agggcccaca cccccttcct actcccagac acccaccctc gcttcagcca    1715
cagtttcctc atctgtccag tgggtaggtt ggactggaaa atctcttttt gactcttgca    1775
atccacaatc tgacattctc aggaagcccc caagttgata tttctatttc ctggaatggt    1835
tggattttag ttacagctgt gatttggaag ggaaactttc aaaatagtga aatgaatatt    1895
taaataaaag atataaatgc caaagtctt                                    1924

<210> SEQ ID NO 2
<211> LENGTH: 505
<212> TYPE: PRT
<213> ORGANISM: Homo sapiens

<400> SEQUENCE: 2

Met Gly Cys Met Lys Ser Lys Phe Leu Gln Val Gly Gly Asn Thr Phe
1               5                   10                  15

Ser Lys Thr Glu Thr Ser Ala Ser Pro His Cys Pro Val Tyr Val Pro
            20                  25                  30

Asp Pro Thr Ser Thr Ile Lys Pro Gly Pro Asn Ser His Asn Ser Asn
            35                  40                  45

Thr Pro Gly Ile Arg Glu Ala Gly Ser Glu Asp Ile Ile Val Val Ala
        50                  55                  60

Leu Tyr Asp Tyr Glu Ala Ile His His Glu Asp Leu Ser Phe Gln Lys
65              70                  75                  80

Gly Asp Gln Met Val Val Leu Glu Glu Ser Gly Glu Trp Trp Lys Ala
            85                  90                  95

Arg Ser Leu Ala Thr Arg Lys Glu Gly Tyr Ile Pro Ser Asn Tyr Val
            100                 105                 110

Ala Arg Val Asp Ser Leu Glu Thr Glu Glu Trp Phe Phe Lys Gly Ile
            115                 120                 125

Ser Arg Lys Asp Ala Glu Arg Gln Leu Leu Ala Pro Gly Asn Met Leu
            130                 135                 140

Gly Ser Phe Met Ile Arg Asp Ser Glu Thr Thr Lys Gly Ser Tyr Ser
145             150                 155                 160

Leu Ser Val Arg Asp Tyr Asp Pro Arg Gln Gly Asp Thr Val Lys His
            165                 170                 175

Tyr Lys Ile Arg Thr Leu Asp Asn Gly Gly Phe Tyr Ile Ser Pro Arg
            180                 185                 190
```

-continued

```
Ser Thr Phe Ser Thr Leu Gln Glu Leu Val Asp His Tyr Lys Lys Gly
            195                 200                 205

Asn Asp Gly Leu Cys Gln Lys Leu Ser Val Pro Cys Met Ser Ser Lys
        210                 215                 220

Pro Gln Lys Pro Trp Glu Lys Asp Ala Trp Glu Ile Pro Arg Glu Ser
225                 230                 235                 240

Leu Lys Leu Glu Lys Lys Leu Gly Ala Gly Gln Phe Gly Glu Val Trp
                245                 250                 255

Met Ala Thr Tyr Asn Lys His Thr Lys Val Ala Val Lys Thr Met Lys
            260                 265                 270

Pro Gly Ser Met Ser Val Glu Ala Phe Leu Ala Glu Ala Asn Val Met
        275                 280                 285

Lys Thr Leu Gln His Asp Lys Leu Val Lys Leu His Ala Val Val Thr
    290                 295                 300

Lys Glu Pro Ile Tyr Ile Ile Thr Glu Phe Met Ala Lys Gly Ser Leu
305                 310                 315                 320

Leu Asp Phe Leu Lys Ser Asp Glu Gly Ser Lys Gln Pro Leu Pro Lys
                325                 330                 335

Leu Ile Asp Phe Ser Ala Gln Ile Ala Glu Gly Met Ala Phe Ile Glu
            340                 345                 350

Gln Arg Asn Tyr Ile His Arg Asp Leu Arg Ala Ala Asn Ile Leu Val
        355                 360                 365

Ser Ala Ser Leu Val Cys Lys Ile Ala Asp Phe Gly Leu Ala Arg Val
    370                 375                 380

Ile Glu Asp Asn Glu Tyr Thr Ala Arg Glu Gly Ala Lys Phe Pro Ile
385                 390                 395                 400

Lys Trp Thr Ala Pro Glu Ala Ile Asn Phe Gly Ser Phe Thr Ile Lys
                405                 410                 415

Ser Asp Val Trp Ser Phe Gly Ile Leu Leu Met Glu Ile Val Thr Tyr
            420                 425                 430

Gly Arg Ile Pro Tyr Pro Gly Met Ser Asn Pro Glu Val Ile Arg Ala
        435                 440                 445

Leu Glu Arg Gly Tyr Arg Met Pro Arg Pro Glu Asn Cys Pro Glu Glu
    450                 455                 460

Leu Tyr Asn Ile Met Met Arg Cys Trp Lys Asn Arg Pro Glu Glu Arg
465                 470                 475                 480

Pro Thr Phe Glu Tyr Ile Gln Ser Val Leu Asp Asp Phe Tyr Thr Ala
                485                 490                 495

Thr Glu Ser Gln Tyr Gln Gln Gln Pro
            500                 505
```